US010793871B2

(12) United States Patent
Pai et al.

(10) Patent No.: US 10,793,871 B2
(45) Date of Patent: Oct. 6, 2020

(54) NUCLEIC ACID MOLECULE ENCODING GLE1 PROTEIN VARIANT WITH INCREASED PHYTIC ACID SENSITIVITY AND USE THEREOF

(71) Applicant: University-Industry Foundation, Yonsei University, Seoul (KR)

(72) Inventors: Hyun Sook Pai, Seoul (KR); Ho-Seok Lee, Seoul (KR)

(73) Assignee: UNIVERSITY-INDUSTRY FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 15/543,882

(22) PCT Filed: Jan. 15, 2016

(86) PCT No.: PCT/KR2016/000481
§ 371 (c)(1),
(2) Date: Jul. 14, 2017

(87) PCT Pub. No.: WO2016/114636
PCT Pub. Date: Jul. 21, 2016

(65) Prior Publication Data
US 2018/0119166 A1 May 3, 2018

(30) Foreign Application Priority Data
Jan. 15, 2015 (KR) ........................ 10-2015-0007246

(51) Int. Cl.
| C12N 15/82 | (2006.01) |
|---|---|
| C07K 14/415 | (2006.01) |
| C07K 14/00 | (2006.01) |
| C12N 15/62 | (2006.01) |
| C07K 4/10 | (2006.01) |

(52) U.S. Cl.
CPC .......... *C12N 15/8271* (2013.01); *C07K 14/00* (2013.01); *C07K 14/415* (2013.01); *C12N 15/62* (2013.01); *C12N 15/8218* (2013.01); *C12N 15/8243* (2013.01); *C12N 15/8245* (2013.01); *C12N 15/8261* (2013.01); *C12N 15/8267* (2013.01); *C07K 4/10* (2013.01); *Y02A 40/146* (2018.01)

(58) Field of Classification Search
None
See application file for complete search history.

(56) References Cited
U.S. PATENT DOCUMENTS

| 5,004,863 | A | 4/1991 | Umbeck |
|---|---|---|---|
| 5,349,124 | A | 9/1994 | Fischhoff et al. |
| 5,416,011 | A | 5/1995 | Hinchee et al. |
| 2013/0333061 | A1* | 12/2013 | Wu ...................... C07K 14/415 800/260 |

FOREIGN PATENT DOCUMENTS

| JP | 2001513326 A | 9/2001 |
|---|---|---|
| JP | 2003526335 A | 9/2003 |
| WO | 2006029296 A2 | 3/2006 |

OTHER PUBLICATIONS

Totoki et al. (NCBI, GenBank Accession No. Q0WPZ7; Published Nov. 28, 2006).*
Wells (Biochemistry 29:8509-8517, 1990).*
Guo et al. (PNAS, 101: 9205-9210, 2004).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Keskin et al. (Protein Science, 13:1043-1055, 2004).*
McConnell et al. (Nature, 411:709-713, 2001).*
Hanzawa et al. (PNAS, 102:7748-7753, 2005).*
Wishart et al. (JBC, 270:26782-26785, 1995).*
Nousiainen et al. (Nature Genetics, 40:155-157, 2008).*
Doerks et al., (TIG, 14:248-250, 1998).*
Smith et al. (Nature Biotechnology, 15:1222-1223, 1997).*
Bork et al. (TIG, 12:425-427, 1996).*
Alcazar-Roman et al., "Control of mRNA Export and Translation Termination by Inositol Hexakisphosphate Requires Specific Interaction with Gle1," May 2010. pp. 16683-16692, The Journal of Biological Chemistry, vol. 285, No. 22.
Folkmann et al., "Dbp5, Gle1-IP6 and Nup159," 2011, pp. 540-548, Nucleus, vol. 2, No. 6.
Montpetit et al., "A conserved mechanism of DEAD-box ATPase activation by nucleoporins and InsP6 in mRNA export," Apr. 2011, pp. 238-244, Nature, vol. 472.
Lee et al., "InsP6-Sensitive Variants of the Gle1 mRNA Export Factor Rescue Growth and Fertility Defects of the ipk1 Low-Phytic-Acid Mutation in *Arabidopsis*," Feb. 2015, pp. 417-431, The Plant Cell, vol. 27.
Core Research Support Project, "New Functional Analysis of Mitochondrial Nucleoprotein Nucleoporins and Linkage Mechanism with Plant Growth Regulatory System", May 2012, 59 pages, Korea Research Foundation, Yonsei University, Director Bae Hyun Sook. English translation of Summary included.
Patent Cooperation Treaty, International Search Report for PCT/KR2016/000481 dated Apr. 27, 2016, 3 pages.

(Continued)

*Primary Examiner* — Vinod Kumar
(74) *Attorney, Agent, or Firm* — Heslin Rothenberg Farley & Mesiti P.C.

(57) ABSTRACT

Provided are a nucleic acid molecule encoding a Gle1 protein variant comprising a phytic acid-binding pocket, a protein encoded by the nucleic acid molecule and a method using the nucleic acid molecule. The Gle1 protein variant has an increased sensitivity to phytic acid in plants, and also has an effect of highly increasing vegetative growth, seed yield, seed performance and abiotic stress tolerance in plants containing a low level of phytic acid. Therefore, high yield low-$InsP_6$ crops may be cultivated using the nucleic acid molecule.

17 Claims, 38 Drawing Sheets

Specification includes a Sequence Listing.

(56) References Cited

OTHER PUBLICATIONS

"Jatropha curcas hypothetical protein," Uniprot, XP002782012, retrieved from EBI Accession Database No. EMPL: KDP26670, p. 1.
"Uncharacterized protein," Uniprot, XP002782013, retrieved from EPI Accession Database No. A0A067K349, pp. 1-2.
Extended European Search Report dated Jun. 25, 2018, pp. 1-6.

* cited by examiner

[FIG. 1A]
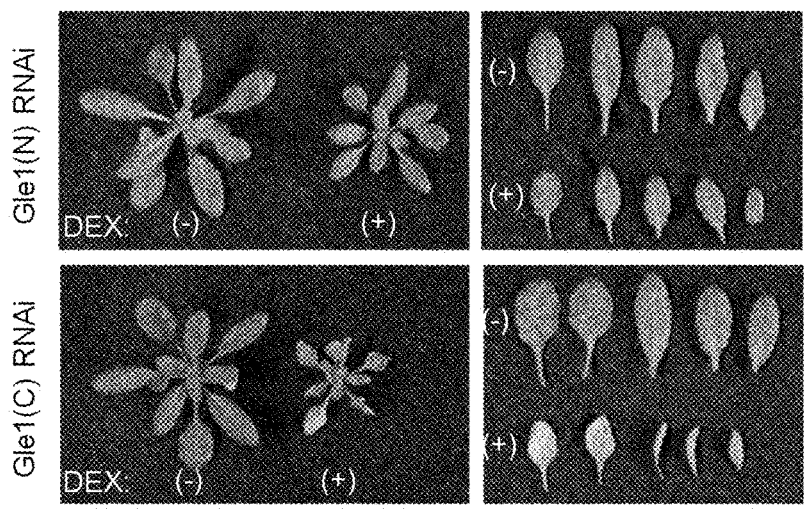
[FIG. 1B]
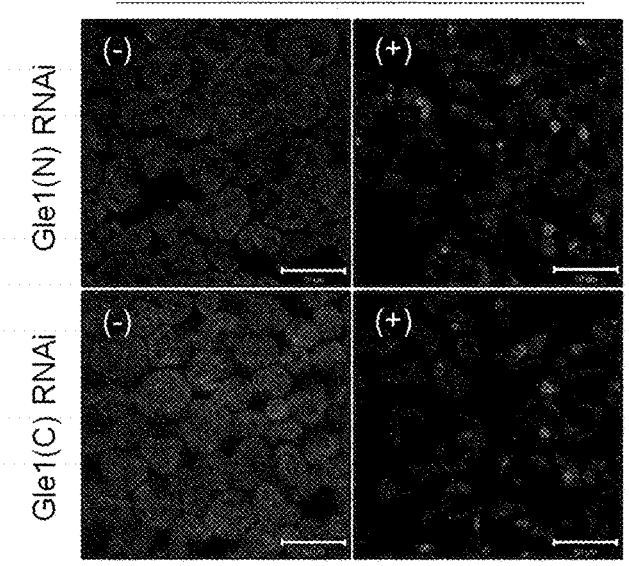

[FIG. 1C]
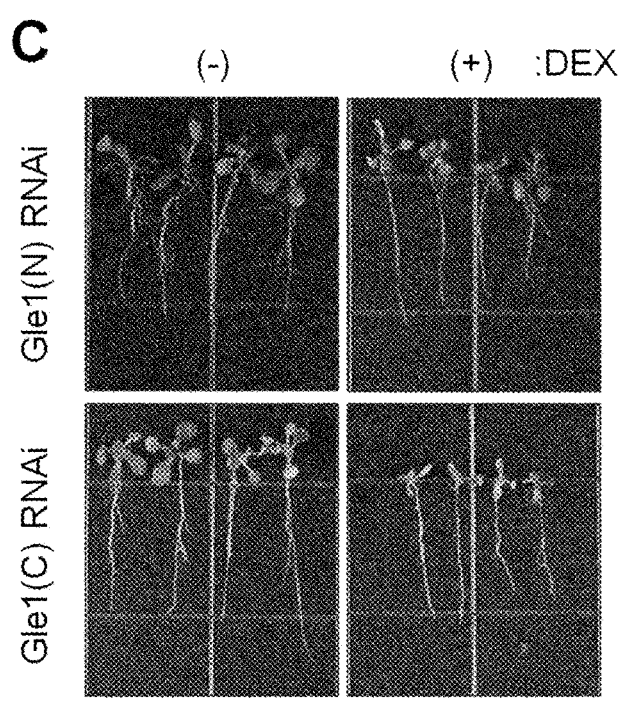

[FIG. 1D]
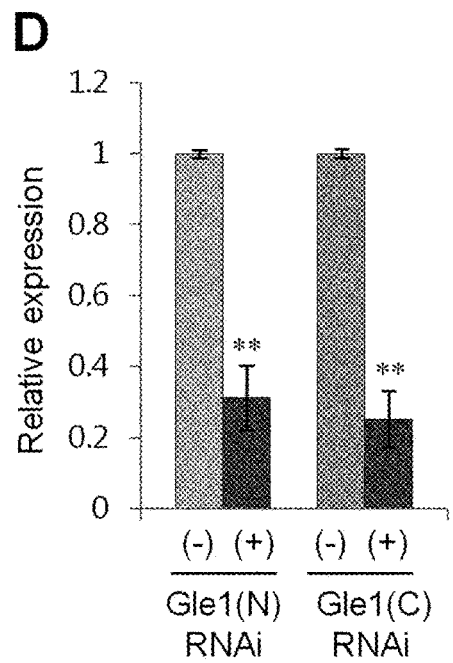
[FIG. 1E]
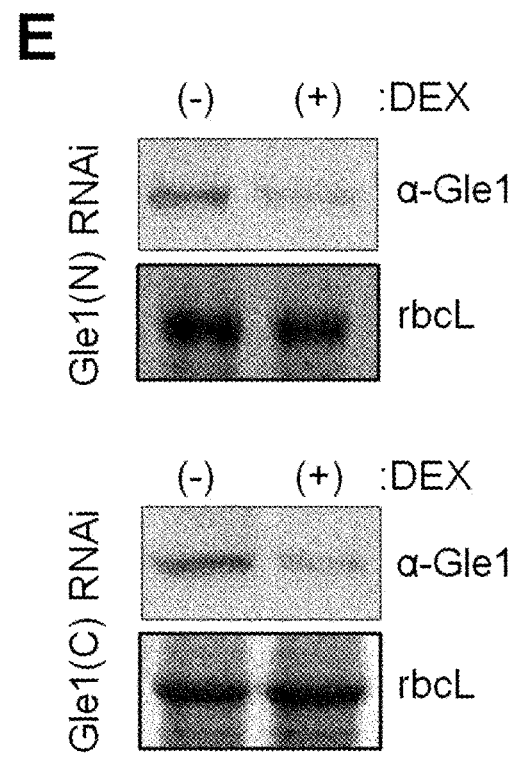

[FIG. 2A]
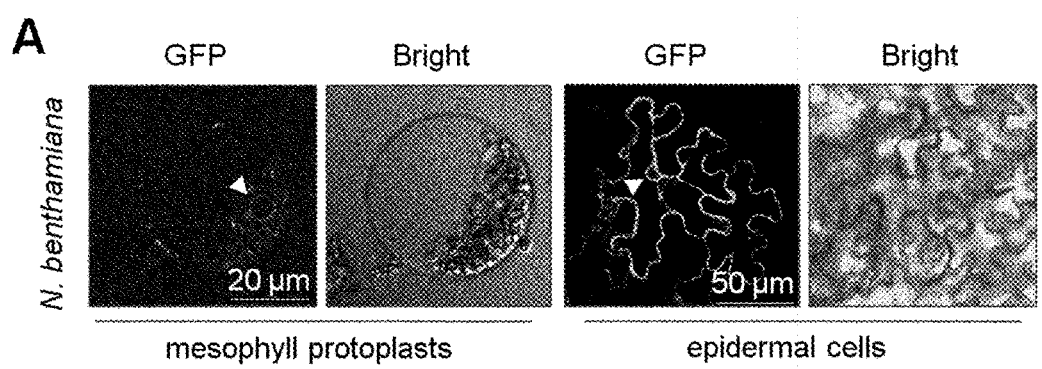

[FIG. 2B]
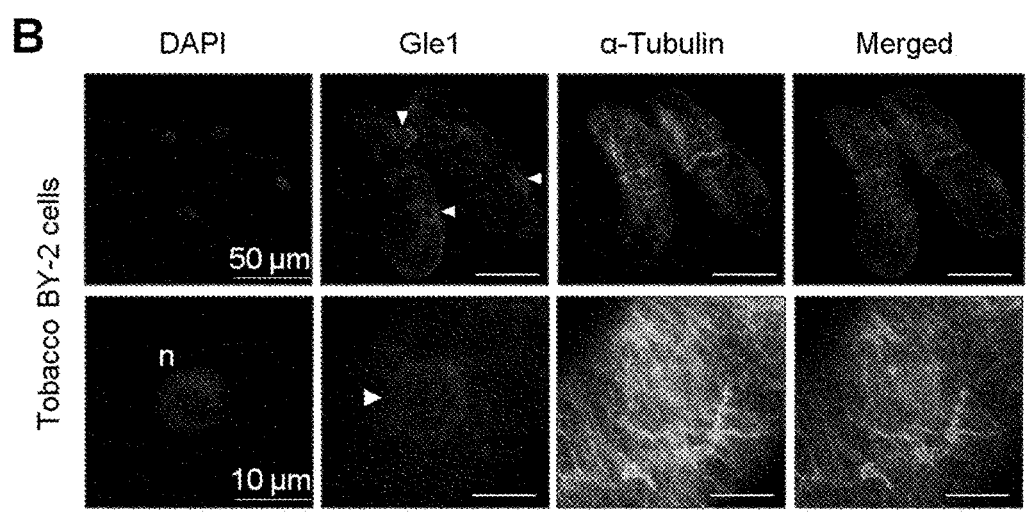
[FIG. 2C]
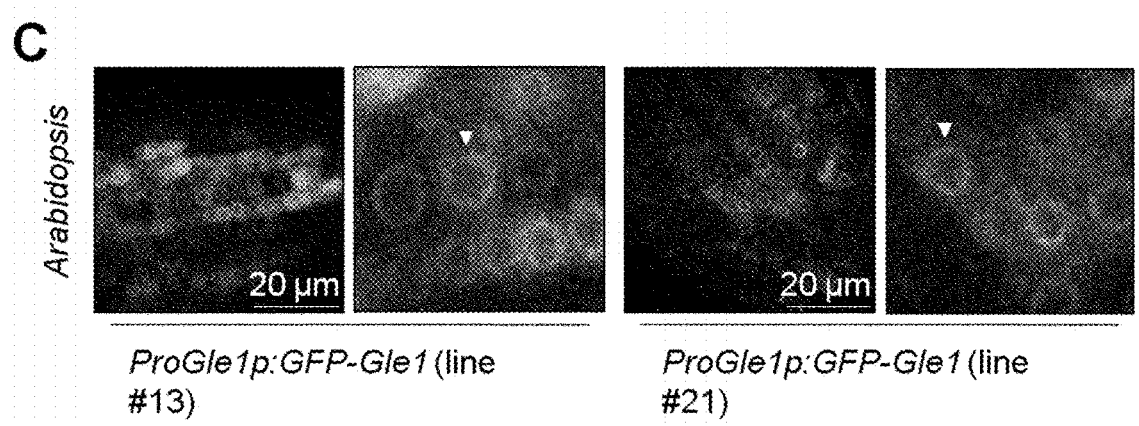

[FIG. 3A]
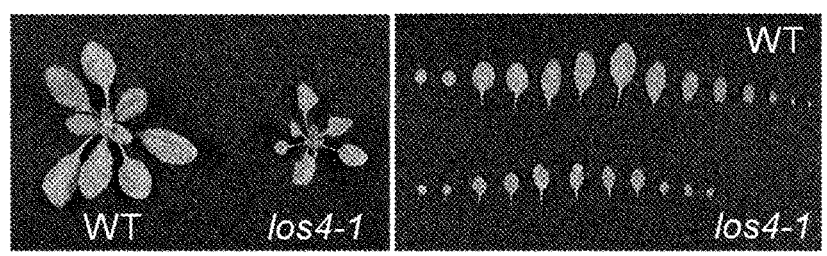
[FIG. 3B]
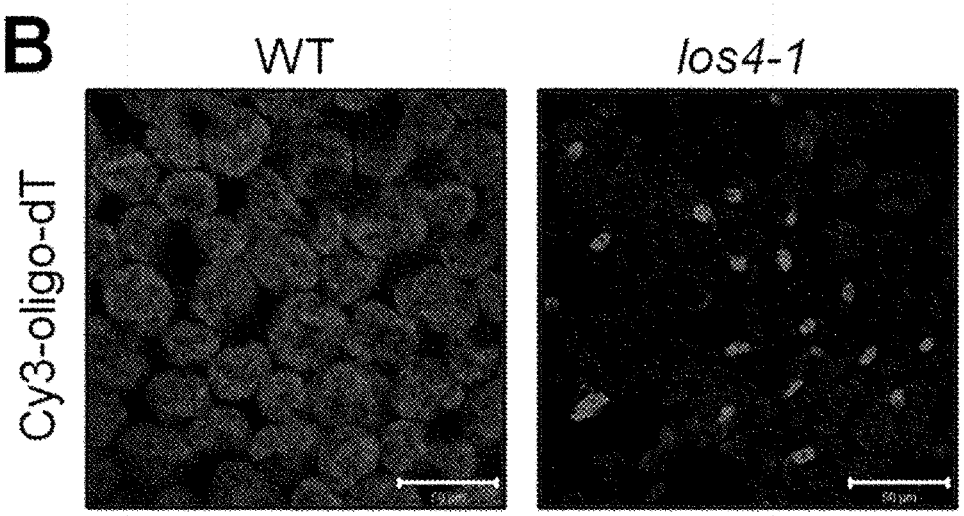

[FIG. 3C]
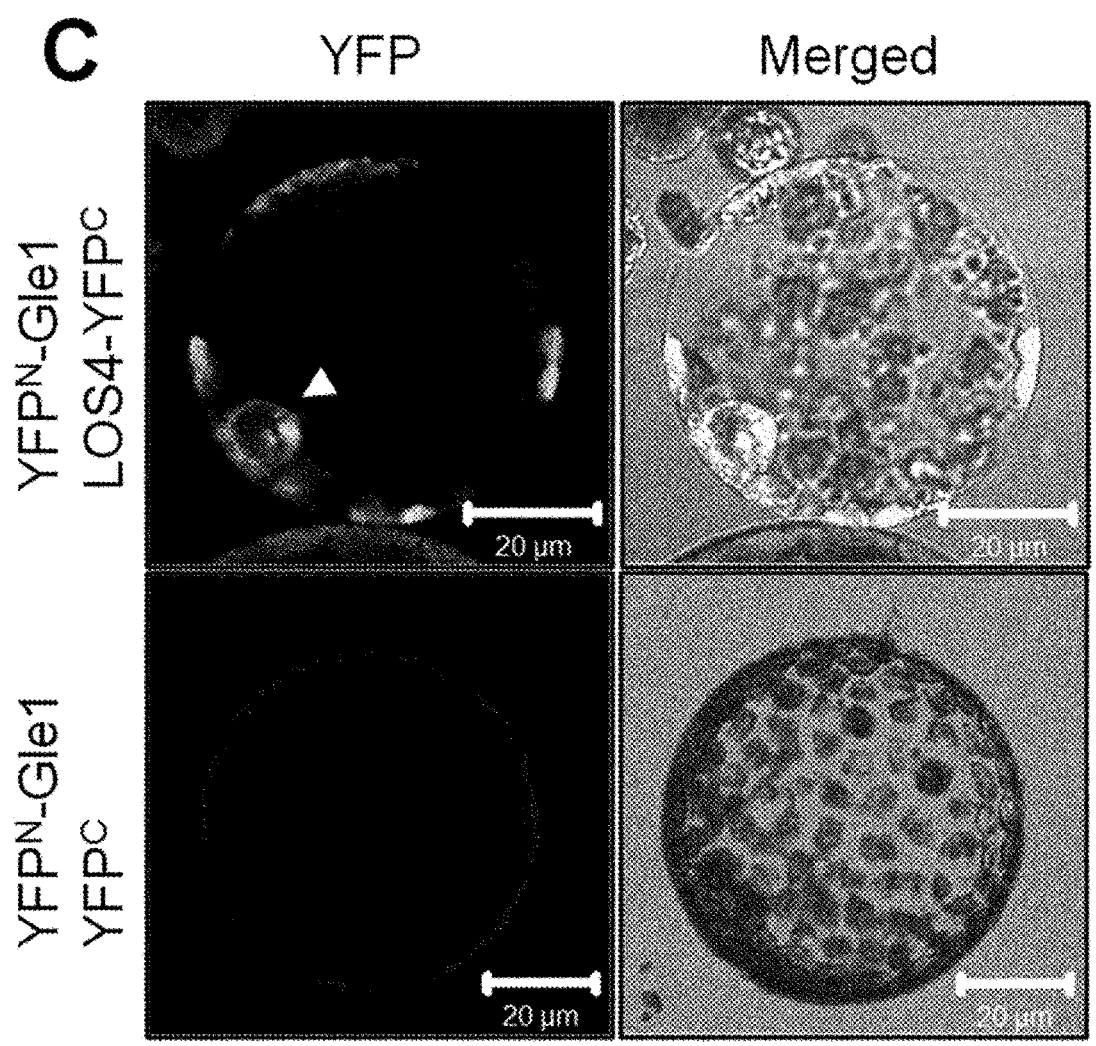

[FIG. 3D]
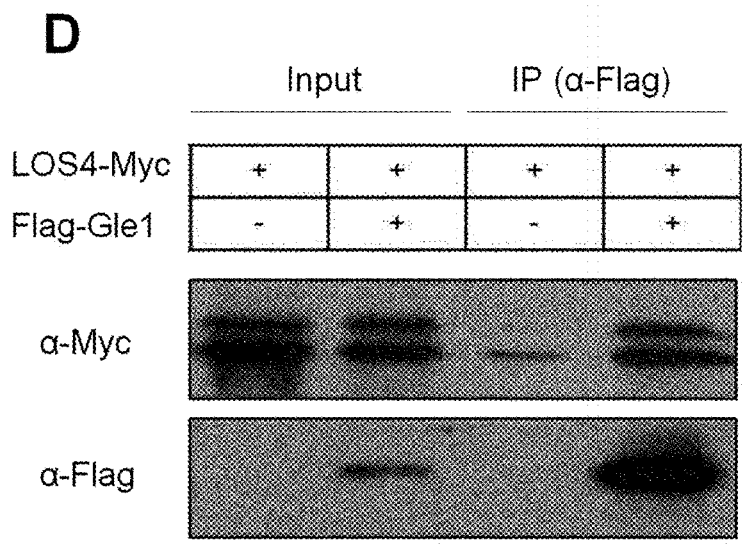
[FIG. 3E]
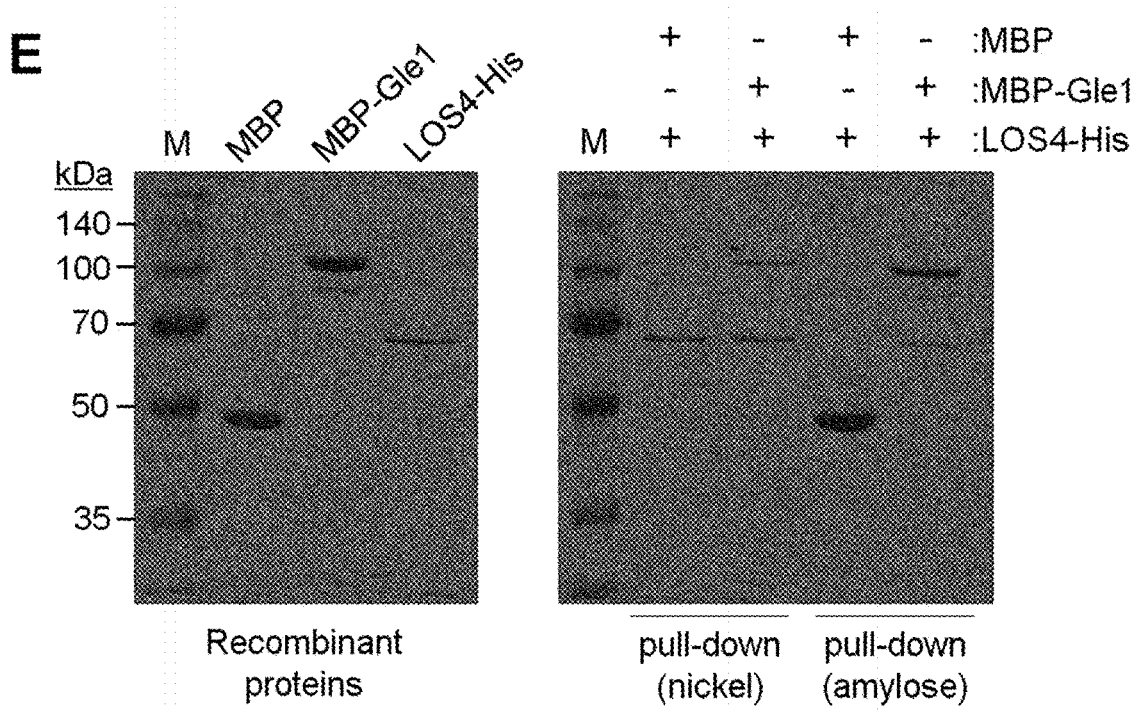

[FIG. 4A]
A
```
                431              439
Gle1:        LAEFHKACI
Gle1(IS1):   LAEFHKKCI
Gle1(IS2):   LAKFHKKCI
Gle1(ID):    LAEFHAACI
```
[FIG. 4B]
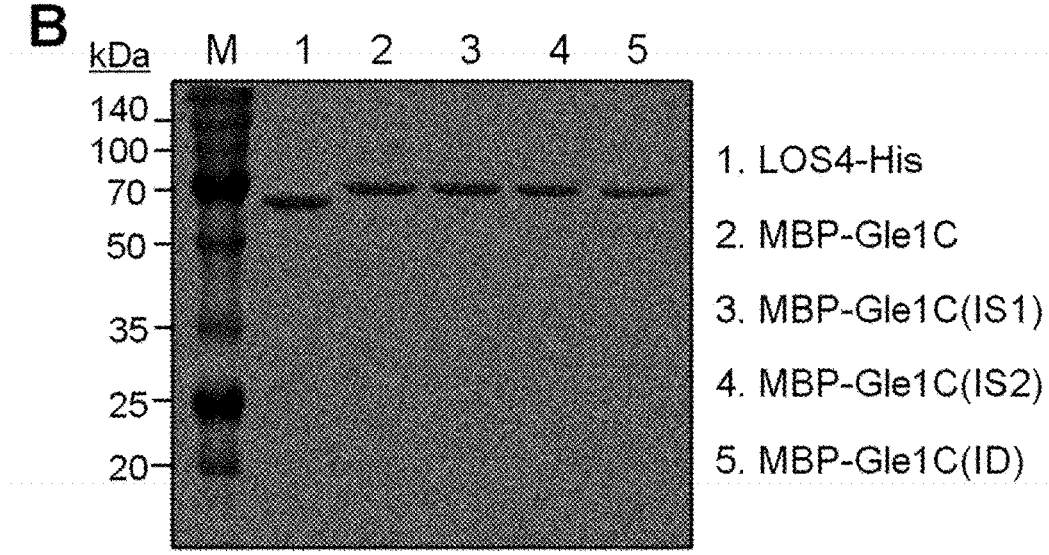

[FIG. 4C]
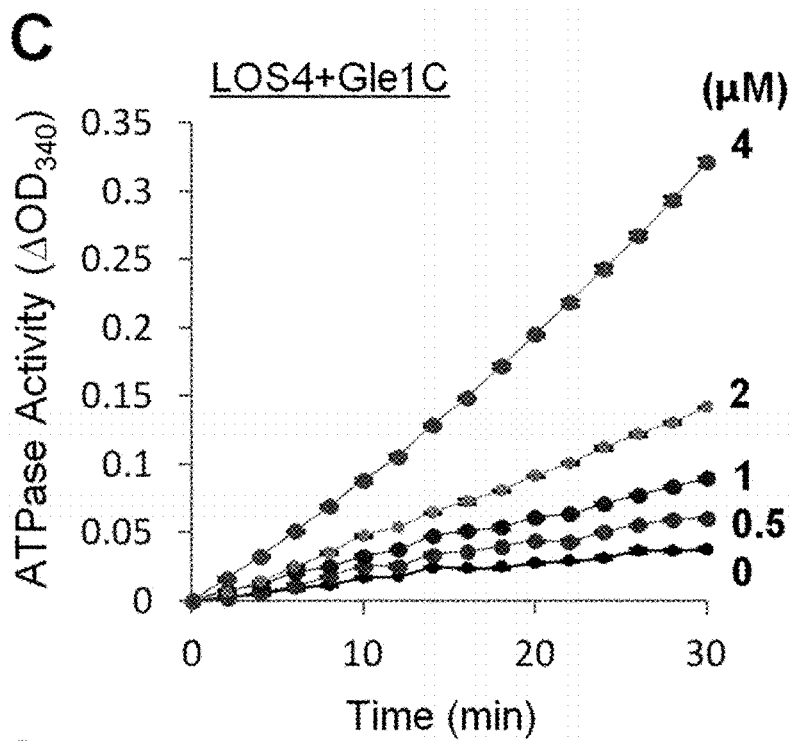
[FIG. 4D]
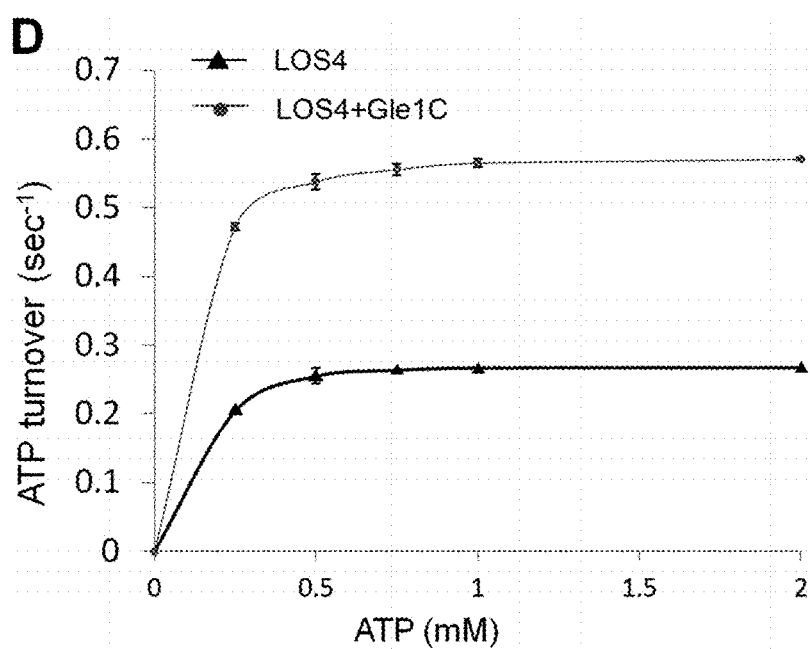

【FIG. 4E】
E
| Samples | $k_{cat}$ (sec$^{-1}$) |
|---|---|
| LOS4 | 0.267 ± 0.001 |
| LOS4 + Gle1C | 0.565 ± 0.005 |
【FIG. 4F】
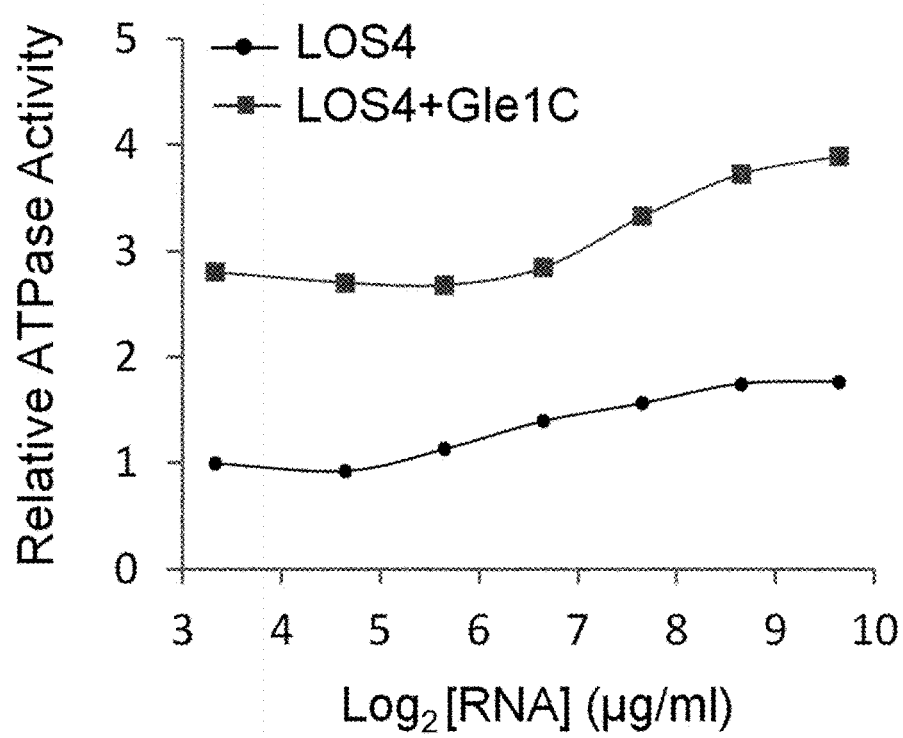

[FIG. 4G]
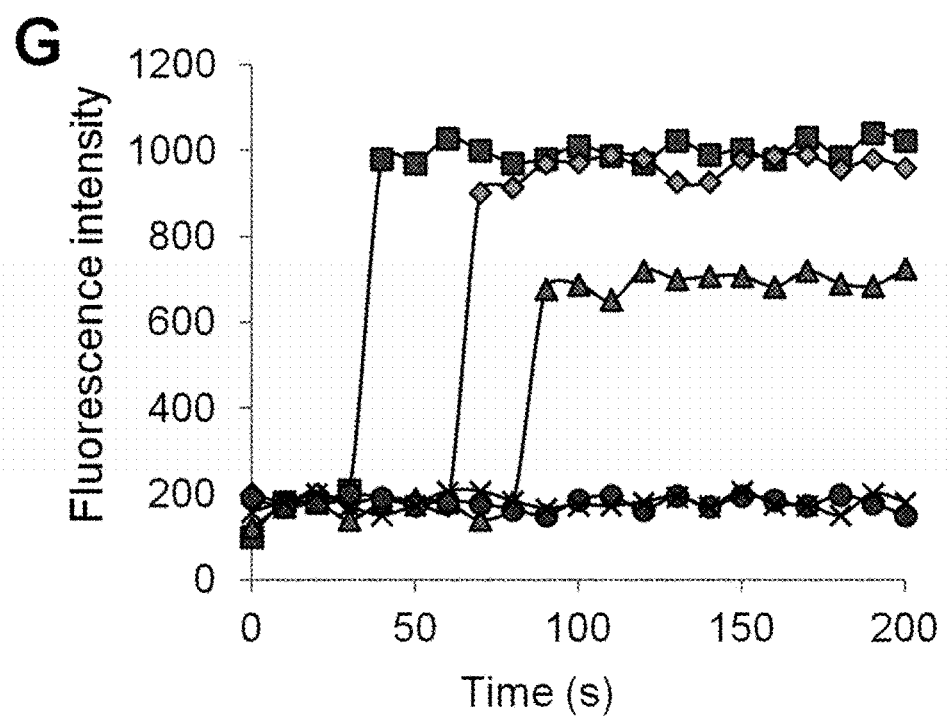
[FIG. 5A]
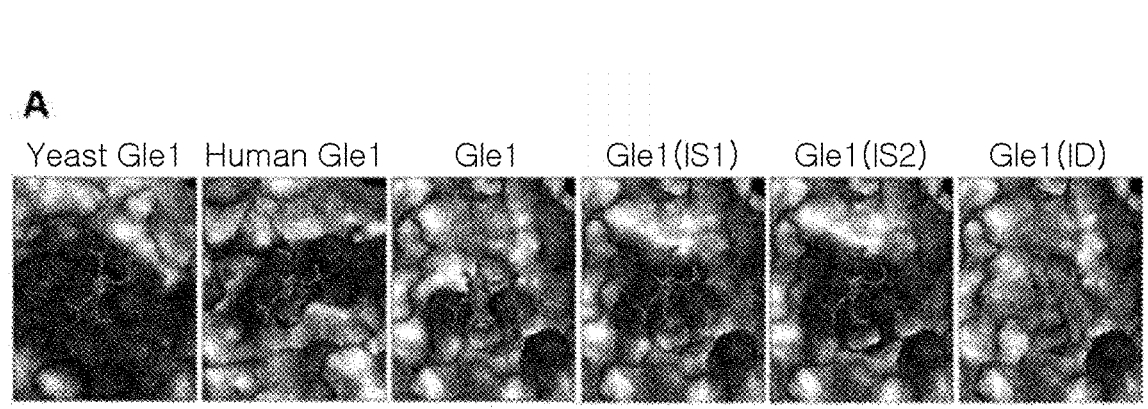

[FIG. 5B]
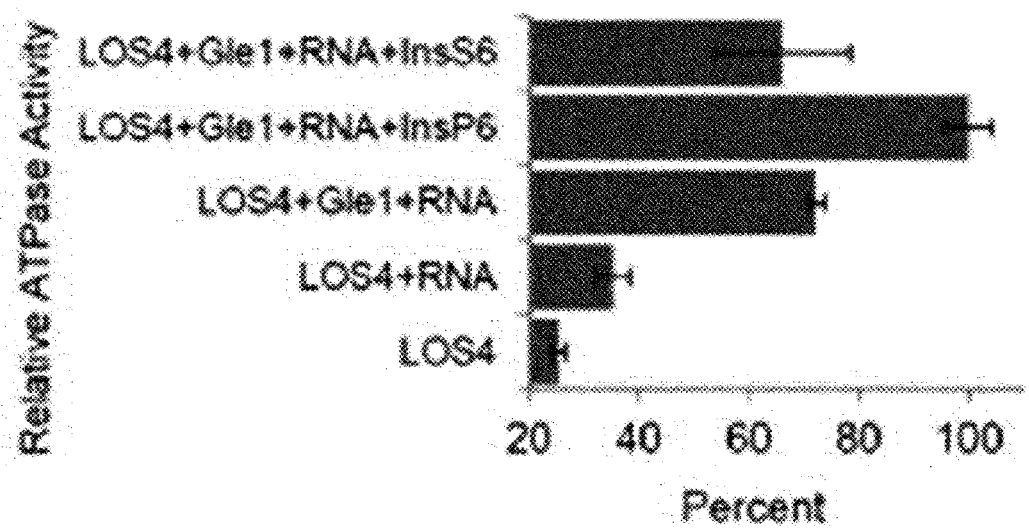
[FIG. 5C]
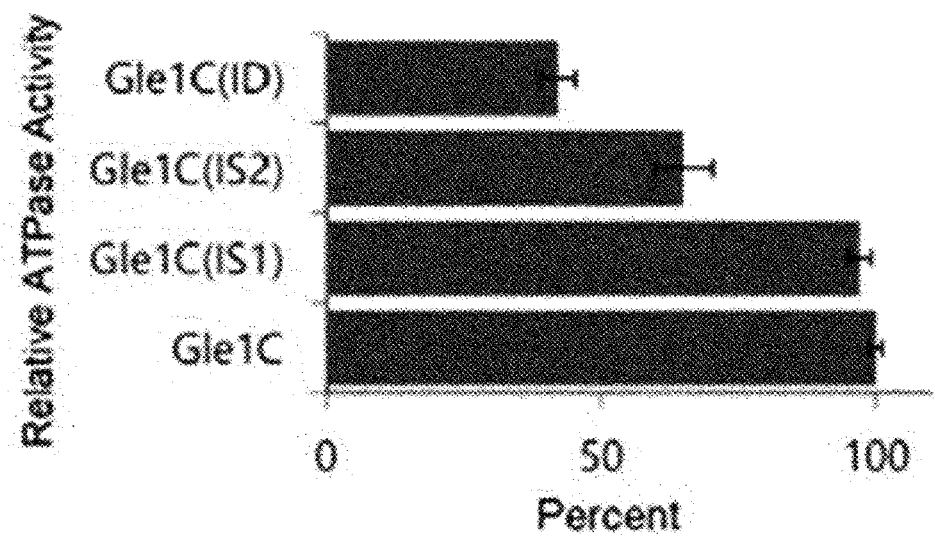

【FIG. 5D】
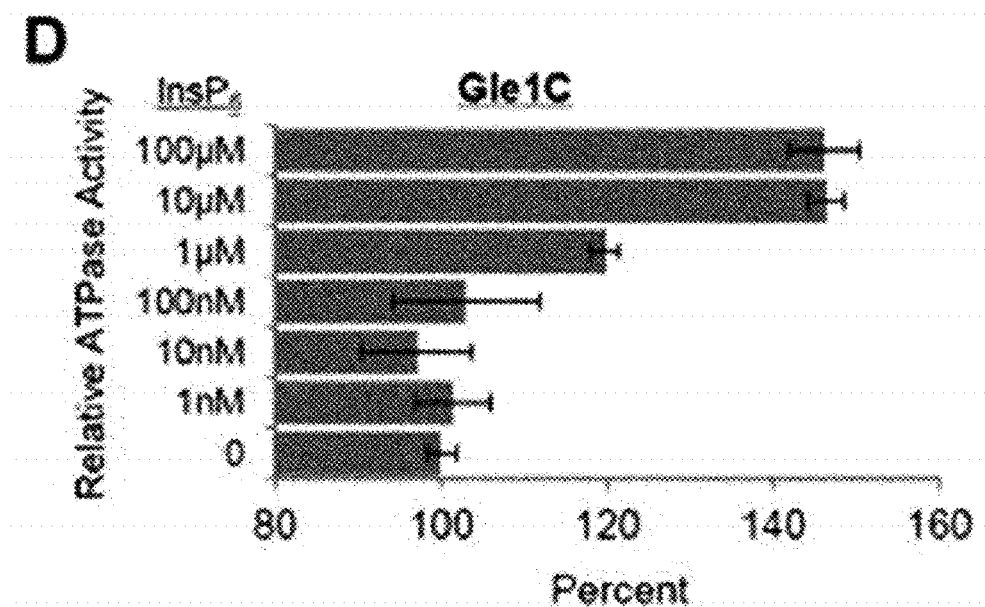
【FIG. 5E】
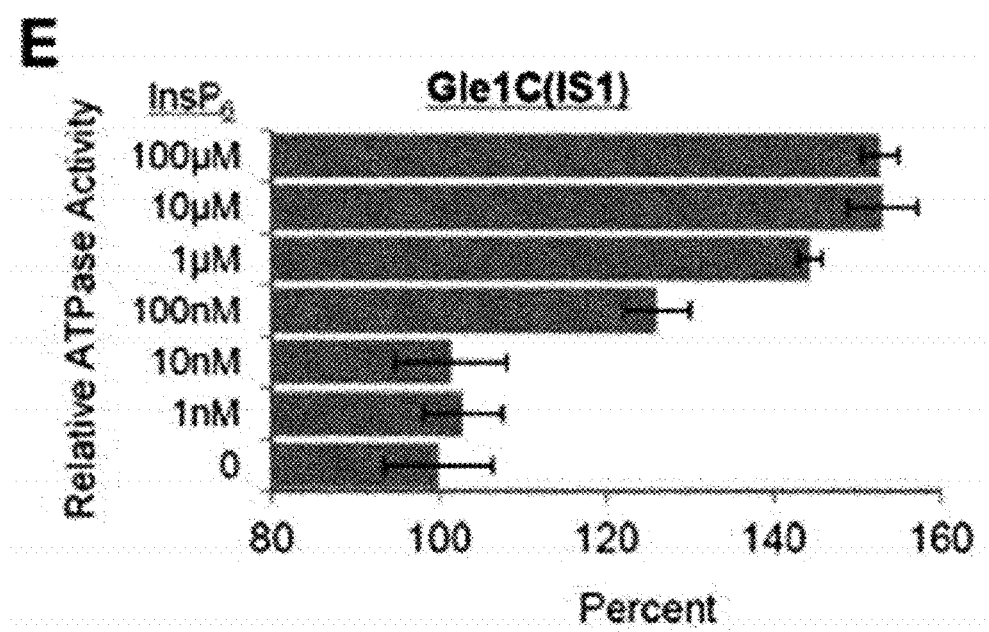

[FIG. 5F]
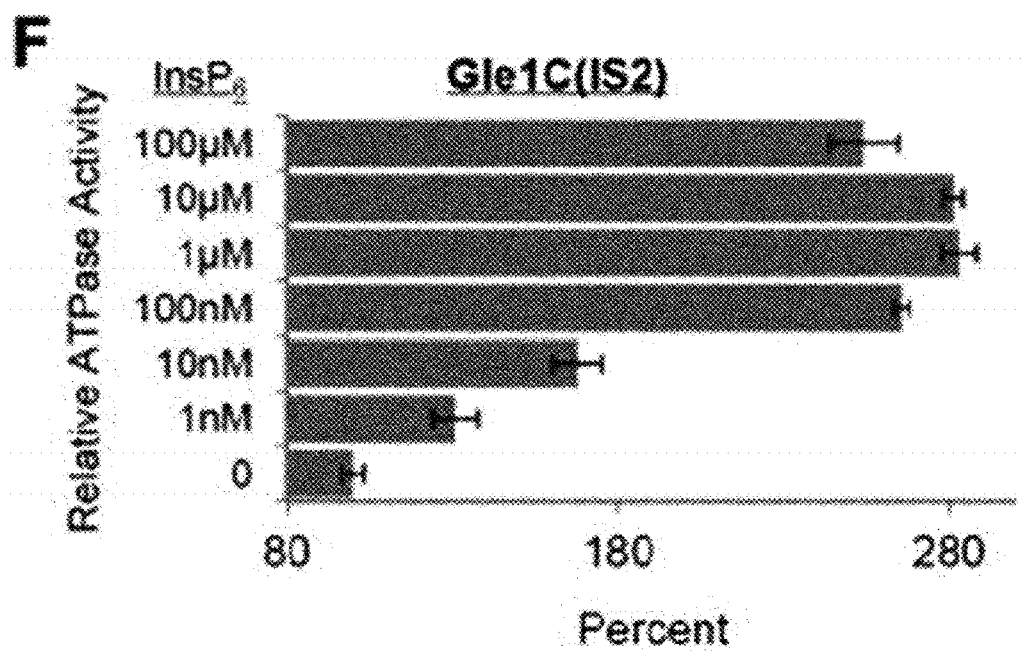
[FIG. 5G]
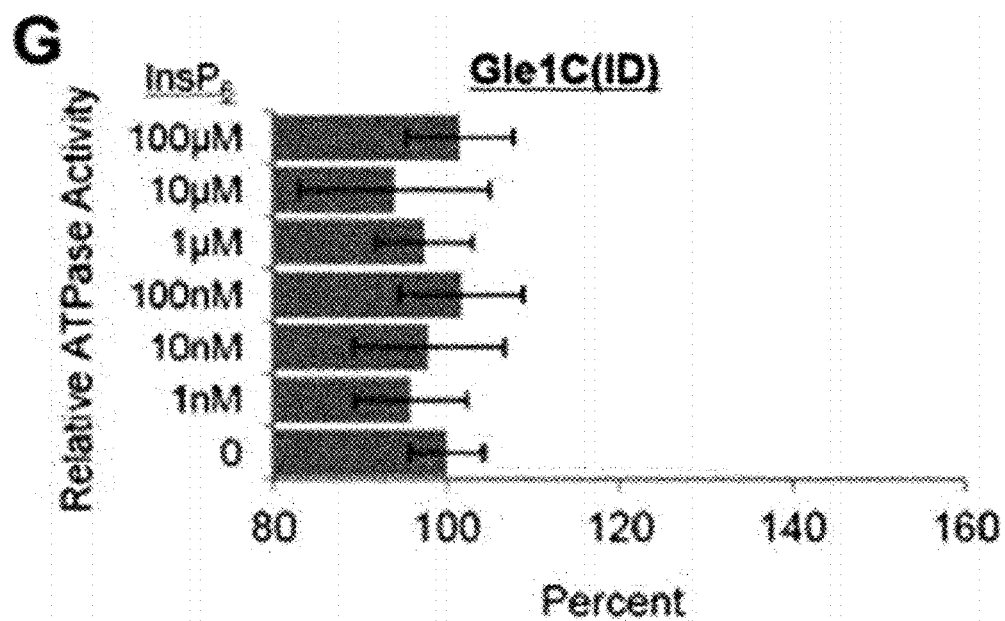

[FIG. 6A]
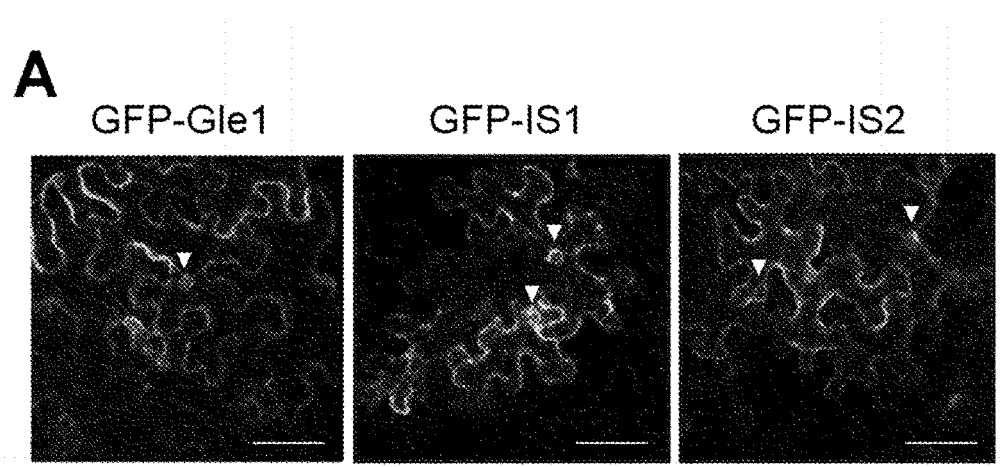
[FIG. 6B]
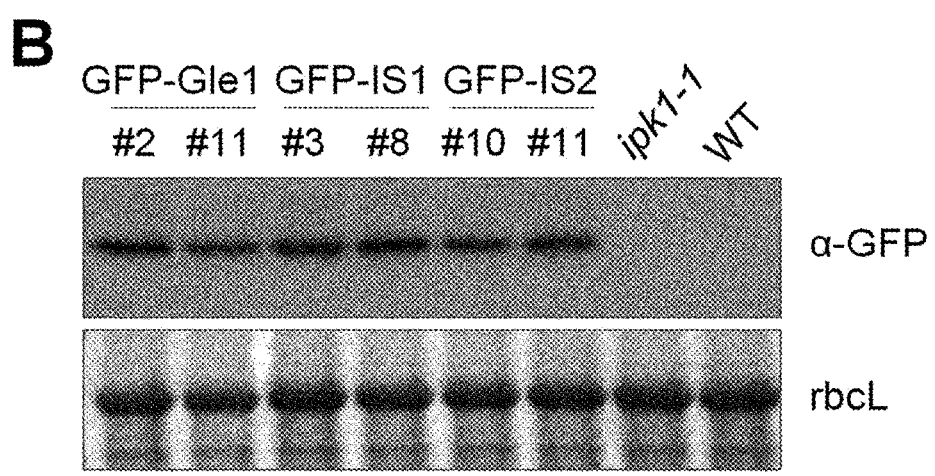

[FIG. 6C]
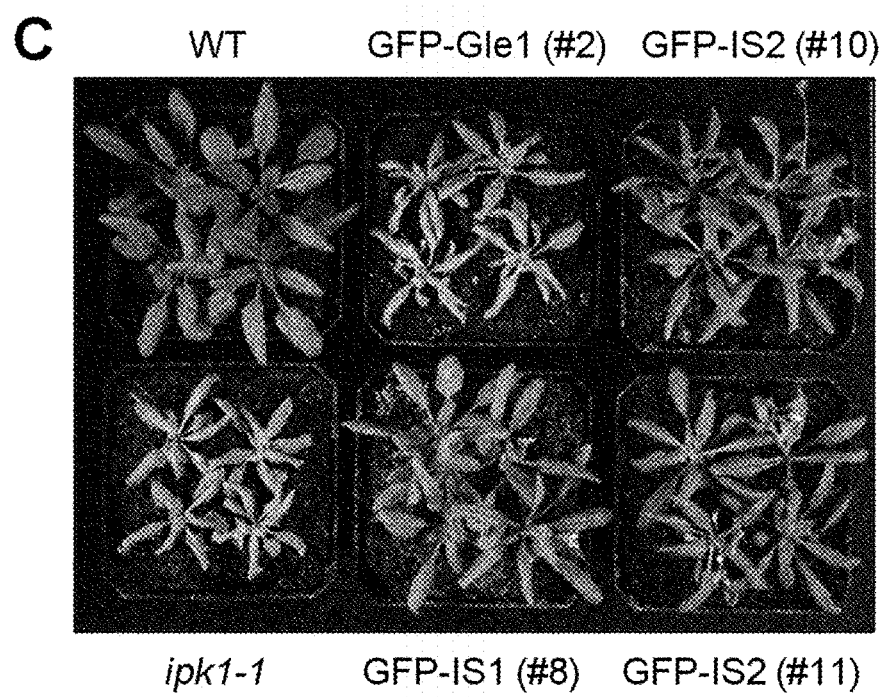
[FIG. 6D]
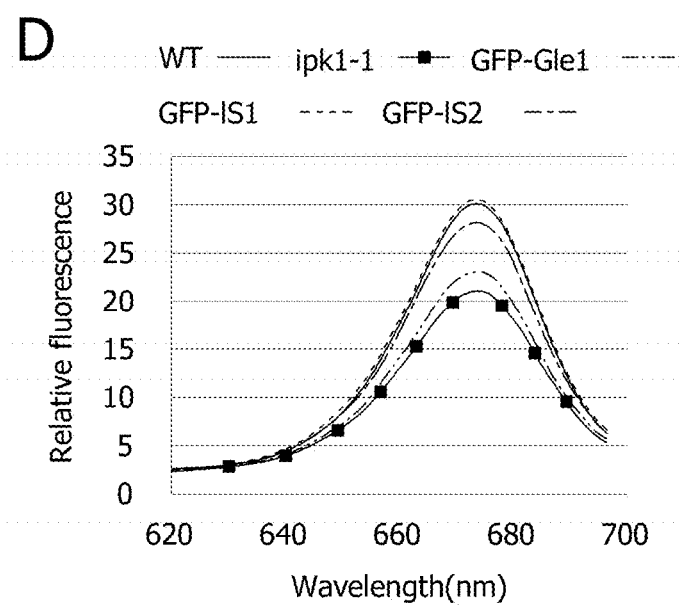

[FIG. 6E]
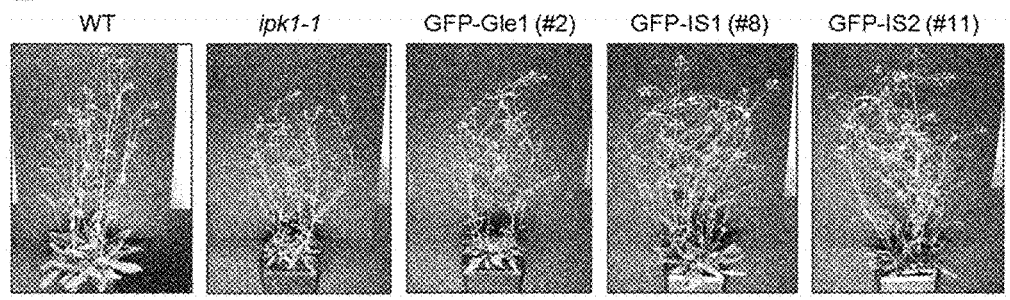
[FIG. 6F]
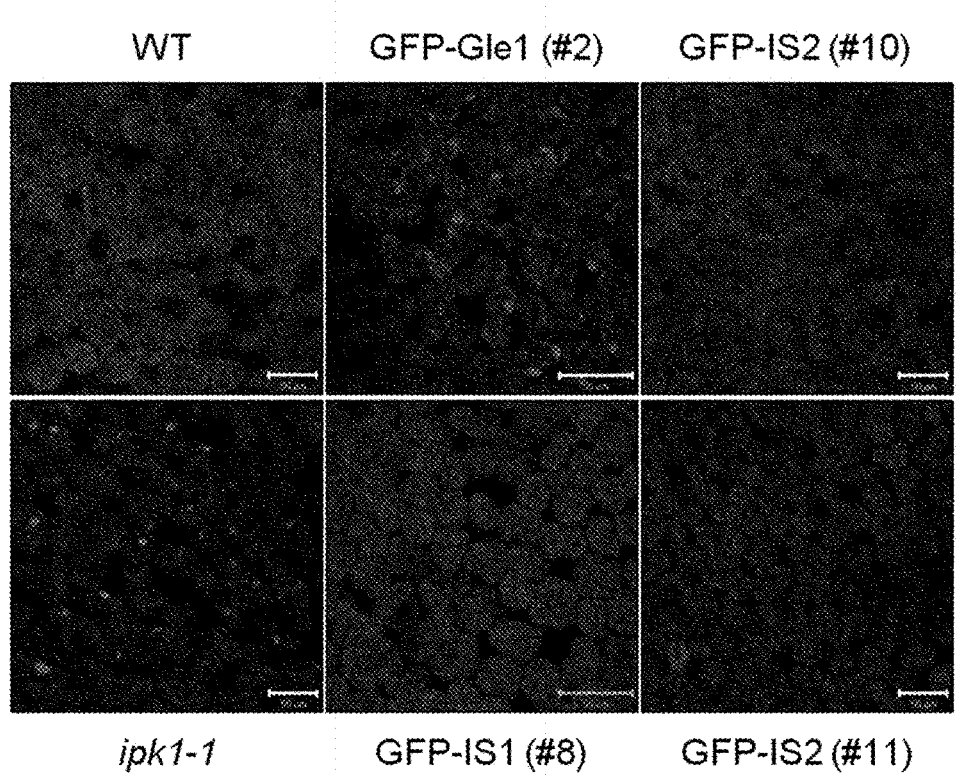

[FIG. 7A]
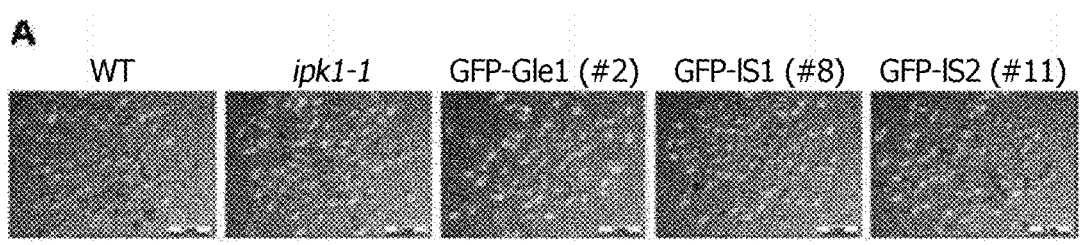

[FIG. 7B]

| Lines | WT | epr1-1 | GFP-Gle1 (#2) | GFP-Gle1 (#11) | GFP-IS1 (#3) | GFP-IS1 (#8) | GFP-IS2 (#10) | GFP-IS2 (#11) |
|---|---|---|---|---|---|---|---|---|
| Seed mass (mg) / 200 seeds | 3.5±0.1 | 3.6±0.1 | 3.5±0.1 | 3.6±0.1 | 3.6±0.1 | 3.7±0.1 | 3.6±0.1 | 3.6±0.1 |
| Seed yield (g) / plant | 0.131± 0.02 | 0.069± 0.01 | 0.086± 0.01 | 0.079± 0.01 | 0.129± 0.03 | 0.151± 0.04 | 0.151± 0.01 | 0.159± 0.01 |
| Relative seed yield | 100 | 52.7 | 65.6 | 60.3 | 98.5 | 115.3 | 115.3 | 120.6 |

[FIG. 7C]
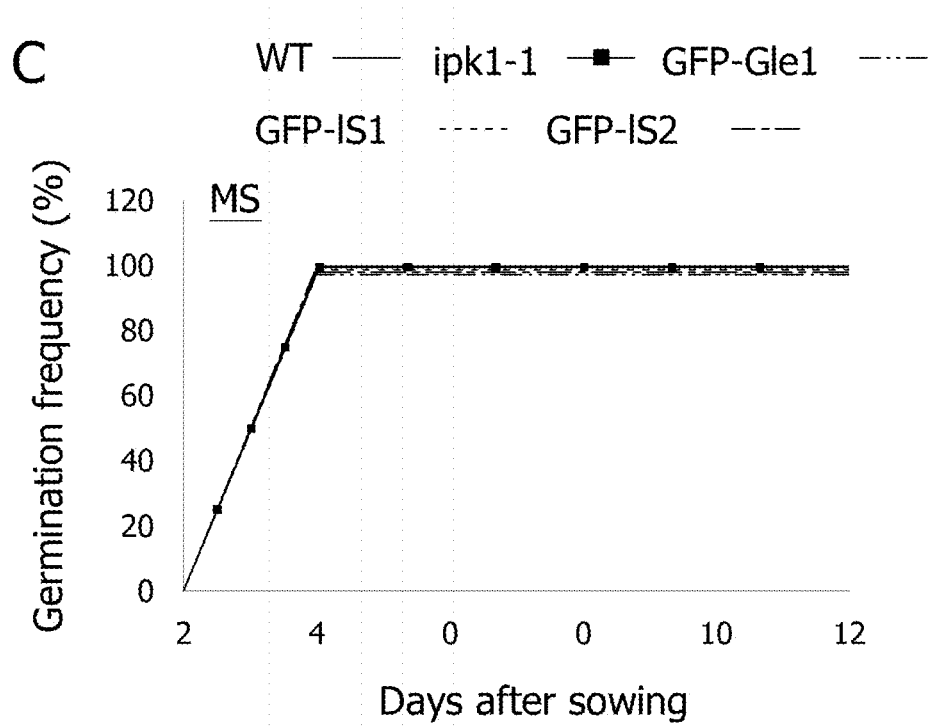
[FIG. 7D]
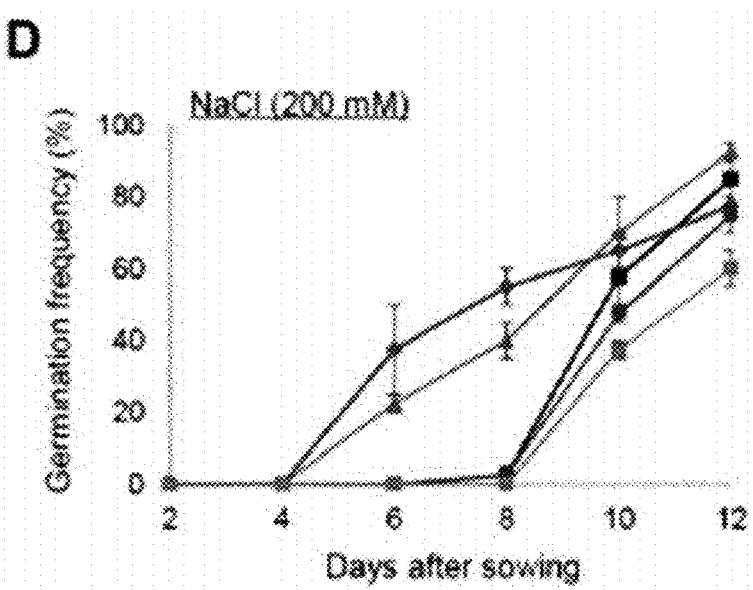

【FIG. 7E】
| Sample | mg InsP$_6$ / g seed dw | mg P$_i$ / g seed dw |
|---|---|---|
| WT | 11.13 ± 0.78 | 1.91 ± 0.25 |
| ipk1-1 | 1.73 ± 0.17 | 2.74 ± 0.44 |
| GFP-Gle1 (#2) | 1.84 ± 0.19 | 2.65 ± 0.62 |
| GFP-IS1 (#8) | 1.68 ± 0.33 | 2.25 ± 0.33 |
| GFP-IS2 (#11) | 1.83 ± 0.62 | 2.73 ± 0.04 |
【FIG. 8A】
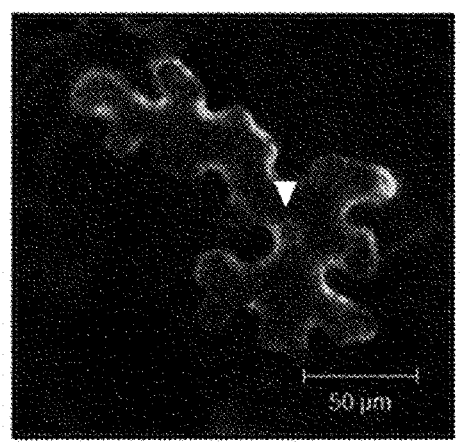

[FIG. 8B]
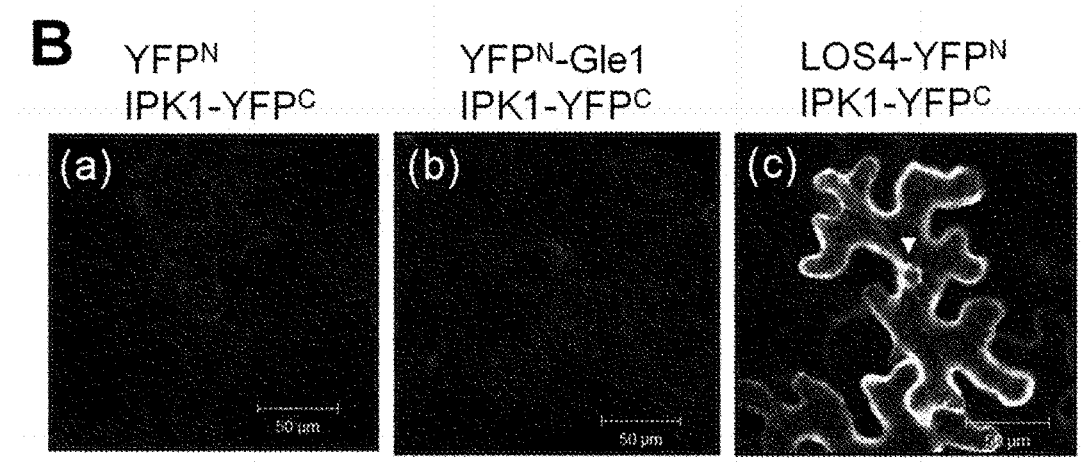
[FIG. 8C]
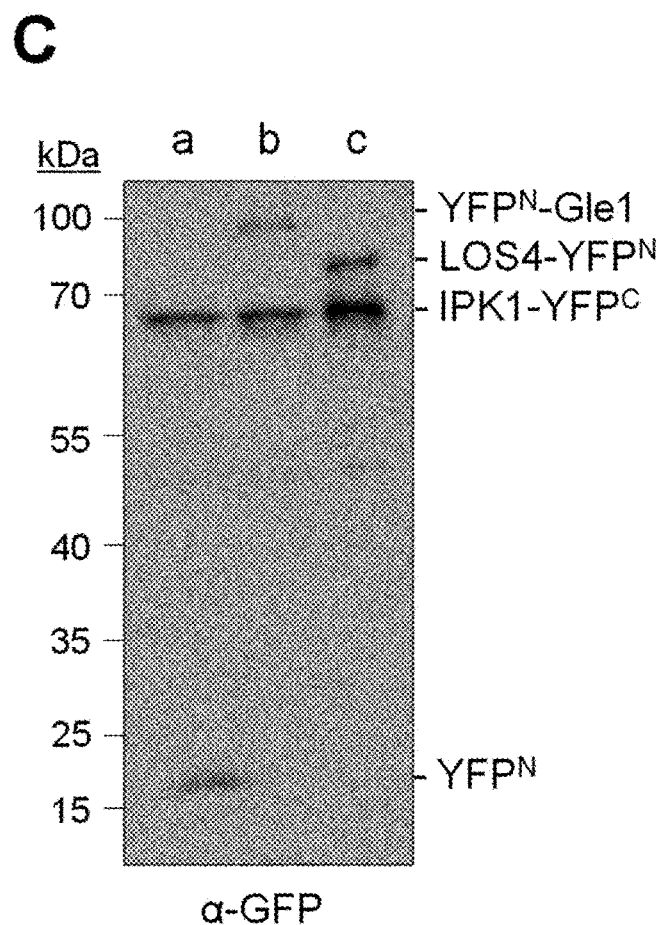

【FIG. 9】
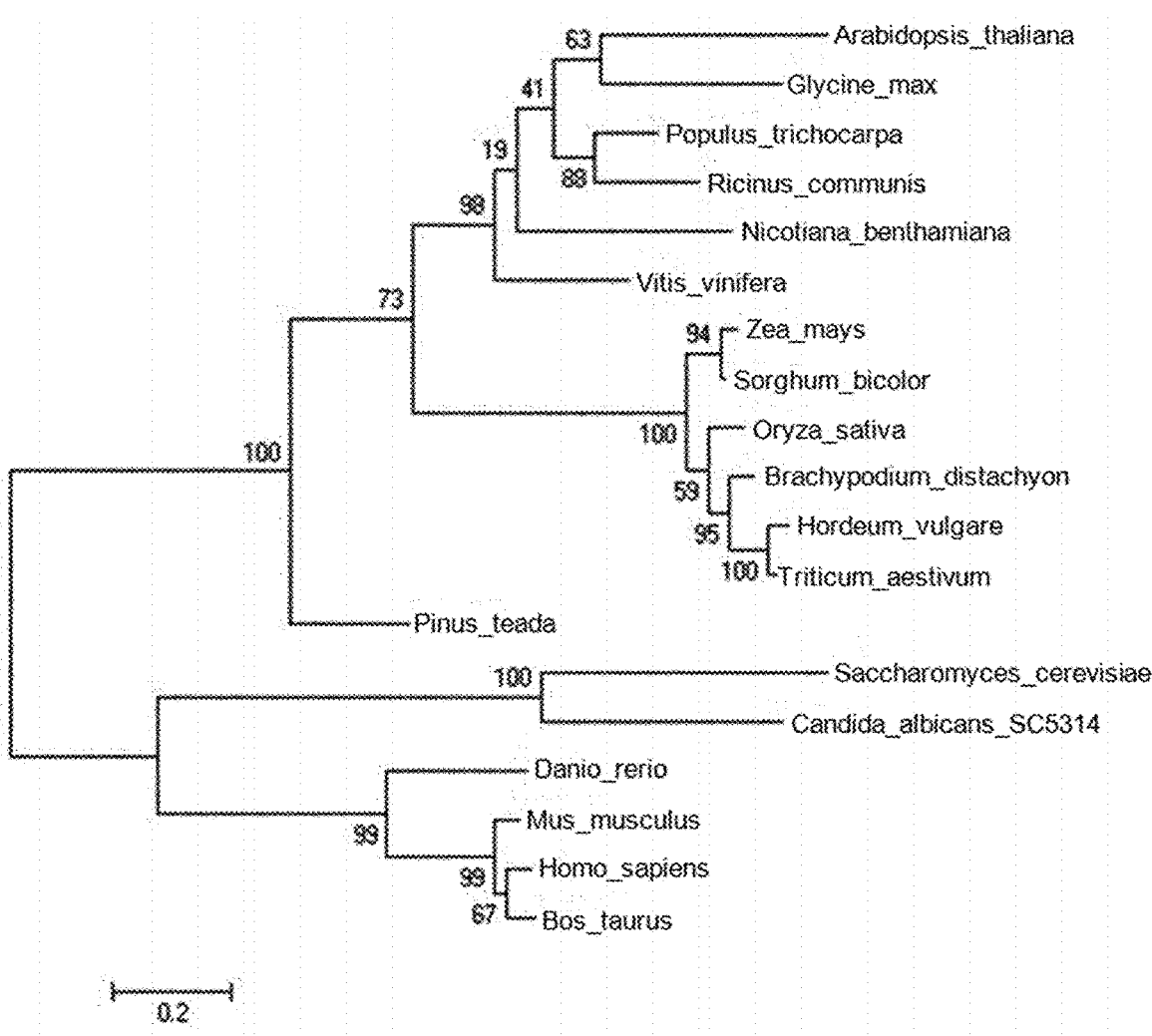
【FIG. 10A】
A
Arabidopsis Gle1

[FIG. 10B]

[FIG. 11A]
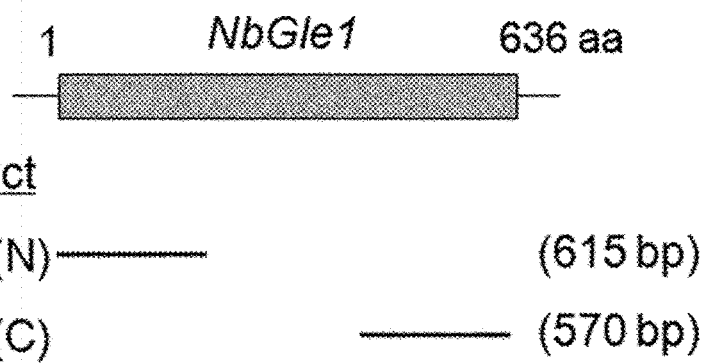
[FIG. 11B]
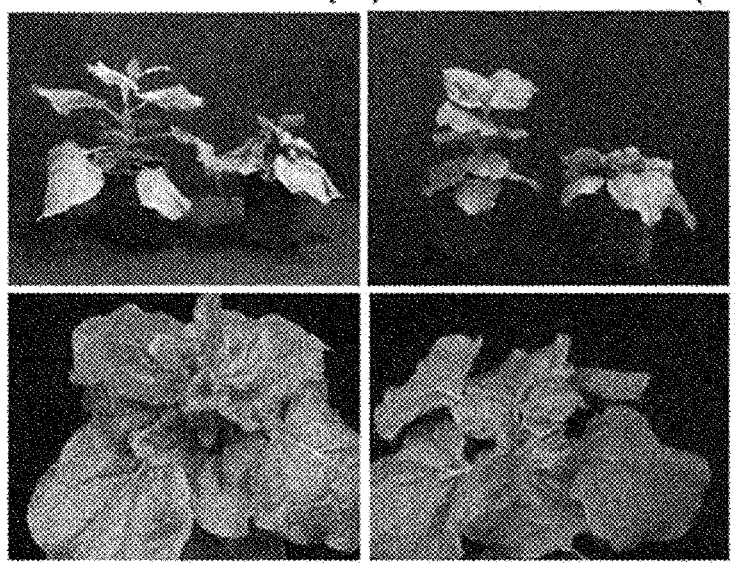

[FIG. 11C]
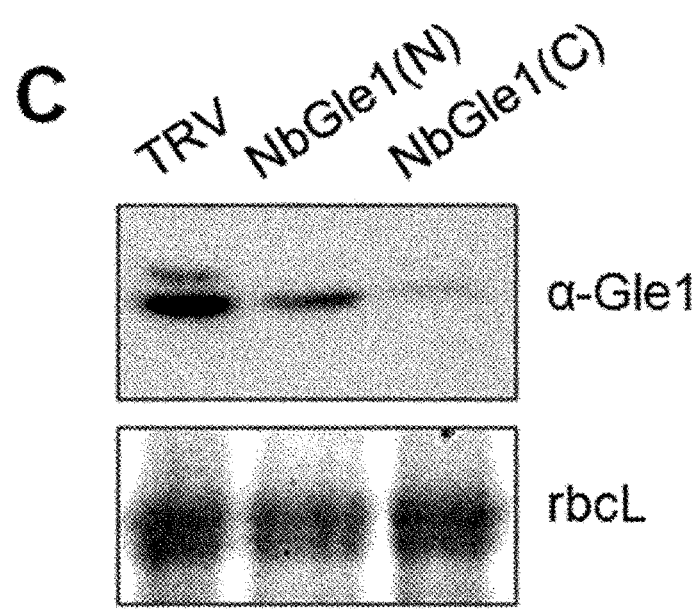

[FIG. 11D]
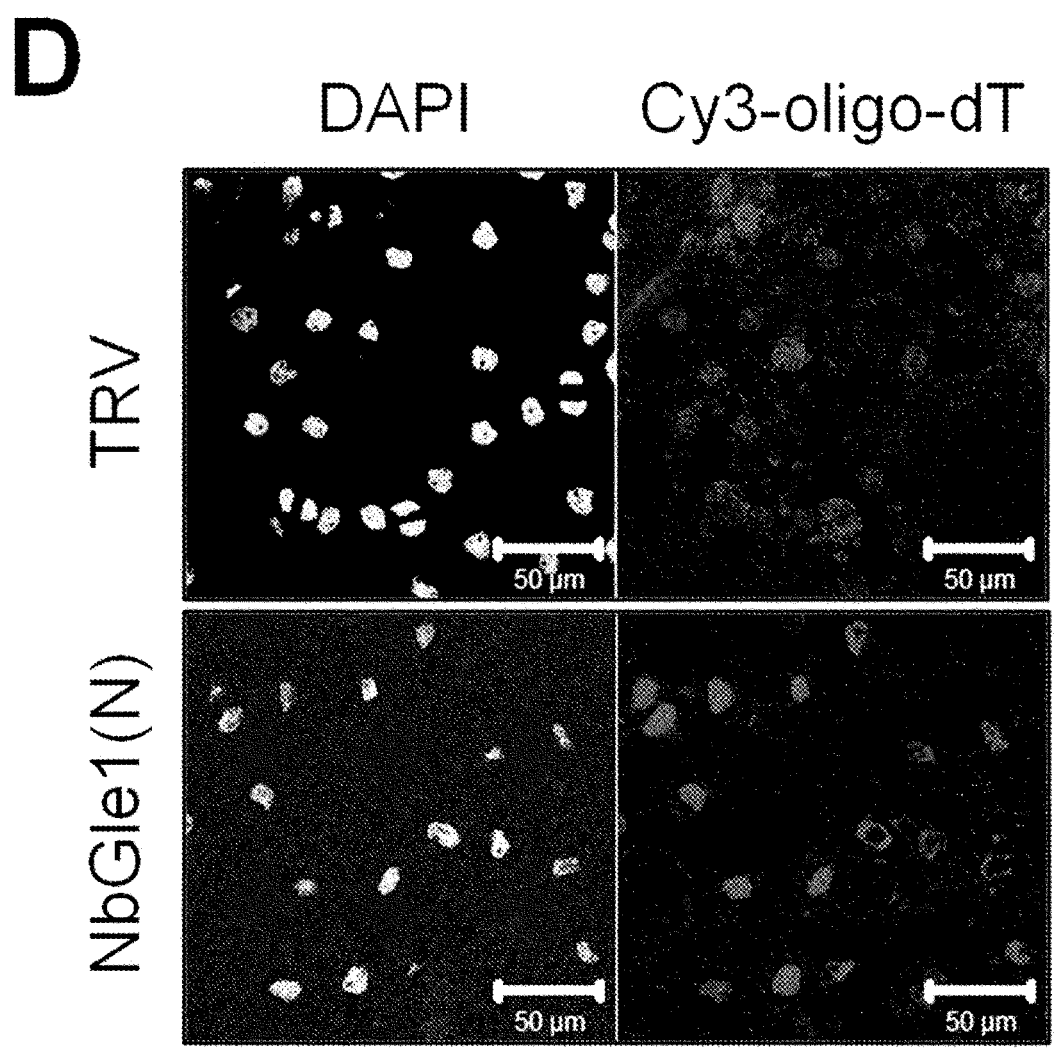

[FIG. 12]
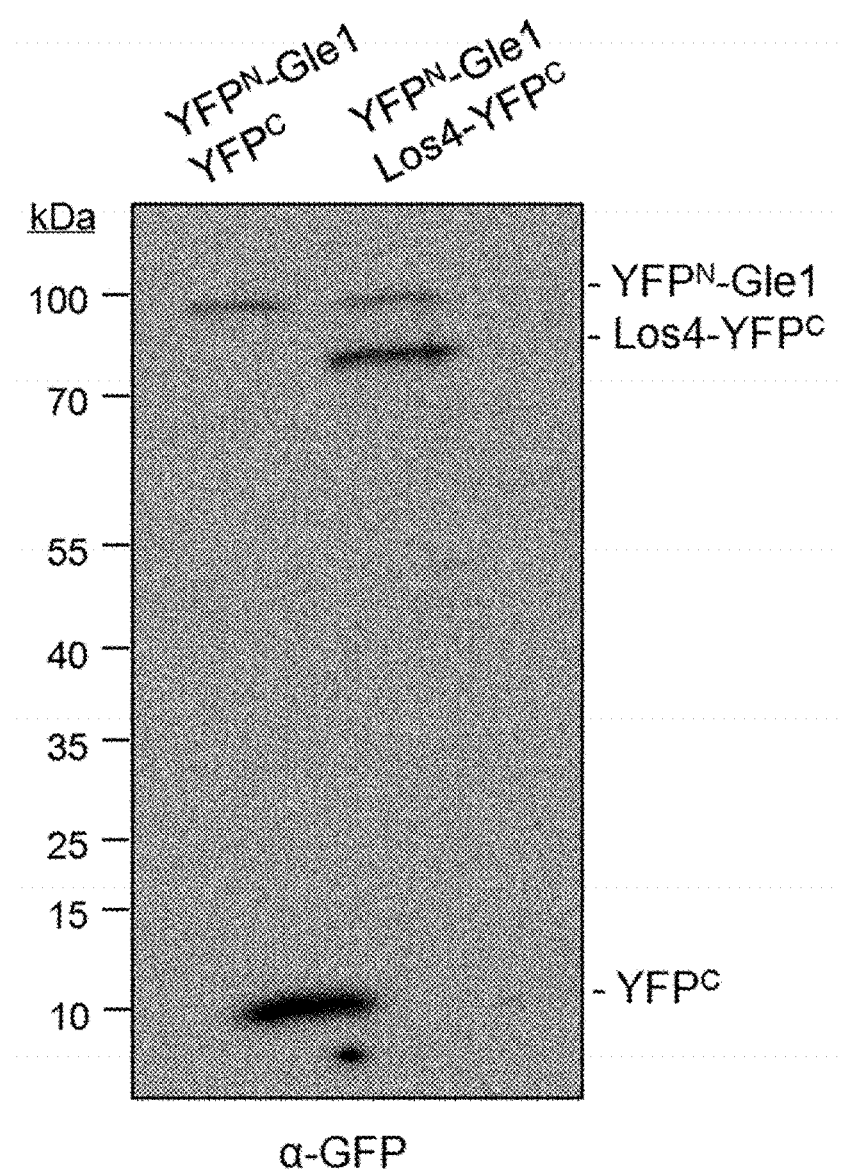

[FIG. 13A]
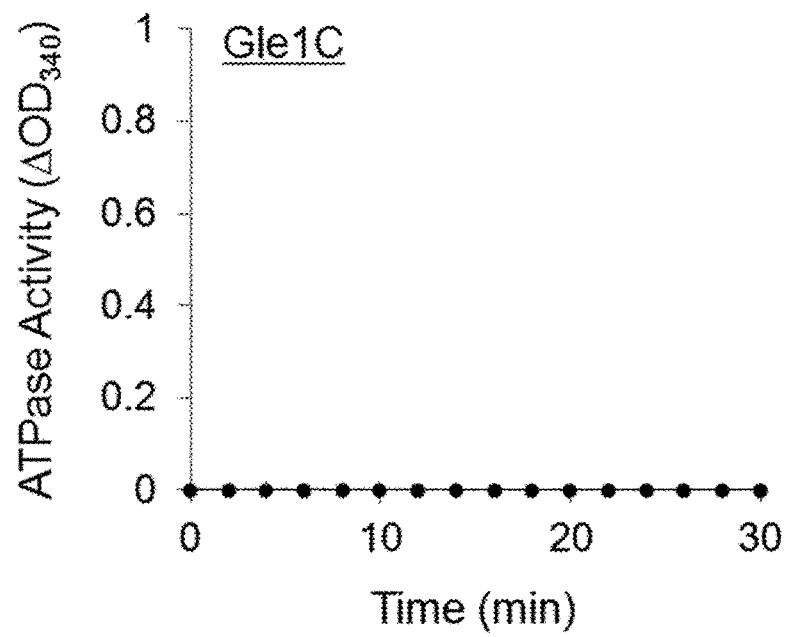
[FIG. 13B]
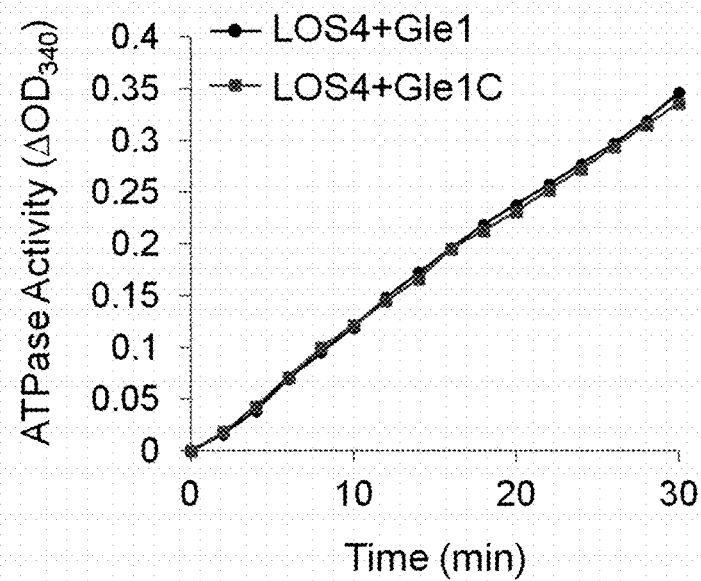

[FIG. 14]
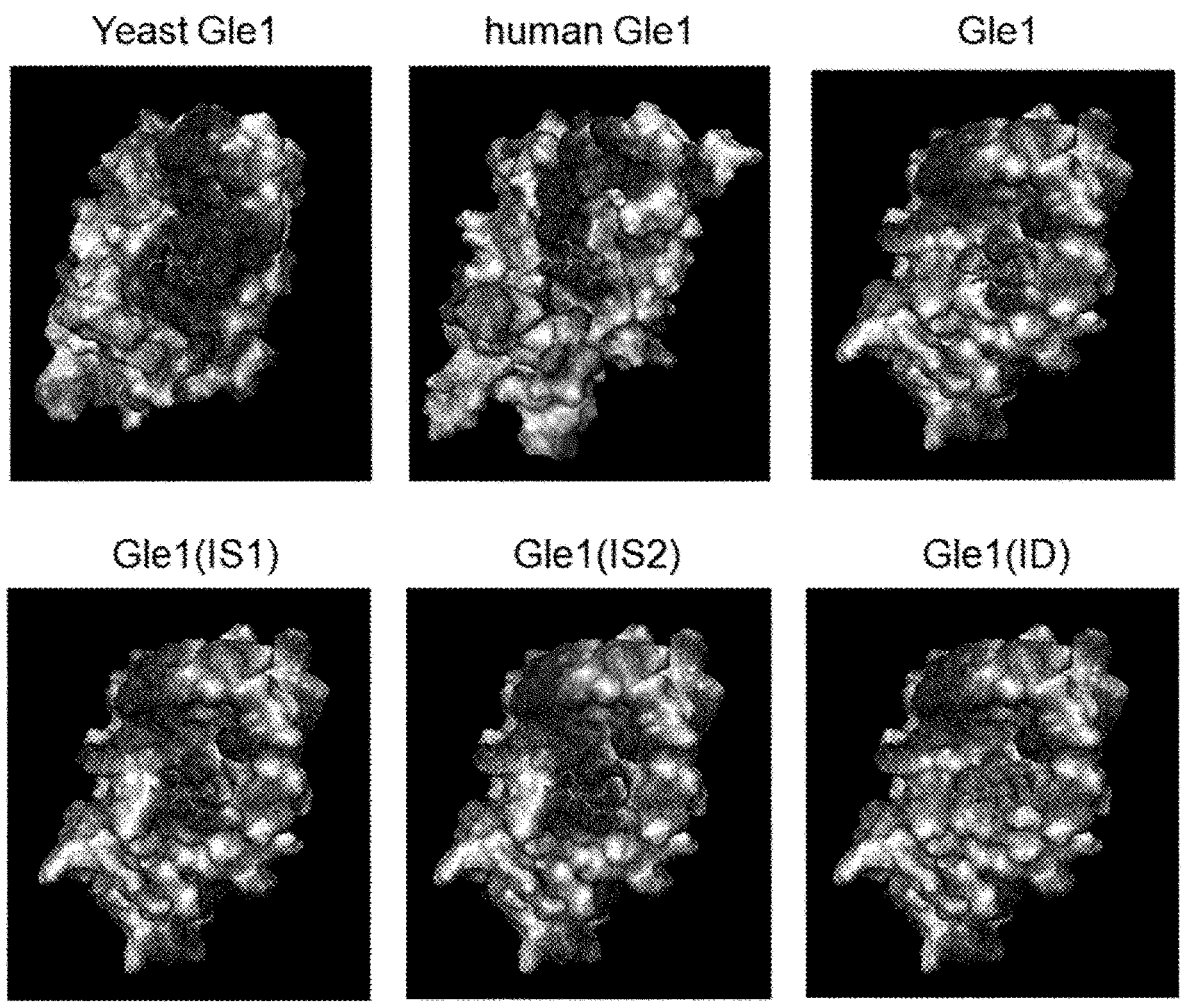

[FIG. 15]

| | | | | |
|---|---|---|---|---|
| Fungus | Sc | FMARLVKKCFVIG |
| | Ca | LNARFIKKCFYIG |
| Vertebrate | Hs | LLAHLHKKCFYSVE |
| | Mm | LLAHLHKKCFYSVE |
| | Dr | LLAHLHKKCFYAVE |
| | Bt | LLAHLHKKCFYSVE |
| Dicot | At | LLAEFHRACIYTVE |
| | Vv | LLAELHRVCIYTVE |
| | Pt1 | LLAEFHRACIYTVE |
| | Gm | LLAELHRACIYTVE |
| | Nb | LIGELNKVCIYAVE |
| | Rc | LLAEFHRGCIYTVE |
| Monocot | Os | LLAEFHRVCMYTVE |
| | Zm | LLAEFNRVCIYTVE |
| | Hv | LLAEFNKVCMYTVE |
| | Ta | LLAEFNKVCMYTVE |
| | Sb | LLAEFNRVCIYTVE |
| | Bd | LLAEFHKVCVYTVE |
| Gymnosperm | Pt2 | VLAELHKSCIFTVE |

[FIG. 16]
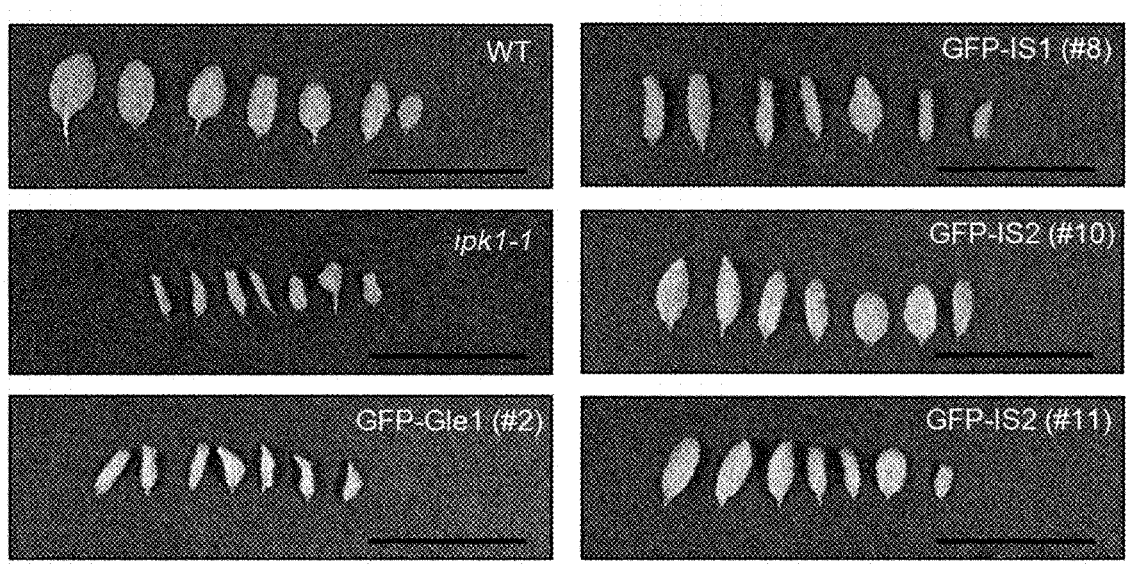

[FIG. 17]
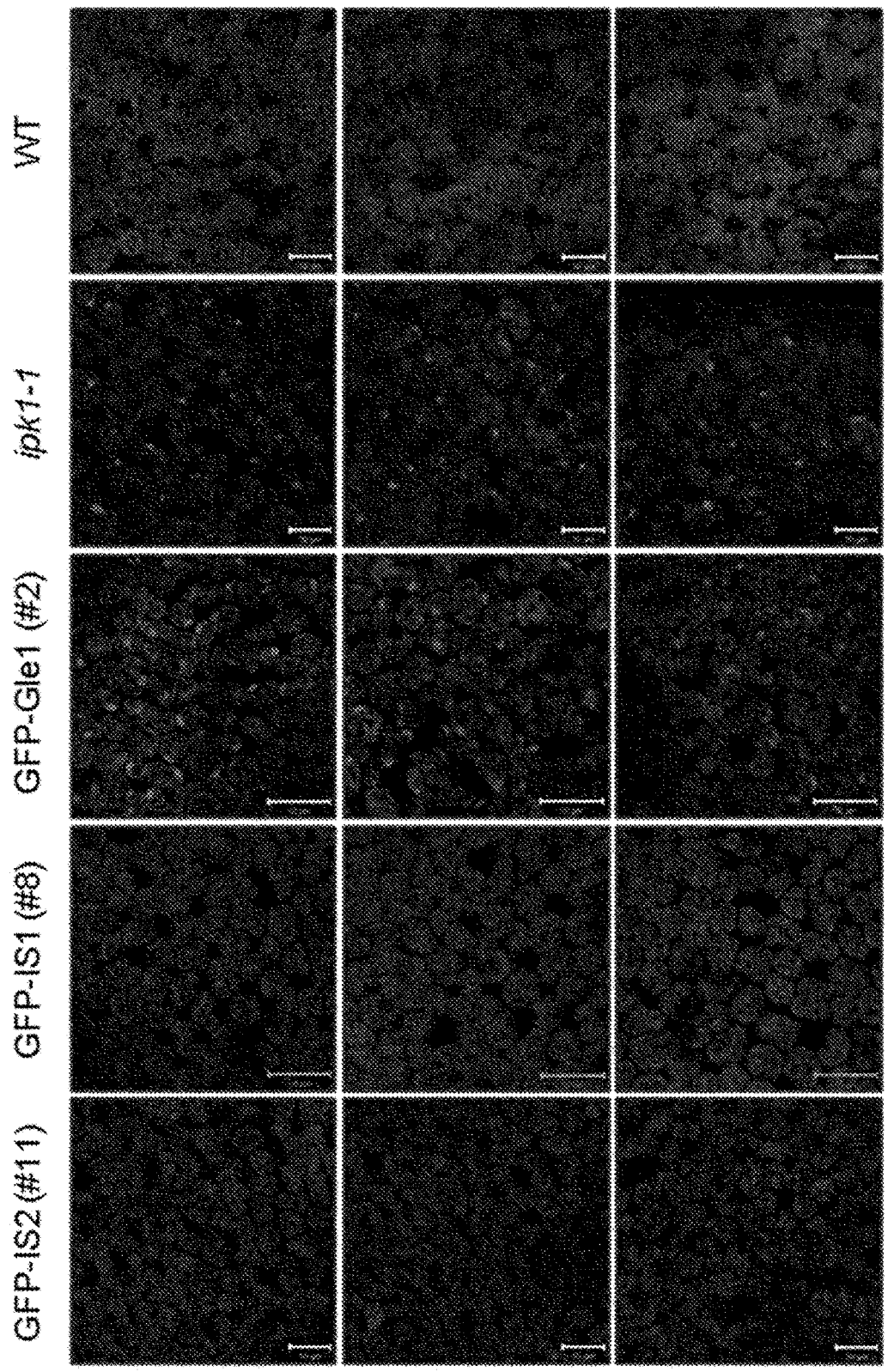

[FIG. 18A]
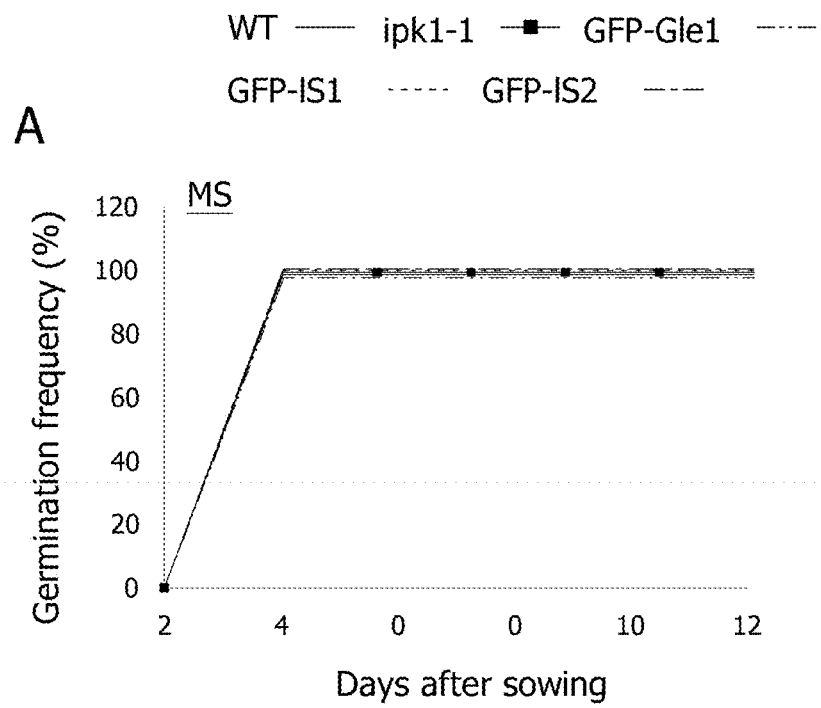
[FIG. 18B]
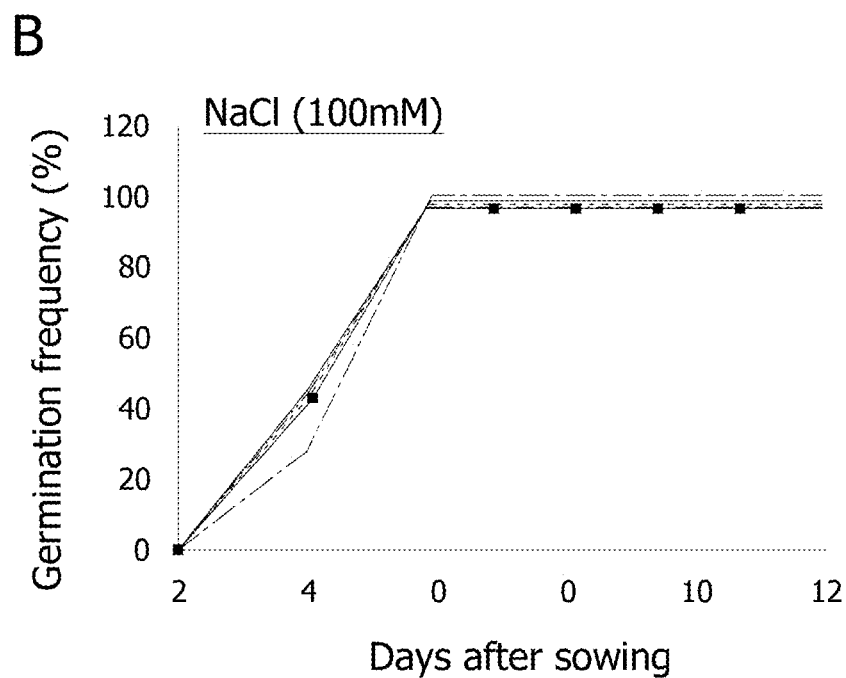

[FIG. 18C]
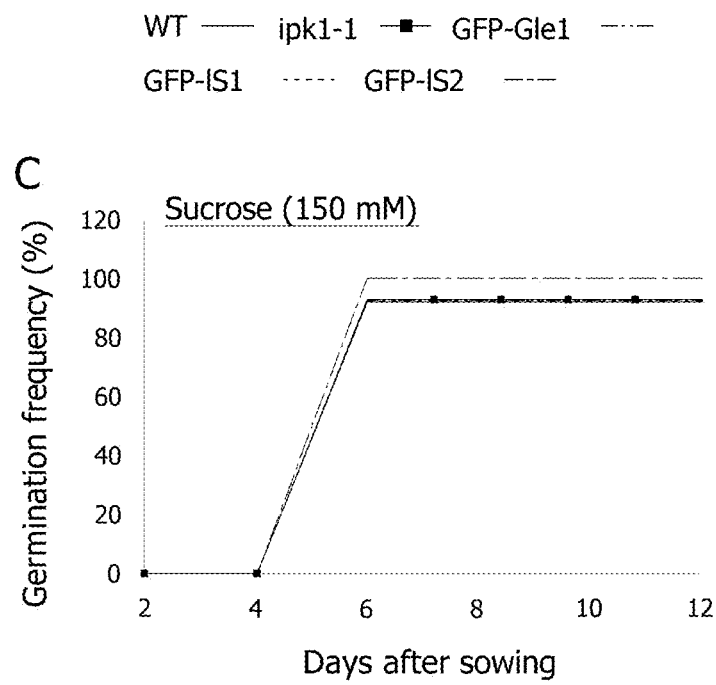
[FIG. 18D]
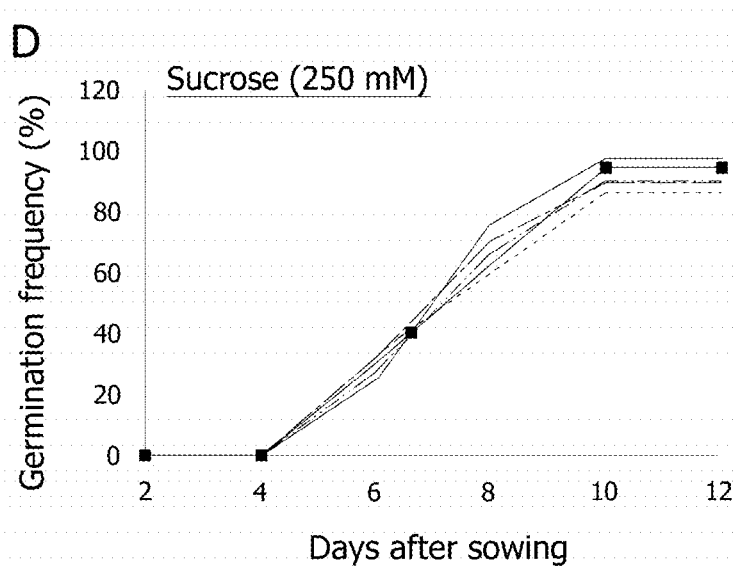

[FIG. 18E]
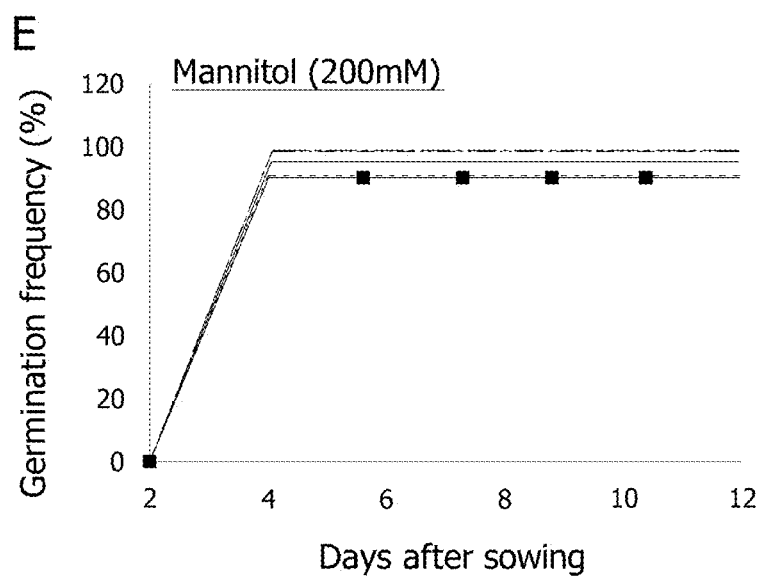
[FIG. 18F]
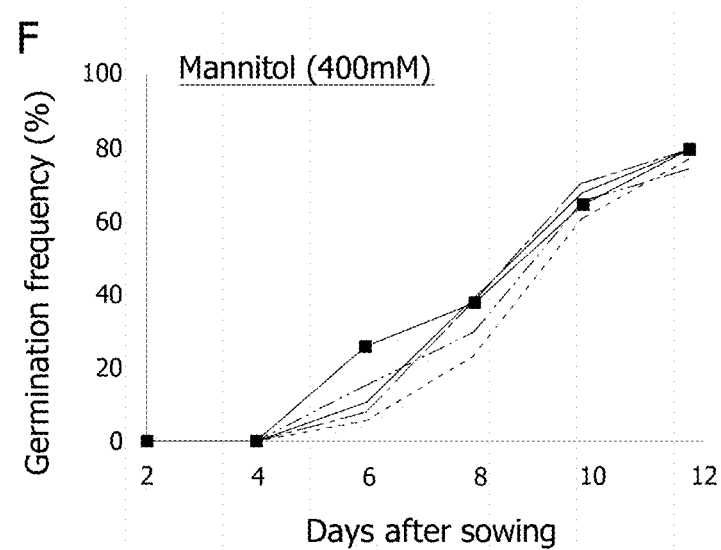

[FIG. 19]
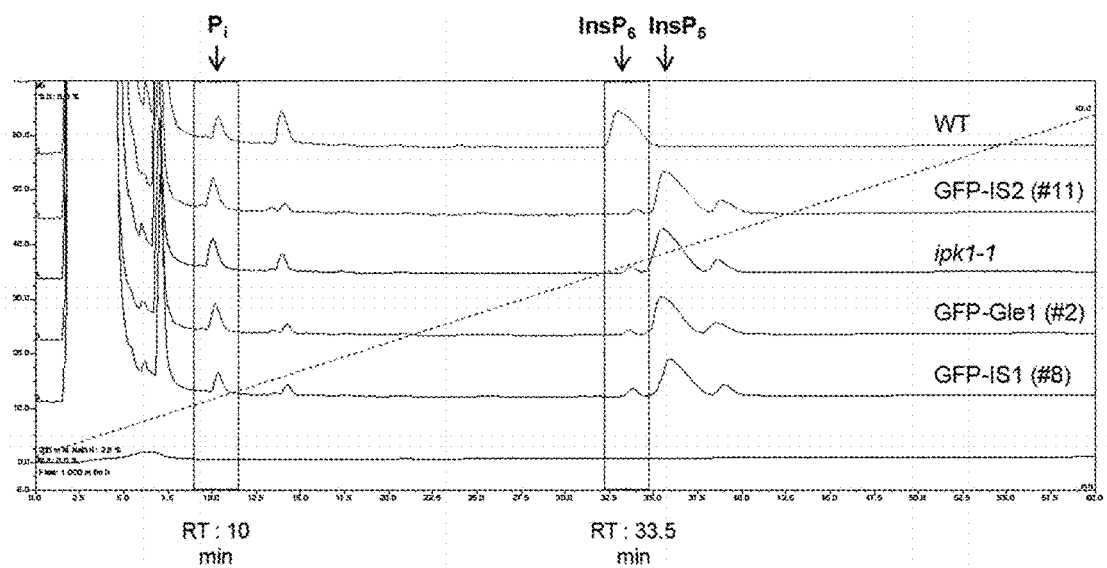

SEQUENCE LISTING

```
<160> NUMBER OF SEQ ID NOS: 57

<210> SEQ ID NO 1
<211> LENGTH: 1836
<212> TYPE: DNA
<213> ORGANISM: Arabidopsis thaliana
<220> FEATURE:
<221> NAME/KEY: misc_feature
<223> OTHER INFORMATION: Gle1 gene of Arabidopsis thaliana

<400> SEQUENCE: 1
atggggattg ttttggaacc tccttgtcct aaaagtgttg atgggattag cattgatcct      60
gagcctaatt ggaatttcga gagtttggtc gctgagattt cttctgttga aaagaagctc     120
aatggcttct caatgtatcc tcagccaatt actaacacaa ccttacggat gggaaggaga     180
ggtggaggat ttgtaatgca tgtctcagaa gatgagatgg agagtgacga aggtgaagag     240
agtgatgatg aggaagaaga agaagatcat agtcaaatct gtacagcggg aaaacgtttt     300
gcctgtgatg agctttactt gagtgatgaa tctgatgaag agtttgatca tgaacctgag     360
tatatgatga ataagttggg tctggctgag agtgccctat atgaggttat caacgaccac     420
caaaccgaaa tcaaggacga cattaggaat caagtatcag ttgttgaaac agaaataatg     480
aatgagattg aaacgtctct ctctgccata gcccgggttg aaaaagtacag tgagactcgg     540
```

```
aaagaagttg aacggaaact tgatcttcaa tatcagcgaa agttgctga agcacttgat      600 acccatctga ctgcagtcca acgcgaacat aaaattaaat cgcaaataga agaaagaaag    660
ataaggagcg aggaagctca ggaggaggcc aggaggaagg aaagggctca tcaagaagag    720
aaaatacgtc aagaaaaagc tcgcgcagag gctcaaatgc tagcaaaaat cagagctgaa    780
gaagaaaaga aagaagttga gagaaaggca gccagagaag tagctgaaaa agaagtagca    840
gatcgcaaag ctgccgaaca aaaacttgcg gaacagaagg ctgtgataga gagtgttacg    900
gggagttcag ctacatcaaa tgctcaagct ggggtaatt caatccgagc tgcagaaagt     960
gctttgatat ggagaaccca cagattgaaa aagctcgaag aactagaaac aacgaaccaa   1020
tcgcttaagt cacgttcaaa tgaaaacttt agcagttttg agaagcatat tggaagagtg   1080
ataaggcaaa taagtgggac aaaggatagt gtaagtggga aaatcaatga tattgtgaaa   1140
atatttaaag accctcgttg tccggtatcc ataagtattg cagcttttgc aaagaagatg   1200
gtcaccacta aggaaaaacc aaaccctttt gcatgcagct atgtcattgt ttacatcaac   1260
tcacagtttc cccaagttat ggatattctt ctcgcggaat ccacaaaagc ttgcatttac   1320
actgtcccaa agcatattgt aaactcacag tcagcttggg attcagacgc atatgaacgc   1380
ctagattcta taatgaggct ctacggtgca cttgttcaga ccgatatccg cgttggcaat   1440
gctactaacg ttcatgggat agaacatgga tgggcttggt tagcccggtt ccttaacaaa   1500
atcccagcca acagagccac tgcgacagcc ttgaactcct ttctccagac ggctgggttt   1560
ggtcttcatc agaggtacaa atctcagttt ctgaaggttg tgaatgttgt gagagagcat   1620
ttcttgcaga aattgcgggc gaagaaggac acgtcggatc tacttgtgat catagccgaa   1680
atcacagcgt acttagatga ccggatgtat ctcaaggaac ctgaaggaag agctatgaag   1740
acgactagta ccttgtcctc tgaacttact gctgaattaa atcagccgaa ctacaatcag   1800
aattaccaga ggaatgatta cagaaactac tattga                             1836
```

<210> SEQ ID NO 2
<211> LENGTH: 611
<212> TYPE: PRT
<213> ORGANISM: Arabidopsis thaliana
<220> FEATURE:
<221> NAME/KEY: misc_feature
<223> OTHER INFORMATION: Gle1 protein of Arabidopsis thaliana

<400> SEQUENCE: 2

```
Met Gly Ile Val Leu Glu Pro Pro Cys Pro Lys Ser Val Asp Gly Ile
1               5                  10                  15

Ser Ile Asp Pro Glu Pro Asn Trp Asn Phe Glu Ser Leu Val Ala Glu
            20                  25                  30

Ile Ala Ser Val Glu Lys Lys Leu Asn Gly Phe Ser Met Tyr Pro Gln
        35                  40                  45

Pro Ile Thr Asn Thr Thr Leu Arg Met Gly Arg Arg Gly Gly Gly Phe
    50                  55                  60

Val Met His Val Ser Glu Asp Glu Met Glu Ser Asp Glu Gly Glu Glu
65                  70                  75                  80

Ser Asp Asp Glu Glu Glu Glu Glu Asp His Ser Gln Ile Cys Thr Ala
                85                  90                  95

Gly Lys Arg Phe Ala Cys Asp Glu Leu Tyr Leu Ser Asp Glu Ser Asp
            100                 105                 110

Glu Glu Phe Asp His Glu Pro Glu Tyr Met Met Asn Lys Leu Gly Leu
        115                 120                 125
```

```
Ala Glu Ser Ala Leu Tyr Glu Val Ile Asn Asp His Gln Thr Glu Ile
130                 135                 140

Lys Asp Asp Ile Arg Asn Gln Val Ser Val Glu Thr Glu Ile Met
145                 150                 155                 160

Asn Glu Ile Glu Thr Ser Leu Ser Ala Ile Ala Arg Val Glu Lys Tyr
                165                 170                 175

Ser Glu Thr Arg Lys Glu Val Glu Arg Lys Leu Asp Leu Gln Tyr Gln
                180                 185                 190

Arg Lys Val Ala Glu Ala Leu Asp Thr His Leu Thr Ala Val Gln Arg
            195                 200                 205

Glu His Lys Ile Lys Ser Gln Ile Glu Glu Arg Lys Ile Arg Ser Glu
210                 215                 220

Glu Ala Gln Glu Glu Ala Arg Arg Lys Glu Arg Ala His Gln Glu Glu
225                 230                 235                 240

Lys Ile Arg Gln Glu Lys Ala Arg Ala Glu Ala Gln Met Leu Ala Lys
                245                 250                 255

Ile Arg Ala Glu Glu Glu Lys Lys Glu Val Glu Arg Lys Ala Ala Arg
            260                 265                 270

Glu Val Ala Glu Lys Glu Val Ala Asp Arg Lys Ala Ala Glu Gln Lys
        275                 280                 285

Leu Ala Glu Gln Lys Ala Val Ile Glu Ser Val Thr Gly Ser Ser Ala
290                 295                 300

Thr Ser Asn Ala Gln Ala Gly Gly Asn Ser Ile Arg Ala Ala Glu Ser
305                 310                 315                 320

Ala Leu Ile Leu Glu Asn His Arg Leu Lys Lys Leu Glu Glu Leu Glu
                325                 330                 335

Thr Thr Asn Gln Ser Leu Lys Ser Arg Ser Asn Glu Asn Phe Ser Ser
            340                 345                 350

Phe Glu Lys His Ile Gly Arg Val Ile Arg Gln Ile Ser Gly Thr Lys
        355                 360                 365

Asp Ser Val Ser Gly Lys Ile Asn Asp Ile Val Lys Ile Phe Lys Asp
370                 375                 380

Pro Arg Cys Pro Val Ser Ile Ser Ile Ala Ala Phe Ala Lys Lys Met
385                 390                 395                 400

Val Thr Thr Lys Glu Lys Pro Asn Pro Phe Ala Cys Ser Tyr Val Ile
                405                 410                 415

Val Tyr Ile Asn Ser Gln Phe Pro Gln Val Met Asp Ile Leu Leu Ala
            420                 425                 430

Glu Phe His Lys Ala Cys Ile Tyr Thr Val Pro Lys His Ile Val Asn
        435                 440                 445

Ser Gln Ser Ala Trp Asp Ser Asp Ala Tyr Glu Arg Leu Asp Ser Ile
450                 455                 460

Met Arg Leu Tyr Gly Ala Leu Val Gln Thr Asp Ile Arg Val Gly Asn
465                 470                 475                 480

Ala Thr Asn Val His Gly Ile Glu His Gly Trp Ala Trp Leu Ala Arg
                485                 490                 495

Phe Leu Asn Lys Ile Pro Ala Asn Arg Ala Thr Ala Thr Ala Leu Asn
            500                 505                 510

Ser Phe Leu Gln Thr Ala Gly Phe Gly Leu His Gln Arg Tyr Lys Ser
        515                 520                 525

Gln Phe Leu Lys Val Val Asn Val Val Arg Glu His Phe Leu Gln Lys
530                 535                 540

Leu Arg Ala Lys Lys Asp Thr Ser Asp Leu Leu Val Ile Ile Ala Glu
```

```
                 545                 550                 555                 560
Ile Thr Ala Tyr Leu Asp Asp Arg Met Tyr Leu Lys Glu Pro Glu Gly
                     565                 570                 575

Arg Ala Met Lys Thr Thr Ser Thr Leu Ser Ser Glu Leu Thr Ala Glu
                 580                 585                 590

Leu Asn Gln Pro Asn Tyr Asn Gln Asn Tyr Gln Arg Asn Asp Tyr Arg
            595                 600                 605

Asn Tyr Tyr
    610

<210> SEQ ID NO 3
<211> LENGTH: 19
<212> TYPE: DNA
<213> ORGANISM: Artificial
<220> FEATURE:
<223> OTHER INFORMATION: Forward primer for amplifying of 356 bp Gle1
      cDNA fragment

<400> SEQUENCE: 3
atggggattg ttttggaac                                                  19

<210> SEQ ID NO 4
<211> LENGTH: 22
<212> TYPE: DNA
<213> ORGANISM: Artificial
<220> FEATURE:
<223> OTHER INFORMATION: Reverse primer for amplifying of 356 bp Gle1
      cDNA fragment

<400> SEQUENCE: 4
ggttcatgat caaactcttc at                                              22

<210> SEQ ID NO 5
<211> LENGTH: 21
<212> TYPE: DNA
<213> ORGANISM: Artificial
<220> FEATURE:
<223> OTHER INFORMATION: Forward primer for amplifying of 330 bp Gle1
      cDNA fragment

<400> SEQUENCE: 5
cacaaagctt gcatttacac t                                               21

<210> SEQ ID NO 6
<211> LENGTH: 21
<212> TYPE: DNA
<213> ORGANISM: Artificial
<220> FEATURE:
<223> OTHER INFORMATION: Reverse primer for amplifying of 330 bp Gle1
      cDNA fragment

<400> SEQUENCE: 6
atgctctctc acaacattca c                                               21

<210> SEQ ID NO 7
<211> LENGTH: 20
<212> TYPE: DNA
<213> ORGANISM: Artificial
<220> FEATURE:
<223> OTHER INFORMATION: Forward primer for detecting of Gle1 transcript
      in RNAi-Gle1(N)

<400> SEQUENCE: 7
catggatggg cttggttagc                                                 20
```

```
<210> SEQ ID NO 8
<211> LENGTH: 19
<212> TYPE: DNA
<213> ORGANISM: Artificial
<220> FEATURE:
<223> OTHER INFORMATION: Reverse primer for detecting of Gle1 transcript
      in RNAi-Gle1(N)

<400> SEQUENCE: 8
tgtcgcagtg gctctgttg                                                    19

<210> SEQ ID NO 9
<211> LENGTH: 24
<212> TYPE: DNA
<213> ORGANISM: Artificial
<220> FEATURE:
<223> OTHER INFORMATION: Forward primer for detecting of Gle1 transcript
      in RNAi-Gle1(C)

<400> SEQUENCE: 9
tcagccaatt actaacacaa cctt                                              24

<210> SEQ ID NO 10
<211> LENGTH: 22
<212> TYPE: DNA
<213> ORGANISM: Artificial
<220> FEATURE:
<223> OTHER INFORMATION: Reverse primer for detecting of Gle1 transcript
      in RNAi-Gle1(C)

<400> SEQUENCE: 10
gacatgcatt acaaatcctc ca                                                22

<210> SEQ ID NO 11
<211> LENGTH: 21
<212> TYPE: DNA
<213> ORGANISM: Artificial
<220> FEATURE:
<223> OTHER INFORMATION: Forward primer for detecting of UBC10
      transcript

<400> SEQUENCE: 11
atgggtcctt cagagagtcc t                                                 21

<210> SEQ ID NO 12
<211> LENGTH: 21
<212> TYPE: DNA
<213> ORGANISM: Artificial
<220> FEATURE:
<223> OTHER INFORMATION: Reverse primer for detecting of UBC10
      transcript

<400> SEQUENCE: 12
tggaacacct tggtcctaaa g                                                 21

<210> SEQ ID NO 13
<211> LENGTH: 14
<212> TYPE: PRT
<213> ORGANISM: Glycine max
<220> FEATURE:
<221> NAME/KEY: misc_feature
<223> OTHER INFORMATION: Gle1-InsP6 binding site of Glycine max

<400> SEQUENCE: 13

Leu Leu Ala Glu Leu His Arg Ala Cys Ile Tyr Thr Val Pro
1               5                   10
```

```
<210> SEQ ID NO 14
<211> LENGTH: 14
<212> TYPE: PRT
<213> ORGANISM: Oryza sativa
<220> FEATURE:
<221> NAME/KEY: misc_feature
<223> OTHER INFORMATION: Gle1-InsP6 binding site of Oryza sativa

<400> SEQUENCE: 14

Leu Leu Ala Glu Phe His Arg Val Cys Met Tyr Thr Val Pro
1               5                   10

<210> SEQ ID NO 15
<211> LENGTH: 14
<212> TYPE: PRT
<213> ORGANISM: Zea mays
<220> FEATURE:
<221> NAME/KEY: misc_feature
<223> OTHER INFORMATION: Gle1-InsP6 binding site of Zea mays

<400> SEQUENCE: 15

Leu Leu Ala Glu Phe Asn Arg Val Cys Ile Tyr Thr Val Pro
1               5                   10

<210> SEQ ID NO 16
<211> LENGTH: 14
<212> TYPE: PRT
<213> ORGANISM: Hordeum vulgare
<220> FEATURE:
<221> NAME/KEY: misc_feature
<223> OTHER INFORMATION: Gle1-InsP6 binding site of Hordeum vulgare

<400> SEQUENCE: 16

Leu Leu Ala Glu Phe Asn Lys Val Cys Met Tyr Thr Val Pro
1               5                   10

<210> SEQ ID NO 17
<211> LENGTH: 14
<212> TYPE: PRT
<213> ORGANISM: Triticum aestivum
<220> FEATURE:
<221> NAME/KEY: misc_feature
<223> OTHER INFORMATION: Gle1-InsP6 binding site of Triticum aestivum

<400> SEQUENCE: 17

Leu Leu Ala Glu Phe Asn Lys Val Cys Met Tyr Thr Val Pro
1               5                   10

<210> SEQ ID NO 18
<211> LENGTH: 14
<212> TYPE: PRT
<213> ORGANISM: Artificial
<220> FEATURE:
<223> OTHER INFORMATION: Phytic acid-binding pocket which is comprised
      in a Gle1 protein variant
<220> FEATURE:
<221> NAME/KEY: misc_feature
<222> LOCATION: (5)..(5)
<223> OTHER INFORMATION: X (5th amino acid) is Leu or Phe
<220> FEATURE:
<221> NAME/KEY: misc_feature
<222> LOCATION: (6)..(6)
<223> OTHER INFORMATION: X (6th amino acid) is His or Asn
<220> FEATURE:
<221> NAME/KEY: misc_feature
<222> LOCATION: (7)..(7)
<223> OTHER INFORMATION: X (7th amino acid) is Lys or Arg
<220> FEATURE:
<221> NAME/KEY: misc_feature
<222> LOCATION: (8)..(8)
```

```
<223> OTHER INFORMATION: X (8th amino acid) is Ala or Val
<220> FEATURE:
<221> NAME/KEY: misc_feature
<222> LOCATION: (10)..(10)
<223> OTHER INFORMATION: X (10th amino acid) is Ile or Met

<400> SEQUENCE: 18

Leu Leu Ala Glu Xaa Xaa Xaa Cys Xaa Tyr Thr Val Pro
1               5                   10

<210> SEQ ID NO 19
<211> LENGTH: 14
<212> TYPE: PRT
<213> ORGANISM: Arabidopsis thaliana

<400> SEQUENCE: 19

Glu Glu Ala Arg Arg Lys Glu Arg Ala His Gln Glu Glu Lys
1               5                   10

<210> SEQ ID NO 20
<211> LENGTH: 10
<212> TYPE: PRT
<213> ORGANISM: Arabidopsis thaliana

<400> SEQUENCE: 20

Met Arg Leu Tyr Gly Ala Leu Val Gln Thr
1               5                   10

<210> SEQ ID NO 21
<211> LENGTH: 9
<212> TYPE: PRT
<213> ORGANISM: Arabidopsis thaliana
<220> FEATURE:
<221> NAME/KEY: misc_feature
<223> OTHER INFORMATION: key residues of an InsP6-binding pocket of
      Arabidopsis thaliana Gle1 (431-439 of Gle 1)

<400> SEQUENCE: 21

Leu Ala Glu Phe His Lys Ala Cys Ile
1               5

<210> SEQ ID NO 22
<211> LENGTH: 9
<212> TYPE: PRT
<213> ORGANISM: Artificial
<220> FEATURE:
<223> OTHER INFORMATION: key residues of an InsP6-binding pocket of Gle1
      variants (431-439 of Gle 1 variants; IS1)

<400> SEQUENCE: 22

Leu Ala Glu Phe His Lys Lys Cys Ile
1               5

<210> SEQ ID NO 23
<211> LENGTH: 9
<212> TYPE: PRT
<213> ORGANISM: Artificial
<220> FEATURE:
<223> OTHER INFORMATION: key residues of an InsP6-binding pocket of Gle1
      variants (431-439 of Gle 1 variants; IS2)

<400> SEQUENCE: 23

Leu Ala Lys Phe His Lys Lys Cys Ile
1               5

<210> SEQ ID NO 24
<211> LENGTH: 9
```

-continued

```
<212> TYPE: PRT
<213> ORGANISM: Artificial
<220> FEATURE:
<223> OTHER INFORMATION: key residues of an InsP6-binding pocket of Gle1
      variants (431-439 of Gle 1 variants; ID)

<400> SEQUENCE: 24

Leu Ala Glu Phe His Ala Ala Cys Ile
1               5

<210> SEQ ID NO 25
<211> LENGTH: 246
<212> TYPE: PRT
<213> ORGANISM: Saccharomyces cerevisiae
<220> FEATURE:
<221> NAME/KEY: misc_feature
<223> OTHER INFORMATION: Gle1 domains of Saccharomyces cerevisiae (Sc)

<400> SEQUENCE: 25

Tyr Lys Asp Lys Ile Ala Gln Ile Lys Gln Asp Ile Val Leu Pro Ile
1               5                   10                  15

Lys Lys Ala Asp Val Asn Val Arg Asn Leu Leu Ser Arg His Lys Arg
            20                  25                  30

Lys Ile Asn Pro Lys Phe Gly Gln Leu Thr Asn Ser Asn Gln Gln Leu
        35                  40                  45

Phe Lys Ile Gln Asn Glu Leu Thr Gln Leu Ile Asn Asp Thr Lys Gly
    50                  55                  60

Asp Ser Leu Ala Tyr His Trp Ile Leu Asn Phe Ile Ala Lys Ala Val
65                  70                  75                  80

Val His Gln Ala Glu Thr Glu Val Arg Val Lys Pro Glu Ser Ala Leu
                85                  90                  95

Pro Leu Gly Lys Leu Thr Leu Tyr Leu Leu Val Gln Phe Pro Glu Leu
            100                 105                 110

Gln Glu Leu Phe Met Ala Arg Leu Val Lys Lys Cys Pro Phe Val Ile
        115                 120                 125

Gly Phe Thr Cys Glu Ile Asp Thr Glu Lys Gly Arg Gln Asn Met Gly
    130                 135                 140

Trp Lys Arg Asn Asn Glu Asn Lys Trp Glu Asp Asn Thr Ser Tyr Asp
145                 150                 155                 160

Glu Arg Met Gly Gly Ile Leu Ser Leu Phe Ala Ile Ile Thr Arg Leu
                165                 170                 175

Gln Leu Pro Gln Glu Phe Ile Thr Thr Thr Ser His Pro Phe Pro Ile
            180                 185                 190

Ala Leu Ser Trp His Ile Leu Ala Arg Ile Cys Asn Thr Pro Leu Asn
        195                 200                 205

Leu Ile Thr Asn Thr His Phe Val Ile Leu Gly Ser Trp Trp Asp Ala
    210                 215                 220

Ala Ala Val Gln Phe Leu Gln Ala Tyr Gly Asn Gln Ala Ser Lys Leu
225                 230                 235                 240

Leu Ile Leu Ile Gly Glu
                245

<210> SEQ ID NO 26
<211> LENGTH: 182
<212> TYPE: PRT
<213> ORGANISM: Candida albicans
<220> FEATURE:
<221> NAME/KEY: misc_feature
<223> OTHER INFORMATION: Gle1 domains of Candida albicans SC5314 (Ca)
```

```
<400> SEQUENCE: 26

Ser Thr Glu Val Ile Gly Met Ile Lys Ala Val Glu Thr Asn Ala Leu
1               5                   10                  15

Val Phe Lys Trp Val Leu Asn Phe Thr Ala Lys Ala Ile Ile Asp Gln
            20                  25                  30

Ala Glu Thr Glu Val Ile Val Arg Pro Asn Ser Ala Val Pro Leu Ala
        35                  40                  45

Lys Leu Ala Tyr Ala Ile Leu Gln Ala Ile Pro Asp Phe Glu Tyr Tyr
    50                  55                  60

Leu Asn Ala Arg Phe Ile Lys Lys Cys Pro Tyr Ile Ile Gly Tyr Asn
65                  70                  75                  80

Cys Ser Ile Asp Ser Glu Gly Arg Glu Arg Met Gly Trp Lys Arg
                85                  90                  95

Pro Asp Gly Ser Lys Trp Glu Glu Thr Lys Tyr Asp Glu Arg Met
            100                 105                 110

Gly Gly Ile Val Ser Val Trp Ala Ala Met Thr Thr Ile Thr Asn His
            115                 120                 125

Gly Ser Gln Lys Ser Leu Tyr Ser Phe Glu Ala Ser Trp Gln Phe Leu
130                 135                 140

Ala Arg Thr Ala Asn Leu Gln Thr Ser Met Leu Val Asn Thr His Phe
145                 150                 155                 160

Thr Ile Leu Gly Asn Trp Trp Glu Ala Ala Gly Ala Ser Phe Leu Gly
                165                 170                 175

Val Tyr Gly Asn Gln Ser
            180

<210> SEQ ID NO 27
<211> LENGTH: 253
<212> TYPE: PRT
<213> ORGANISM: Homo sapiens
<220> FEATURE:
<221> NAME/KEY: misc_feature
<223> OTHER INFORMATION: Gle1 domains of Homo sapiens (Hs)

<400> SEQUENCE: 27

Gln Cys Val Leu Thr Phe Glu Gly Leu Thr Asn Ser Lys Asp Ser Gln
1               5                   10                  15

Ala Lys Lys Ile Lys Met Asp Leu Gln Lys Ala Ala Thr Ile Pro Val
            20                  25                  30

Ser Gln Ile Ser Thr Ile Ala Gly Ser Lys Leu Lys Glu Ile Phe Asp
        35                  40                  45

Lys Ile His Ser Leu Leu Ser Gly Lys Pro Val Gln Ser Gly Gly Arg
    50                  55                  60

Ser Val Ser Val Thr Leu Asn Pro Gln Gly Leu Asp Phe Val Gln Tyr
65                  70                  75                  80

Lys Leu Ala Glu Lys Phe Val Lys Gln Gly Glu Glu Val Ala Ser
                85                  90                  95

His His Glu Ala Ala Phe Pro Ile Ala Val Val Ala Ser Gly Ile Trp
            100                 105                 110

Glu Leu His Pro Arg Val Gly Asp Leu Ile Leu Ala His Leu His Lys
            115                 120                 125

Lys Cys Pro Tyr Ser Val Pro Phe Tyr Pro Thr Phe Lys Glu Gly Met
        130                 135                 140

Ala Leu Glu Asp Tyr Gln Arg Met Leu Gly Tyr Gln Val Lys Asp Ser
145                 150                 155                 160
```

-continued

```
Lys Val Glu Gln Gln Asp Asn Phe Leu Lys Arg Met Ser Gly Met Ile
            165                 170                 175

Arg Leu Tyr Ala Ala Ile Ile Gln Leu Arg Trp Pro Tyr Gly Asn Arg
        180                 185                 190

Gln Glu Ile His Pro His Gly Leu Asn His Gly Trp Arg Trp Leu Ala
    195                 200                 205

Gln Ile Leu Asn Met Glu Pro Leu Ser Asp Val Thr Ala Thr Leu Leu
210                 215                 220

Phe Asp Phe Leu Glu Val Cys Gly Asn Ala Leu Met Lys Gln Tyr Gln
225                 230                 235                 240

Val Gln Phe Trp Lys Met Leu Ile Leu Ile Lys Glu Asp
            245                 250
```

<210> SEQ ID NO 28
<211> LENGTH: 257
<212> TYPE: PRT
<213> ORGANISM: Mus musculus
<220> FEATURE:
<221> NAME/KEY: misc_feature
<223> OTHER INFORMATION: Gle1 domains of Mus musculus (Mm)

<400> SEQUENCE: 28

```
Asp Ala Ser Ala Lys Cys Val Leu Ala Phe Glu Asp Leu Thr Ser Ser
1               5                   10                  15

Lys Asp Ser Gln Thr Lys Lys Ile Lys Met Asp Leu Gln Lys Ala Ala
            20                  25                  30

Thr Ile Pro Val Ser Gln Ile Ser Thr Ile Ala Gly Ser Lys Leu Lys
        35                  40                  45

Glu Ile Phe Asp Lys Ile His Ser Leu Leu Ser Gly Lys Pro Val Gln
    50                  55                  60

Ser Gly Gly Arg Ser Val Ser Val Thr Leu Asn Pro Gln Gly Leu Asp
65                  70                  75                  80

Phe Val Gln Tyr Lys Leu Ala Glu Lys Phe Val Lys Gln Gly Glu Glu
                85                  90                  95

Glu Val Ala Ser His His Glu Ala Ala Phe Pro Ile Ala Val Val Ala
            100                 105                 110

Ser Gly Ile Trp Met Leu His Pro Lys Val Gly Asp Leu Ile Leu Ala
        115                 120                 125

His Leu His Lys Lys Cys Pro Tyr Ser Val Pro Phe Tyr Pro Ala Phe
    130                 135                 140

Lys Glu Gly Met Ala Leu Glu Asp Tyr Gln Arg Met Leu Gly Tyr Gln
145                 150                 155                 160

Val Thr Asp Ser Lys Val Glu Gln Gln Asp Asn Phe Leu Lys Arg Met
                165                 170                 175

Ser Gly Met Ile Arg Leu Tyr Ala Ala Ile Ile Gln Leu Gln Trp Pro
            180                 185                 190

Tyr Gly Asn Arg Gln Glu Ala His Pro His Gly Leu Asn His Gly Trp
        195                 200                 205

Arg Trp Leu Ala Gln Val Leu Asn Met Glu Pro Leu Ser Asp Val Thr
    210                 215                 220

Ala Thr Leu Leu Phe Asp Phe Leu Glu Val Cys Gly Asn Ala Leu Met
225                 230                 235                 240

Lys Gln Tyr Gln Val Gln Phe Trp Lys Met Ile Leu Leu Ile Lys Glu
                245                 250                 255

Asp
```

-continued

```
<210> SEQ ID NO 29
<211> LENGTH: 257
<212> TYPE: PRT
<213> ORGANISM: Danio rerio
<220> FEATURE:
<221> NAME/KEY: misc_feature
<223> OTHER INFORMATION: Gle1 domains of Danio rerio (Dr)

<400> SEQUENCE: 29

Gln Asp Leu Ala Asn Gln Cys Ala Gln Ala Phe Asp Asp Leu Asn Lys
1               5                   10                  15

Ala Lys Asp Thr Gln Thr Lys Lys Leu Lys Met Glu Leu Gln Lys Ala
            20                  25                  30

Ala Thr Thr Pro Val Ser Gln Ile Ala Asn Ser Ser Gly Ala Pro Leu
        35                  40                  45

Lys Glu Ala Phe Glu Lys Ile Asp Lys Leu Leu Ser Arg Arg Pro Val
    50                  55                  60

Thr Ser Ala Gly Lys Thr Val Ser Thr Ser Gln His Pro Gln Gly Leu
65                  70                  75                  80

Glu Phe Ala Ser Tyr Arg Leu Ala Glu Lys Phe Val Lys Gln Gly Glu
                85                  90                  95

Glu Glu Val Ala Ser Asn His Ser Ala Ala Phe Pro Ile Gly Ala Val
            100                 105                 110

Ala Ser Gly Ile Trp Glu Leu His Pro Lys Ile Gly Asp Leu Ile Leu
        115                 120                 125

Ala His Leu His Lys Lys Cys Pro Tyr Ala Val Pro His Tyr Pro Pro
    130                 135                 140

Met Glu Ser Gly Thr Ser Val Glu Asp Tyr Gln Lys Ile Leu Gly Tyr
145                 150                 155                 160

Arg Val Asp Glu Gly Lys Val Glu Gly Gln Asp Ser Phe Leu Lys Arg
                165                 170                 175

Met Ser Gly Met Ile Arg Leu Tyr Ala Ala Ile Ile Gln Met Arg Trp
            180                 185                 190

Pro Tyr Ser Ser Lys Gln Gly Leu His Leu His Gly Met Asn His Gly
        195                 200                 205

Trp Arg Trp Met Ala Gln Ile Leu Asn Met Glu Pro Leu Ala Asp Ile
    210                 215                 220

Thr Ala Thr Ile Leu Phe Asp Phe Leu Glu Val Cys Gly Asn Ala Leu
225                 230                 235                 240

Met Lys Gln Tyr Arg Val Gln Phe Trp Lys Leu Ile Leu Ile Ile Asn
                245                 250                 255

Glu

<210> SEQ ID NO 30
<211> LENGTH: 253
<212> TYPE: PRT
<213> ORGANISM: Bos taurus
<220> FEATURE:
<221> NAME/KEY: misc_feature
<223> OTHER INFORMATION: Gle1 domains of Bos taurus (Bt)

<400> SEQUENCE: 30

Arg Cys Val Leu Ala Phe Glu Gly Leu Ser Asn Ser Lys Asp Ser Gln
1               5                   10                  15

Ala Lys Lys Ile Lys Met Asp Leu Gln Lys Ala Ala Thr Ile Pro Val
            20                  25                  30

Ser Gln Ile Ser Thr Ile Ala Gly Ser Lys Leu Lys Glu Ile Phe Asp
```

```
                35                  40                  45
Lys Ile His Ser Leu Leu Ser Gly Lys Pro Val Gln Ser Gly Gly Arg
             50                  55                  60

Ser Val Ser Val Thr Leu Asn Pro Gln Gly Leu Asp Phe Val Gln Tyr
65                  70                  75                  80

Lys Leu Ala Glu Lys Phe Val Lys Gln Gly Glu Glu Val Ala Ser
                85                  90                  95

His His Glu Ala Ala Phe Pro Ile Ala Val Ala Ser Gly Ile Trp
            100                 105                 110

Glu Leu His Pro Arg Val Gly Ala Leu Ile Leu Ala His Leu His Lys
            115                 120                 125

Lys Cys Pro Tyr Ser Val Pro Phe Tyr Pro Ala Phe Lys Glu Gly Met
            130                 135                 140

Ala Leu Glu Asp Tyr Gln Arg Met Leu Gly Tyr Gln Val Lys Asp Ser
145                 150                 155                 160

Lys Val Glu Gln Gln Asp Asn Phe Leu Lys Arg Met Ser Gly Met Ile
                165                 170                 175

Arg Leu Tyr Ala Ala Ile Ile Gln Leu Arg Trp Pro Tyr Gly Asn Arg
            180                 185                 190

Gln Glu Thr His Pro His Gly Leu Asn His Gly Trp Arg Trp Leu Ala
            195                 200                 205

Gln Ile Leu Asn Met Glu Pro Leu Ser Asp Val Thr Ala Thr Leu Leu
            210                 215                 220

Phe Asp Phe Leu Glu Val Cys Gly Asn Ala Leu Met Lys Gln Tyr Gln
225                 230                 235                 240

Val Gln Phe Trp Lys Met Ile Leu Leu Ile Lys Glu Asp
                245                 250

<210> SEQ ID NO 31
<211> LENGTH: 228
<212> TYPE: PRT
<213> ORGANISM: Arabidopsis thaliana
<220> FEATURE:
<221> NAME/KEY: misc_feature
<223> OTHER INFORMATION: Gle1 domains of Arabidopsis thaliana (At)

<400> SEQUENCE: 31

Asn Ser Ile Arg Ala Ala Glu Ser Ala Leu Ile Leu Glu Asn His Arg
1               5                   10                  15

Leu Lys Lys Leu Glu Glu Leu Glu Thr Thr Asn Gln Ser Leu Lys Ser
            20                  25                  30

Arg Ser Asn Glu Asn Phe Ser Phe Glu Lys His Ile Gly Arg Val
            35                  40                  45

Ile Arg Gln Ile Ser Gly Thr Lys Asp Ser Val Ser Gly Lys Ile Asn
        50                  55                  60

Asp Ile Val Lys Ile Phe Lys Asp Pro Arg Cys Pro Val Ser Ile Ser
65                  70                  75                  80

Ile Ala Ala Phe Ala Lys Lys Met Val Thr Thr Lys Glu Lys Pro Asn
                85                  90                  95

Pro Phe Ala Cys Ser Tyr Val Ile Val Tyr Ile Asn Ser Gln Phe Pro
            100                 105                 110

Gln Val Met Asp Ile Leu Leu Ala Glu Phe His Lys Ala Cys Ile Tyr
            115                 120                 125

Thr Val Pro Lys His Ile Val Asn Ser Gln Ser Ala Trp Asp Ser Asp
            130                 135                 140
```

```
Ala Tyr Glu Arg Leu Asp Ser Ile Met Arg Leu Tyr Gly Ala Leu Val
145                 150                 155                 160

Gln Thr Asp Ile Arg Val Gly Asn Ala Thr Asn Val His Gly Ile Glu
            165                 170                 175

His Gly Trp Ala Trp Leu Ala Arg Phe Leu Asn Lys Ile Pro Ala Asn
        180                 185                 190

Arg Ala Thr Ala Thr Ala Leu Asn Ser Phe Leu Gln Thr Ala Gly Phe
    195                 200                 205

Gly Leu His Gln Arg Tyr Lys Ser Gln Phe Leu Lys Val Val Asn Val
    210                 215                 220

Val Arg Glu His
225

<210> SEQ ID NO 32
<211> LENGTH: 249
<212> TYPE: PRT
<213> ORGANISM: Vitis vinifera
<220> FEATURE:
<221> NAME/KEY: misc_feature
<223> OTHER INFORMATION: Gle1 domains of Vitis vinifera (Vv)

<400> SEQUENCE: 32

Asn Ile Leu Lys Ser Ala Glu Ser Ala Leu Lys Leu Glu Gln Glu Arg
1               5                   10                  15

Leu Gln Lys Tyr Lys Glu Phe Asp Glu Lys Thr Gln Ala Leu Gly Gln
            20                  25                  30

Ser Ser Asn Lys Asp Phe Gln Arg His Glu Gln Gln Phe Ala Arg Arg
        35                  40                  45

Ile Arg Gln Ile Ser Gly Ser Lys Glu Asn Val Arg Thr Lys Gly Asn
50                  55                  60

Ala Leu Ile Lys Met Phe Asn Asp Pro Leu Cys Pro Gln Pro Ile Asn
65                  70                  75                  80

Val Ala Ile Phe Val Lys Lys Val Val Ser Tyr Phe Glu Val Asp Gln
                85                  90                  95

Pro Ser Lys Val Thr Tyr Ala Cys Gly His Val Ile Val Phe Val Ala
            100                 105                 110

Ser Gln Val Pro Tyr Ala Met Asp Leu Leu Leu Ala Glu Leu His Arg
        115                 120                 125

Val Cys Ile Tyr Thr Val Pro Lys His Ile Asp Tyr Ser Lys Ser Ala
    130                 135                 140

Phe Lys Ser Lys Glu Asp Tyr Tyr Lys Met Ile Gly Tyr Arg Glu Glu
145                 150                 155                 160

Asn Gly Lys Ile Glu Arg Thr Glu Asp Tyr Leu Lys Arg Leu Ala Cys
                165                 170                 175

Tyr Met Lys Leu Tyr Ala Ala Leu Val Gln Thr Glu Ala Asp Gly Val
            180                 185                 190

Lys Asn Pro His Gly Leu Lys Glu Gly Trp Ala Trp Leu Ala Arg Phe
        195                 200                 205

Leu Asn Ala Leu Pro Ala Asn Val Tyr Thr Val Ala Leu Glu Val
    210                 215                 220

Phe Leu Gln Val Ala Gly Phe Ala Leu Phe Arg Lys Tyr Arg Ser Gln
225                 230                 235                 240

Phe Arg Lys Ile Leu Lys Val Ile Ser
                245

<210> SEQ ID NO 33
```

```
<211> LENGTH: 224
<212> TYPE: PRT
<213> ORGANISM: Populus trichocarpa
<220> FEATURE:
<221> NAME/KEY: misc_feature
<223> OTHER INFORMATION: Gle1 domains of Populus trichocarpa (Pt1)

<400> SEQUENCE: 33
```

Ser Asn Arg Thr Lys Lys Ser Gln Thr Thr Gly Asp Asp Phe Ser Asn
1               5                   10                  15

His Glu Arg His Ile Ser Arg Leu Ile Arg Gln Ile Arg Gly Ile Lys
            20                  25                  30

Glu Asn Val Arg Val Lys Ala Ser Glu Leu Val Lys Ile Leu Lys Asn
        35                  40                  45

Pro Ser Cys Pro Gln Ser Ile Ser Val Ala Ala Phe Ala Lys Lys Val
    50                  55                  60

Val Ser His Cys Glu Ser Pro Asp Asn Ala Val Phe Ala Cys Gly His
65                  70                  75                  80

Val Ile Val Leu Val Thr Ser Gln Val Pro Gln Ala Met Asp Leu Leu
                85                  90                  95

Leu Ala Glu Phe His Arg Ala Cys Ile Tyr Thr Val Pro Lys His Ile
            100                 105                 110

Val Tyr Ser Lys Ser Ala Phe Glu Ser Lys Glu Ala Tyr Tyr Lys Asp
        115                 120                 125

Ile Gly His Arg Glu Asp Gly Gly Lys Leu Glu Ser Val Lys Asp Tyr
    130                 135                 140

Leu Lys Arg Leu Glu Ser Tyr Met Lys Leu Tyr Gly Ala Leu Val Gln
145                 150                 155                 160

Thr Glu Val Gln Gly Val Pro Asn Ile His Gly Pro Lys Glu Gly Trp
                165                 170                 175

Ala Trp Leu Ala Arg Phe Leu Asn Val Leu Pro Ala Asn Met Tyr Thr
            180                 185                 190

Ala Val Ala Leu Asn Ala Phe Leu Gln Thr Ala Gly Phe Val Leu Phe
        195                 200                 205

Arg Lys Tyr Lys Ser Gln Phe Thr Lys Met Leu His Ile Ile Leu Asn
    210                 215                 220

```
<210> SEQ ID NO 34
<211> LENGTH: 187
<212> TYPE: PRT
<213> ORGANISM: Glycine max
<220> FEATURE:
<221> NAME/KEY: misc_feature
<223> OTHER INFORMATION: Gle1 domains of Glycine max (Gm)

<400> SEQUENCE: 34
```

Arg Gly Ile Ser Asp Asn Val Arg Ser Lys Ala Ser Glu Leu Thr Lys
1               5                   10                  15

Leu Leu Ser His Pro Gln Ser Phe Gln Ser Ile Ser Ile Glu Ile Phe
            20                  25                  30

Ala Lys Lys Val Val Ala Tyr Cys Ala Asn Pro Ala Asn Val Pro Phe
        35                  40                  45

Ala Ser Ala Tyr Val Ile Val Leu Val Thr Ser Gln Val Pro His Ala
    50                  55                  60

Met Asp Ile Leu Leu Ala Glu Leu His Arg Ala Cys Ile Tyr Thr Val
65                  70                  75                  80

Pro Lys His Leu Val Tyr Lys Lys Ser Ala Tyr Gln Ser Lys Glu Ala
                85                  90                  95

Tyr Phe Arg Ser Ile Gly Tyr Arg Glu Asp Glu Lys Met Glu Ser
                100                 105                 110

Thr Glu Asp Tyr Leu Lys Arg Leu Glu Ser Tyr Met Lys Met Tyr Gly
            115                 120                 125

Ala Leu Val Gln Thr Glu Ile Thr Asn Cys Gln Asn Phe His Gly Leu
130                 135                 140

Lys Glu Gly Trp Ala Trp Leu Ala Arg Phe Leu Asn Thr His Pro Ala
145                 150                 155                 160

Asn Gln Tyr Thr Ala Val Ser Leu Asn Ala Phe Leu Gln Met Ala Gly
                165                 170                 175

Phe Ala Leu Tyr Asn Arg Tyr Lys Ser Gln Phe
            180                 185

<210> SEQ ID NO 35
<211> LENGTH: 256
<212> TYPE: PRT
<213> ORGANISM: Nicotiana benthamiana
<220> FEATURE:
<221> NAME/KEY: misc_feature
<223> OTHER INFORMATION: Gle1 domains of Nicotiana benthamiana (Nb)

<400> SEQUENCE: 35

Ser Ala Gly Asn Thr Ile Arg Val Ser Glu Asn Ala Gln Lys Leu Glu
1               5                   10                  15

Glu Lys Arg Leu Met Ile Tyr Asn Glu Ile Ala Ser Gln Asn Glu Ala
            20                  25                  30

Leu Gly Leu Gly Ser Asn Lys Ala Tyr Arg Lys Tyr Glu Met Glu Ile
            35                  40                  45

Ala Arg Arg Ile Arg Thr Ile Thr Gly Thr Lys Glu Asn Val Arg Val
        50                  55                  60

Lys Ala Asp Glu Leu Ile Lys Leu Met Ser Asp Pro Thr Cys Pro Gln
65                  70                  75                  80

Ser Ile Ser Ile Ala Met Phe Ala Gln Lys Val Val Ser Leu Cys Val
                85                  90                  95

Asn Pro Thr Gly Ser Phe Asn Ser Ala Val Tyr Ala Tyr Gly Arg Val
            100                 105                 110

Ile Val Leu Val Thr Ser Lys Val Ser Leu Ala Met Asp Val Leu Ile
            115                 120                 125

Gly Glu Leu Asn Lys Val Cys Ile Tyr Ala Val Pro Lys Tyr Ile Val
        130                 135                 140

Tyr Ser Glu Ala Ala Phe Gln Thr Lys Glu Ala Tyr Tyr Lys Ala Ile
145                 150                 155                 160

Gly Tyr Ala Glu Glu Asp Gly Lys Ile Glu Ser Thr Asp Ser Tyr Val
                165                 170                 175

Asp Arg Leu Ser Ala Tyr Met Lys Leu Tyr Gly Ala Leu Val Gln Thr
            180                 185                 190

Glu Val Glu Gly Cys Gln Asn Leu His Gly Leu Arg Glu Ala Trp Ala
            195                 200                 205

Trp Ile Ala Arg Phe Leu Asn Val Leu Pro Ala Asn Leu Tyr Thr Ala
        210                 215                 220

Ala Ala Leu Gln Ala Phe Leu Glu Met Ala Gly Phe Ala Leu His Lys
225                 230                 235                 240

Arg Tyr Lys Thr Gln Phe Arg Lys Met Leu Asp Ile Ile Ala Lys Asp
                245                 250                 255

-continued

```
<210> SEQ ID NO 36
<211> LENGTH: 233
<212> TYPE: PRT
<213> ORGANISM: Ricinus communis
<220> FEATURE:
<221> NAME/KEY: misc_feature
<223> OTHER INFORMATION: Gle1 domains of Ricinus communis (Rc)

<400> SEQUENCE: 36

Ser Ile Ile Arg Ala Ala Glu Ser Ala Leu Ser Leu Glu Gln Lys Arg
1               5                   10                  15

Leu Glu Lys Leu Arg Ala Leu Glu Glu Gln Asn Arg Ser Leu Lys Leu
            20                  25                  30

Ser Ser Asn Met Asp Phe Ser Ser His Glu Arg His Val Ala Arg Leu
        35                  40                  45

Ile Lys Gln Ile Arg Gly Thr Lys Glu Asn Val Arg Ala Lys Ser Ser
    50                  55                  60

Glu Leu Val Lys Leu Cys Gln Asn Pro Ser Cys Pro Gln Ser Ile Ser
65                  70                  75                  80

Ile Ala Ala Ile Ala Thr Phe Pro Lys Lys Val Ala Ser Gln Ser Glu
                85                  90                  95

Leu Pro Asp Ser Ala Val Phe Ala Cys Ala Tyr Val Ile Val Met Val
            100                 105                 110

Thr Ser Gln Val Pro His Ser Met Asn Leu Leu Leu Ala Glu Phe His
        115                 120                 125

Arg Gly Cys Ile Tyr Thr Val Pro Arg His Val Thr Tyr Ser Lys Asn
    130                 135                 140

Gly Lys Ile Glu Ser Thr Thr Asp Tyr Leu Lys Arg Leu Glu Cys Tyr
145                 150                 155                 160

Met Arg Leu Tyr Gly Ala Leu Val Gln Thr Glu Val Gln Gly Phe Gln
                165                 170                 175

Asn Ser His Gly Pro Asn Glu Gly Trp Ala Trp Leu Ala Arg Phe Leu
            180                 185                 190

Asn Asn Leu Pro Ala Asn Ile Tyr Thr Ala Val Ala Leu Asn Gly Phe
        195                 200                 205

Leu Lys Thr Ala Gly Phe Val Leu Phe Arg Lys Tyr Arg Ser Gln Phe
    210                 215                 220

Gly Lys Met Leu Asn Ile Ile Tyr Asn
225                 230

<210> SEQ ID NO 37
<211> LENGTH: 248
<212> TYPE: PRT
<213> ORGANISM: Oryza sativa
<220> FEATURE:
<221> NAME/KEY: misc_feature
<223> OTHER INFORMATION: Gle1 domains of Oryza sativa (Os)

<400> SEQUENCE: 37

Lys Val Phe Ala Asp His Ser Ala Leu Glu Ala Glu Leu Arg Arg Arg
1               5                   10                  15

Ala Leu Leu Asp Gln Val Pro Ala Asn Ile His Ser Ser Lys Glu Phe
            20                  25                  30

Ser Arg Tyr Asp Arg Gln Ile Ala Lys Ser Ile Gly Lys Leu Met Pro
        35                  40                  45

Thr Thr Asp Ser Val Lys Ala Arg Ala Gly Glu Leu Ile Lys Ala Leu
    50                  55                  60

Asp Gly Gln Asp Cys Pro Arg Pro Ile Ala Cys Arg Ile Phe Ala Asn
```

```
                65                  70                  75                  80
Lys Ile Ile Ser Ile Val Lys Ser Arg Asn Thr Lys Asp Lys Thr Phe
                    85                  90                  95
Gly Asn Leu Ala Phe Ala Cys Gly Tyr Val Met Leu Val Thr Ser
                100                 105                 110
Gln Val Pro Asp Ala Met Asp Tyr Leu Leu Ala Glu Phe His Arg Val
            115                 120                 125
Cys Met Tyr Thr Val Pro Lys His Leu His Ala Leu Asn Ala Gln Val
130                 135                 140
Arg Asn Arg Asp Tyr Tyr Arg Leu Ile Gly Tyr Gln Glu Glu Asn Gly
145                 150                 155                 160
Gln Leu Glu Ser Thr Glu Ser Tyr Leu Thr Tyr Val Ala Ala Tyr Val
                165                 170                 175
Lys Leu Tyr Ala Ala Met Ile Gln Thr Glu Ile Arg Gly Val Arg His
                180                 185                 190
Pro Tyr Gly Leu Ala Glu Gly Trp Lys Trp Leu Ala Met Phe Leu Asn
            195                 200                 205
Thr Leu Pro Ala Thr Thr Ala Thr Ala Cys Ala Leu His Ala Phe Leu
210                 215                 220
Lys Val Ala Gly Phe Ala Leu His Lys Lys Tyr Gly Ser Gln Phe Met
225                 230                 235                 240
Lys Leu Leu Asp Val Ile Leu Arg
                245

<210> SEQ ID NO 38
<211> LENGTH: 221
<212> TYPE: PRT
<213> ORGANISM: Zea mays
<220> FEATURE:
<221> NAME/KEY: misc_feature
<223> OTHER INFORMATION: Gle1 domains of Zea mays (Zm)

<400> SEQUENCE: 38

His Ser Lys Glu Phe Ser Lys Tyr Asp Arg Gln Ile Ala Lys Ser Ile
1               5                   10                  15
Ser Lys Leu Met Pro Thr Thr Asp Ser Val Arg Thr Arg Ala Ser Glu
                20                  25                  30
Leu Val Lys Ala Leu Asn Gly Gln Asp Cys Pro Arg Pro Ile Ser Cys
            35                  40                  45
Cys Leu Phe Ala Asn Lys Ile Ile Ser Ile Val Lys Ser Arg Asn Thr
        50                  55                  60
Lys Asp Lys Thr Phe Gly Asn Leu Ala Phe Ala Cys Gly Tyr Val Met
65                  70                  75                  80
Leu Leu Val Thr Asn Gln Val Pro Asp Ala Met Asp Tyr Leu Leu Ala
                85                  90                  95
Glu Phe Asn Arg Val Cys Ile Tyr Thr Val Pro Lys His Met His Ala
                100                 105                 110
Leu Asn Ala Gln Ala Arg Asn Arg Asp Tyr Tyr Arg Leu Ile Gly Tyr
            115                 120                 125
Gln Glu Glu Asn Gly Gln Leu Glu Ser Thr Glu Ser Tyr Leu Thr Tyr
130                 135                 140
Val Val Ala Tyr Val Lys Leu Tyr Ala Ala Met Ile Gln Thr Glu Ile
145                 150                 155                 160
Lys Gly Val Arg His Pro His Gly Leu Ala Glu Gly Trp Lys Trp Leu
                165                 170                 175
```

```
Ala Met Phe Leu Asn Ser Leu Pro Ala Thr Thr Ala Thr Ala Cys Ala
            180                 185                 190

Leu His Ala Phe Leu Lys Met Ala Gly Phe Ala Leu His Lys Lys Tyr
        195                 200                 205

Gly Ser Gln Phe Met Lys Ile Leu Asp Val Ile Ser Arg
    210                 215                 220

<210> SEQ ID NO 39
<211> LENGTH: 220
<212> TYPE: PRT
<213> ORGANISM: Hordeum vulgare
<220> FEATURE:
<221> NAME/KEY: misc_feature
<223> OTHER INFORMATION: Gle1 domains of Hordeum vulgare (Hv)

<400> SEQUENCE: 39

Lys Glu Tyr Ser Arg Tyr Asp Arg Gln Ile Gly Lys Ser Ile Ser Lys
1               5                   10                  15

Leu Met Pro Thr Thr Asp Ser Val Lys Ala Arg Ala Ser Glu Leu Ile
            20                  25                  30

Lys Ala Leu Asp Gly Gln Asp Cys Pro Arg Pro Ile Ala Cys Arg Leu
        35                  40                  45

Phe Ala Asp Lys Met Ile Ser Ile Val Lys Ser Arg Asn Pro Thr Asp
    50                  55                  60

Lys Thr Phe Gly Lys Leu Ala Phe Ala Cys Gly Tyr Val Met Leu Leu
65                  70                  75                  80

Val Ile Asn Gln Val Pro Asp Ala Met Asp Tyr Leu Leu Ala Glu Phe
                85                  90                  95

Asn Lys Val Cys Met Tyr Thr Val Pro Lys His Leu His Ala Leu Asn
            100                 105                 110

Ala Gln Ala Arg Asn Thr Asp Tyr Phe Arg Leu Ile Gly Tyr Gln Glu
        115                 120                 125

Glu Asp Gly Lys Leu Gln Ser Thr Glu Lys Tyr Leu Val Asn Val Val
    130                 135                 140

Ala Tyr Ile Lys Leu Tyr Ala Ala Met Ile Gln Thr Glu Ile Lys Gly
145                 150                 155                 160

Val Arg His Pro Tyr Gly Leu Ala Glu Gly Trp Lys Trp Leu Ala Met
                165                 170                 175

Phe Leu Asn Thr Leu Pro Ala Ile Pro Ala Thr Ala Phe Ala Leu His
            180                 185                 190

Ala Phe Leu Lys Val Ala Gly Phe Ala Leu His Lys Lys Tyr Gly Ser
        195                 200                 205

Gln Phe Met Lys Ile Leu Asp Val Ile Ser Arg His
    210                 215                 220

<210> SEQ ID NO 40
<211> LENGTH: 193
<212> TYPE: PRT
<213> ORGANISM: Triticum aestivum
<220> FEATURE:
<221> NAME/KEY: misc_feature
<223> OTHER INFORMATION: Gle1 domains of Triticum aestivum (Ta)

<400> SEQUENCE: 40

Met Pro Thr Thr Asp Ser Val Lys Ala Arg Ala Ser Glu Leu Ile Lys
1               5                   10                  15

Ala Leu Asp Gly Gln Asp Cys Pro Arg Pro Ile Ala Cys Arg Leu Phe
            20                  25                  30
```

```
Ala Asp Lys Met Ile Ser Ile Val Lys Ser Arg Asn Pro Thr Asp Lys
             35                  40                  45

Thr Phe Gly Lys Leu Ala Phe Ala Cys Gly Tyr Val Met Leu Leu Val
 50                  55                  60

Thr Asn Gln Val Pro Asp Ala Met Asp Tyr Leu Leu Ala Glu Phe Asn
65                   70                  75                  80

Lys Val Cys Met Tyr Thr Val Pro Lys His Leu His Ala Leu Asn Ala
                 85                  90                  95

Gln Ala Arg Asn Thr Asp Tyr Phe Arg Leu Ile Gly Tyr Gln Glu Glu
            100                 105                 110

Asp Gly Lys Leu Gln Ser Thr Glu Lys Tyr Leu Val Asn Val Val Ala
        115                 120                 125

Tyr Val Lys Leu Tyr Ala Ala Met Val Gln Thr Glu Ile Lys Gly Val
130                 135                 140

Arg His Pro His Gly Leu Ala Glu Gly Trp Lys Trp Leu Ala Met Phe
145                 150                 155                 160

Leu Asn Thr Leu Pro Ala Ile Pro Ala Thr Ala Phe Ala Leu His Ala
                165                 170                 175

Phe Leu Lys Val Ala Gly Phe Ala Leu His Lys Lys Tyr Gly Ser Gln
            180                 185                 190

Phe

<210> SEQ ID NO 41
<211> LENGTH: 220
<212> TYPE: PRT
<213> ORGANISM: Sorghum bicolor
<220> FEATURE:
<221> NAME/KEY: misc_feature
<223> OTHER INFORMATION: Gle1 domains of Sorghum bicolor (Sb)

<400> SEQUENCE: 41

Ser Lys Glu Phe Ser Lys Tyr Asp Arg Gln Ile Ala Lys Ser Ile Ser
1               5                   10                  15

Lys Leu Met Pro Thr Thr Asp Ser Val Arg Ala Arg Ala Ser Glu Leu
             20                  25                  30

Ile Lys Ala Leu Asp Gly Gln Asp Cys Pro Arg Pro Ile Ser Cys Tyr
         35                  40                  45

Leu Phe Ala Asn Lys Ile Ile Ser Ile Val Lys Ser Arg Asn Thr Lys
 50                  55                  60

Asp Lys Thr Phe Gly Asn Leu Ala Phe Ala Cys Gly Tyr Val Met Leu
65                   70                  75                  80

Leu Val Thr Asn Gln Val Pro Asp Ala Met Asp Tyr Leu Leu Ala Glu
                 85                  90                  95

Phe Asn Arg Val Cys Ile Tyr Thr Val Pro Lys His Leu His Ala Leu
            100                 105                 110

Asn Ala Gln Ala Arg Thr Arg Asp Tyr Tyr Lys Leu Ile Gly Tyr Glu
        115                 120                 125

Glu Glu Asn Glu Gln Leu Glu Ser Thr Glu Ser Tyr Leu Thr Tyr Val
130                 135                 140

Val Ala Tyr Val Lys Leu Tyr Ala Ala Met Ile Gln Thr Glu Ile Lys
145                 150                 155                 160

Gly Val Arg His Pro His Gly Leu Ala Glu Gly Trp Lys Trp Leu Ala
                165                 170                 175

Met Phe Leu Asn Ser Leu Pro Ala Thr Thr Ala Thr Ala Cys Ala Leu
            180                 185                 190
```

His Ala Phe Leu Lys Met Ala Gly Phe Ala Leu His Lys Lys Tyr Gly
            195                 200                 205

Ser Gln Phe Met Lys Ile Leu Asp Val Ile Ser Arg
    210                 215                 220

<210> SEQ ID NO 42
<211> LENGTH: 219
<212> TYPE: PRT
<213> ORGANISM: Brachypodium distachyon
<220> FEATURE:
<221> NAME/KEY: misc_feature
<223> OTHER INFORMATION: Gle1 domains of Brachypodium distachyon (Bd)

<400> SEQUENCE: 42

Lys Glu Phe Ser Lys Tyr Asp Arg Gln Ile Gly Lys Ser Ile Ser Lys
1               5                   10                  15

Leu Met Pro Thr Thr Asp Ser Val Lys Ala Arg Ala Ser Glu Leu Val
            20                  25                  30

Lys Ala Leu Asp Gly His Glu Cys Pro Arg Pro Ile Ala Cys Arg Leu
        35                  40                  45

Phe Ala Asp Lys Ile Ile Ser Ile Val Lys Ser Arg Asn Pro Lys Asp
    50                  55                  60

Lys Thr Phe Gly Asn Leu Ala Phe Ala Cys Gly Tyr Val Met Leu Leu
65                  70                  75                  80

Val Thr Asn Gln Val Pro Glu Ala Met Asp Tyr Leu Leu Ala Glu Phe
                85                  90                  95

His Lys Val Cys Val Tyr Thr Val Pro Lys His Leu His Ala Leu Asn
            100                 105                 110

Ala Gln Ala Arg Asn Arg Asp Tyr Tyr Arg Leu Ile Gly Tyr Gln Glu
        115                 120                 125

Glu Asn Gly Gln Leu Glu Ser Thr Glu Lys Tyr Leu Thr Asn Val Ala
    130                 135                 140

Ala Tyr Val Lys Leu Tyr Ala Ala Met Ile Gln Thr Glu Ile Lys Gly
145                 150                 155                 160

Val His His Pro His Gly Leu Ala Glu Gly Trp Lys Trp Leu Ala Met
                165                 170                 175

Phe Leu Asn Thr Leu Pro Ala Thr Thr Ala Thr Ala Cys Ala Leu His
            180                 185                 190

Ala Phe Leu Lys Met Ala Gly Phe Ala Leu His Lys Lys Tyr Gly Ser
        195                 200                 205

Gln Phe Met Lys Val Leu Asp Val Ile Ser Arg
    210                 215

<210> SEQ ID NO 43
<211> LENGTH: 219
<212> TYPE: PRT
<213> ORGANISM: Pinus teada
<220> FEATURE:
<221> NAME/KEY: misc_feature
<223> OTHER INFORMATION: Gle1 domains of Pinus teada (Pt2)

<400> SEQUENCE: 43

Thr Gly Thr Gln Glu Gln Val Arg Ala Lys Ser Thr Glu Leu Phe Lys
1               5                   10                  15

Met Ile Thr Asp Pro His Val Pro Gln Cys Ile Leu Leu Thr Gly Phe
            20                  25                  30

Ala Val Lys Ala Val Ser Gln Cys Glu Thr Gln Thr Leu Ser Leu Asn
        35                  40                  45

Ser Ile Ala Phe Ala Leu Ala His Val Ile Val Leu Val Thr Ser Gln
    50                  55                  60

Val Pro Ile Ala Met Asp Leu Val Leu Ala Glu Leu His Lys Ser Cys
 65                  70                  75                  80

Ile Phe Thr Val Pro Lys Tyr Ile Pro Tyr Ser Lys Val Cys Gly Met
                 85                  90                  95

Val Asn Tyr Gly Val Ala Thr Arg Ala Arg Cys Met Glu Ala Cys Cys
                100                 105                 110

Tyr Trp Gln Gln Ile Trp Leu Gln Ile Ala Phe Glu Ser Glu Asn Ala
                115                 120                 125

Tyr Tyr Lys Thr Val Gly Tyr Arg Glu Asp Asn Gly Lys Ile Glu Ser
                130                 135                 140

Thr Asp Asn Tyr Leu Ala Arg Met Lys Ala Tyr Val Thr Leu Tyr Ala
145                 150                 155                 160

Ala Ile Ile Gln Thr Asp Ile Pro Gly Val Asn Asn Leu His Gly Val
                165                 170                 175

Lys Asp Gly Trp Ser Trp Met Ala Arg Phe Leu Asn Ala Leu Pro Pro
                180                 185                 190

Asn Arg Phe Thr Ala Ala Leu Glu Ile Phe Leu Lys Ile Ala Gly
                195                 200                 205

Phe Arg Leu Tyr Gln Ala Tyr Pro Arg Pro Phe
210                 215

<210> SEQ ID NO 44
<211> LENGTH: 14
<212> TYPE: PRT
<213> ORGANISM: Saccharomyces cerevisiae
<220> FEATURE:
<221> NAME/KEY: misc_feature
<223> OTHER INFORMATION: Amino acid sequence surrounding the key
      residues of the InsP6-binding pocket of Gle1 of Saccharomyces
      cerevisiae (Sc)

<400> SEQUENCE: 44

Phe Met Ala Arg Leu Val Lys Lys Cys Pro Phe Val Ile Gly
 1               5                   10

<210> SEQ ID NO 45
<211> LENGTH: 14
<212> TYPE: PRT
<213> ORGANISM: Candida albicans SC5314
<220> FEATURE:
<221> NAME/KEY: misc_feature
<223> OTHER INFORMATION: Amino acid sequence surrounding the key
      residues of the InsP6-binding pocket of Gle1 of Candida albicans
      SC5314 (Ca)

<400> SEQUENCE: 45

Ile Asn Ala Arg Phe Ile Lys Lys Cys Pro Tyr Ile Ile Gly
 1               5                   10

<210> SEQ ID NO 46
<211> LENGTH: 14
<212> TYPE: PRT
<213> ORGANISM: Homo sapiens
<220> FEATURE:
<221> NAME/KEY: misc_feature
<223> OTHER INFORMATION: Amino acid sequence surrounding the key
      residues of the InsP6-binding pocket of Gle1 of Homo sapiens (Hs)

<400> SEQUENCE: 46

Ile Leu Ala His Leu His Lys Lys Cys Pro Tyr Ser Val Pro
 1               5                   10

```
<210> SEQ ID NO 47
<211> LENGTH: 14
<212> TYPE: PRT
<213> ORGANISM: Mus musculus
<220> FEATURE:
<221> NAME/KEY: misc_feature
<223> OTHER INFORMATION: Amino acid sequence surrounding the key
      residues of the InsP6-binding pocket of Gle1 of Mus musculus (Mm)

<400> SEQUENCE: 47

Ile Leu Ala His Leu His Lys Lys Cys Pro Tyr Ser Val Pro
1               5                   10

<210> SEQ ID NO 48
<211> LENGTH: 14
<212> TYPE: PRT
<213> ORGANISM: Danio rerio
<220> FEATURE:
<221> NAME/KEY: misc_feature
<223> OTHER INFORMATION: Amino acid sequence surrounding the key
      residues of the InsP6-binding pocket of Gle1 of Danio rerio (Dr)

<400> SEQUENCE: 48

Ile Leu Ala His Leu His Lys Lys Cys Pro Tyr Ala Val Pro
1               5                   10

<210> SEQ ID NO 49
<211> LENGTH: 14
<212> TYPE: PRT
<213> ORGANISM: Bos taurus
<220> FEATURE:
<221> NAME/KEY: misc_feature
<223> OTHER INFORMATION: Amino acid sequence surrounding the key
      residues of the InsP6-binding pocket of Gle1 of Bos taurus (Bt)

<400> SEQUENCE: 49

Ile Leu Ala His Leu His Lys Lys Cys Pro Tyr Ser Val Pro
1               5                   10

<210> SEQ ID NO 50
<211> LENGTH: 14
<212> TYPE: PRT
<213> ORGANISM: Arabidopsis thaliana
<220> FEATURE:
<221> NAME/KEY: misc_feature
<223> OTHER INFORMATION: Amino acid sequence surrounding the key
      residues of the InsP6-binding pocket of Gle1 of Arabidopsis
      thaliana (At)

<400> SEQUENCE: 50

Leu Leu Ala Glu Phe His Lys Ala Cys Ile Tyr Thr Val Pro
1               5                   10

<210> SEQ ID NO 51
<211> LENGTH: 14
<212> TYPE: PRT
<213> ORGANISM: Vitis vinifera
<220> FEATURE:
<221> NAME/KEY: misc_feature
<223> OTHER INFORMATION: Amino acid sequence surrounding the key
      residues of the InsP6-binding pocket of Gle1 of Vitis vinifera
      (Vv)

<400> SEQUENCE: 51

Leu Leu Ala Glu Leu His Arg Val Cys Ile Tyr Thr Val Pro
1               5                   10
```

```
<210> SEQ ID NO 52
<211> LENGTH: 14
<212> TYPE: PRT
<213> ORGANISM: Populus trichocarpa
<220> FEATURE:
<221> NAME/KEY: misc_feature
<223> OTHER INFORMATION: Amino acid sequence surrounding the key
      residues of the InsP6-binding pocket of Gle1 of Populus
      trichocarpa (Pt1)

<400> SEQUENCE: 52

Leu Leu Ala Glu Phe His Arg Ala Cys Ile Tyr Thr Val Pro
1               5                   10

<210> SEQ ID NO 53
<211> LENGTH: 14
<212> TYPE: PRT
<213> ORGANISM: Nicotiana benthamiana
<220> FEATURE:
<221> NAME/KEY: misc_feature
<223> OTHER INFORMATION: Amino acid sequence surrounding the key
      residues of the InsP6-binding pocket of Gle1 of Nicotiana
      benthamiana (Nb)

<400> SEQUENCE: 53

Leu Leu Gly Glu Leu Asn Lys Val Cys Ile Tyr Ala Val Pro
1               5                   10

<210> SEQ ID NO 54
<211> LENGTH: 14
<212> TYPE: PRT
<213> ORGANISM: Ricinus communis
<220> FEATURE:
<221> NAME/KEY: misc_feature
<223> OTHER INFORMATION: Amino acid sequence surrounding the key
      residues of the InsP6-binding pocket of Gle1 of Ricinus communis
      (Rc)

<400> SEQUENCE: 54

Leu Leu Ala Glu Phe His Arg Gly Cys Ile Tyr Thr Val Pro
1               5                   10

<210> SEQ ID NO 55
<211> LENGTH: 14
<212> TYPE: PRT
<213> ORGANISM: Sorghum bicolor
<220> FEATURE:
<221> NAME/KEY: misc_feature
<223> OTHER INFORMATION: Amino acid sequence surrounding the key
      residues of the InsP6-binding pocket of Gle1 of monocotyledonous
      plants Sorghum bicolor (Sb)

<400> SEQUENCE: 55

Leu Leu Ala Glu Phe Asn Arg Val Cys Ile Tyr Thr Val Pro
1               5                   10

<210> SEQ ID NO 56
<211> LENGTH: 14
<212> TYPE: PRT
<213> ORGANISM: Brachypodium distachyon
<220> FEATURE:
<221> NAME/KEY: misc_feature
<223> OTHER INFORMATION: Amino acid sequence surrounding the key
      residues of the InsP6-binding pocket of Gle1 of Brachypodium
      distachyon (Bd)

<400> SEQUENCE: 56

Leu Leu Ala Glu Phe His Lys Val Cys Val Tyr Thr Val Pro
1               5                   10
```

```
<210> SEQ ID NO 57
<211> LENGTH: 14
<212> TYPE: PRT
<213> ORGANISM: Pinus teada
<220> FEATURE:
<221> NAME/KEY: misc_feature
<223> OTHER INFORMATION: Amino acid sequence surrounding the key
      residues of the InsP6-binding pocket of Gle1 of Pinus teada (Pt2)

<400> SEQUENCE: 57

Val Leu Ala Glu Leu His Lys Ser Cys Ile Phe Thr Val Pro
1               5                   10
```

NUCLEIC ACID MOLECULE ENCODING GLE1 PROTEIN VARIANT WITH INCREASED PHYTIC ACID SENSITIVITY AND USE THEREOF

CROSS-REFERENCE TO RELATED APPLICATION

This application claims priority to and the benefit of Korean Patent Application No. 2015-0007246, filed on Jan. 15, 2015 and International Patent Application No. PCT/KR2016/000481, filed on Jan. 15, 2016, the disclosure of which is incorporated herein by reference in its entirety.

SEQUENCE LISTING

The instant application contains a Sequence Listing, created on Aug. 8, 2018; the file, in ASCII format, is designated H1258184.txt and is 459.0 KB in size. The file is hereby incorporated by reference in its entirety into the instant application.

BACKGROUND

1. Field of the Invention

The present invention relates to a nucleic acid molecule encoding a Gle1 protein variant with increased sensitivity to phytic acid, a protein coded by the nucleic acid molecule, and a use and method of the protein for improving a seed yield, promoting germination and growth or increasing abiotic stress tolerance in phytate-deficient plants.

2. Discussion of Related Art

Myo-inositol-1,2,3,4,5,6-hexakisphosphate ($InsP_6$), known as phytic acid, is the major form of phosphorous in plant seeds, and provided as a reservoir for phosphate, minerals and inositol to support seed germination and seedling growth (; Raboy, V. (2003). myo-Inositol-1,2,3,4,5,6-hexakisphosphate. Phytochemistry 64: 1033-1043; Raboy, V. (2009). Approaches and challenges to engineering seed phytate and total phosphorus. Plant Sci. 177: 281-296.; Munnik, T., and Nielsen, E. (2011). Green light for polyphosphoinositide signals in plants. Curr. Opin. Plant Biol. 14: 489-497.). However, high contents of phytic acid in cereal grains and legumes have been known to cause nutritional and environmental problems (Raboy, Seeds for a better future: 'low phytate' grains help to overcome malnutrition and reduce pollution. Trends Plant Sci. 6:458-462, 2001; Raboy, Approaches and challenges to engineering seed phytate and total phosphorus. Plant Sci. 177: 281-296, 2009; Brinch-Pedersen et al., Heat-stable phytases in transgenic wheat (*Triticum aestivum* L.): deposition pattern, thermostability, and phytate hydrolysis. J. Agric. Food Chem. 54: 4624-4632, 2006; Beardsley, Peak phosphorus. Bioscience 61: 91, 2011). Phytic acid is a strong chelator of cations of a mineral such as iron, zinc or calcium, forming stable salts called phytins. Phytins are indigestible to humans and nonruminant animals and mostly excreted, resulting in mineral deficiency. The inability to use the phosphorous of phytic acid resulted in increased feed costs for pigs, poultry and fish because they need to supplement phosphorous for proper growth.

In addition, the excretion of undigested $InsP_6$ in animal waste is an important cause of water pollution. Thus, the phytic acid of seeds has a very adverse effect on the nutrition and environment for humans and animals.

To improve the nutritional quality of crops, low-phytic acid (lpa) mutants of maize, barley, wheat, rice and soybeans have been isolated, and they are mutated in myo-inositol-3-phosphate synthase (MIPS), myo-inositol kinase (MIK), inositol polyphosphate kinase (IPK), and multidrug resistance-associated (MRP) ATP-binding cassette transporter genes (Raboy et al., Origin and seed phenotype of maize low phytic acid 1-1 and low phytic acid 2-1. Plant Physiol. 124: 355-368, 2000; Meis et al., Seed source effect on field emergence of soybean lines with reduced phytate and raffinose saccharides. Crop Sci. 43: 1336-1339, 2003; Shi et al., The maize low-phytic acid mutant lpa2 is caused by mutation in an inositol phosphate kinase gene. Plant Physiol. 131: 507-515, 2003; Shi et al, The maize low-phytic acid 3 encodes a myo-inositol kinase that plays a role in phytic acid biosynthesis in developing seeds. Plant J. 42: 708-719, 2005; Shi et al., Embryospecific silencing of a transporter reduces phytic acid content of maize and soybean seeds. Nat. Biotechnol. 25: 930-937, 2007; Bregitzer and Raboy, Effects of four independent lowphytate mutations on barley agronomic performance. Crop Sci. 46: 1318-1322, 2006; Murphy et al., A role for inositol hexakisphosphate in the maintenance of basal resistance to plant pathogens. Plant J. 56: 638-652, 2008; Raboy, Approaches and challenges to engineering seed phytate and total phosphorus. Plant Sci. 177: 281-296, 2009;). However, such mutants frequently showed undesirable crop characteristics such as reduced seed yield and weight, poor seed germination and stunted vegetative growth. Accordingly, to reduce adverse effects of the low-phytic acid mutation, seed-targeted low-phytic acid engineering has recently been attempted using seed-specific promoters (Shi et al., Embryospecific silencing of a transporter reduces phytic acid content of maize and soybean seeds. Nat. Biotechnol. 25: 930-937, 2007; Kuwano et al., Generation of stable 'low phytic acid' transgenic rice through antisense repression of the 1D-myo-inositol 3-phosphate synthase gene (RINO1) using the 18-kDa oleosin promoter. Plant Biotechnol. J. 7: 96-105, 2009; Ali et al., Development of low phytate rice by RNAi mediated seed-specific silencing of inositol 1,3,4,5,6-pentakisphosphate 2-kinase gene (IPK1). PLoS ONE 8: e68161, 2013; Li et al., Seed-specific silencing of OsMRP5 reduces seed phytic acid and weight in rice. Transgenic Res. 23: 585-599, 2014). Despite such attempts, high yield low-phytate crops have not yet been commercialized.

$InsP_6$ is very abundant in eukaryotic cells, and involved in various cellular processes. In yeast and mammals, $InsP_6$ has been known to be involved in mRNA export, translational control, RNA editing, and DNA repair (Hanakahi and West, Specific interaction of IP6 with human Ku70/80, the DNA-binding subunit of DNA-PK. EMBO J. 21: 2038-2044, 2002; Macbeth et al., Inositol hexakisphosphate is bound in the ADAR2 core and required for RNA editing. Science 309: 1534-1539, 2005; Bolger et al., The mRNA export factor Gle1 and inositol hexakisphosphate regulate distinct stages of translation. Cell 134: 624-633, 2008; Montpetit et al., A conserved mechanism of DEAD-box ATPase activation by nucleoporins and InsP6 in mRNA export. Nature 472: 238-242, 2011). In plants, $InsP_6$ is present as a storage form (phytate) in seeds and has been associated with hormonal and signal transduction processes. $InsP_6$ stimulates $Ca^{2+}$ export in guard cells in response to abscisic acid, inducing stomatal closure (Lemtiri-Chlieh et al., Inositol hexakisphosphate mobilizes an endomembrane store of calcium in guard cells. Proc. Natl. Acad. Sci. USA 100: 10091-10095, 2003). InsP$_6$ was identified by the X-ray crystal structure of the auxin receptor TIR, probably as a structural cofactor (Tan et al., Mechanism of auxin perception by the TIR1 ubiquitin ligase. Nature 446: 640-645, 2007). However, the detailed function and significance of InsP$_6$ signaling in plant development have not yet been revealed.

The inventors have previously reported that a nuclear pore protein Rae1 (yeast Gle2p) plays a dual role in plants, in relation to mRNA export in interphase and in spindle assembly in mitosis (Lee et al., Dual functions of *Nicotiana benthamiana* Rae1 in interphase and mitosis. Plant J. 59: 278-291, 2009). This result is consistent with recent findings in which a nuclear pore complex (NPC) protein performs a function besides the role as a structural component for NPC (Blower et al., A Rae1-containing ribonucleoprotein complex is required for mitotic spindle assembly. Cell 121: 223-234, 2005; Jeganathan et al., The Rae1-Nup98 complex prevents aneuploidy by inhibiting securin degradation. Nature 438: 1036-1039, 2005; Orjalo et al., The Nup107-160 nucleoporin complex is required for correct bipolar spindle assembly. Mol. Biol. Cell 17: 3806-3818, 2006; Franks and Hetzer, The role of Nup98 in transcription regulation in healthy and diseased cells. Trends Cell Biol. 23: 112-117, 2013; Vollmer and Antonin, The diverse roles of the Nup93/Nic96 complex proteins—structural scaffolds of the nuclear pore complex with additional cellular functions. Biol. Chem. 395: 515-528, 2014). To identify plant NPC proteins with atypical functions, the inventors performed screening for the phenotypes of *Nicotiana benthamiana* NPC genes using virus-induced gene silencing (VIGS), and ploidy analysis using *N. benthamiana* Rae1 and Nup96 (involved in auxin signaling) as controls.

The VIGS for most of the tested genes showed a slightly mild phenotype in *N. benthamiana*, which means that partial gene silencing cannot make the genes lose their cellular functions. However, VIGS of Gle1 caused more visible phenotypes including growth arrest and abnormal leaf development without affecting the ploidy level of leaves. Gle1 is an essential multifunctional protein that is highly conserved from yeast to humans. In yeast, Gle1 and its cofactor InsP$_6$ activate DEAD-box ATPase Dbp5 for nuclear mRNA export in the NPC (Alcázar-Román et al., Inositol hexakisphosphate and Gle1 activate the DEAD-box protein Dbp5 for nuclear mRNA export. Nat. Cell Biol. 8: 711-716, 2006; Alcázar-Román et al., Control of mRNA export and translation termination by inositol hexakisphosphate requires specific interaction with Gle1. J. Biol. Chem. 285: 16683-16692, 2010; Dossani et al., Structure of the C-terminus of the mRNA export factor Dbp5 reveals the interaction surface for the ATPase activator Gle1. Proc. Natl. Acad. Sci. USA 106: 16251-16256, 2009; Montpetit et al., A conserved mechanism of DEAD-box ATPase activation by nucleoporins and InsP6 in mRNA export, Nature 472: 238-242, 2011). Gle1 is also found in the cytosol, and plays a role in translation initiation and termination in Dbp5-independent and -dependent manners (Bolger et al., The mRNA export factor Gle1 and inositol hexakisphosphate regulate distinct stages of translation. Cell 134: 624-633, 2008; Kutay and Panse, Gle1 does double duty. Cell 134: 564-566, 2008). In plants, the cellular functions of Gle1 were not known except that T-DNA insertion mutation of Gle1 of *Arabidopsis* causes an embryonic lethal phenotype (Braud et al., LONO1 encoding a nucleoporin is required for embryogenesis and seed viability in *Arabidopsis*. Plant Physiol. 160: 823-836, 2012). In the present invention, the inventors showed the cellular function of Gle1 in plants in relation to LOS4 and InsP$_6$, and suggested that a strategy for overcoming adverse effects of the low-phytic acid characteristic using Gle1 variants.

Throughout this specification, a number of theses and patent documents are provided as references and cited references thereof are shown. The disclosure of the cited theses and patent literatures are incorporated herein by reference in its entirety, and thus the level of the field of art including the present application and the scope of the present application are more fully described.

SUMMARY OF THE INVENTION

The inventors have tried to develop a novel method for solving problems of low seed productivity and low germination frequency, which are found in low-InsP$_6$-containing crops. As a result, it was identified that InsP$_6$ serves to control mRNA export as a cofactor of Gle1 in plants, and confirmed that Gle1 variants with increased affinity to InsP$_6$ allowe mRNA export to normally occur in low-InsP$_6$-containing plants, resulting in effectively rescuing low growth and low yields shown in low-InsP$_6$-containing plants, and thus completed the present invention.

Therefore, the present invention is directed to providing a nucleic acid molecule encoding a Gle1 protein variant.

The present invention is also directed to providing a Gle1 protein variant coded by the nucleic acid molecule.

The present invention is also directed to providing a gene delivery system which comprises the nucleic acid molecule.

The present invention is also directed to providing a composition for increasing seed yield, germination, growth, or abiotic stress tolerance in plants comprising the gene delivery system.

The present invention is also directed to providing plant cells and/or a plant, which is transformed by the gene delivery system.

The present invention is also directed to providing a method of increasing seed yield, promoting germination and growth or increasing abiotic stress tolerance in plants.

Other objects and advantages of the present invention will be more clearly explained with reference to detailed description, claims and drawings of the present invention as follows.

In one aspect, the present invention provides a nucleic acid molecule encoding a Gle1 protein variant, wherein a Gle1 protein comprising a phytic acid-binding pocket represented by General Formula 1, Leu-Leu-Ala-Glu-Xaa1-Xaa2-Xaa3-Xaa4-Cys-Xaa5-Tyr-Thr-Val-Pro           [General Formula 1]

(wherein Xaa1 is Leu or Phe, Xaa2 is His or Asn, Xaa3 is Lys or Arg, Xaa4 is Ala or Val, and Xaa5 is Ile or Met) (SEQ ID NO: 18).

wherein the Gle1 protein variant comprising the phytic acid-binding pocket of General Formula 1 in which one or more residues selected from the group consisting of the Xaa4 residue and the Glu residue is substituted with a basic amino acid.

The inventors have attempted to develop a novel method for solving problems such as low seed productivity and germination frequency, shown in low-InsP$_6$-containing crops. As a result, it was identified that InsP$_6$ serves to control mRNA export as a cofactor of Gle1 in plants, and confirmed that Gle1 variants with increased affinity to InsP$_6$ allowe mRNA export to normally occur in low-InsP$_6$-containing plants, resulting in effectively rescuing low growth and low yields. In addition, the inventors have reported that Gle1-InsP$_6$ serves as an activator of LOS4 ATPase/RNA helicase involved in mRNA export in plants, supporting the Gle1-InsP$_6$-Dbp5 (LOS4 homolog) paradigm proposed in yeast.

According to the present invention, *Arabidopsis thaliana* Gle1 variants with mutations that increase the basic charge on an InsP$_6$-binding surface show increased sensitivity to InsP$_6$ concentrations with respect to the stimulation of LOS4 ATPase activity in vitro, and expression of the Gle1 variants with the increased InsP$_6$ sensitivity rescues the mRNA export defect in an ipk1 InsP$_6$-deficient mutant, and highly increases vegetative growth, seed yield and seed performance of the mutants.

In the present invention, according to alignment of amino acid residues of the InsP$_6$-binding pocket of the Gle1 domain in the Gle1 protein (FIGS. 10B and 15A), it was confirmed that the residues are highly conserved between fungi (*Saccharomyces cerevisiae* (Sc) and *Candida albicans* SC5314 (Ca)), vertebrates (*Homo sapiens* (Hs), *Mus musculus* (Mm), *Danio rerio* (Dr) and *Bos taurus* (Bt)), dicotyledonous plants (*Arabidopsis thaliana* (At), *Glycine max* (Gm), *Vitis vinifera* (Vv), *Populus trichocarpa* (Pt1), *Nicotiana benthamiana* (Nb) and *Ricinus communis* (Rc)), monocotyledonous plants (*Oryza sativa* (Os), *Zea mays* (Zm), *Hordeum vulgare* (Hv), *Triticum aestivum* (Ta), *Sorghum bicolor* (Sb) and *Brachypodium distachyon* (Bd)), and gymnosperms (*Pinus teada* (Pt2)). The Gle1 protein containing the amino acid sequence of the InsP$_6$-binding pocket may be derived from a plant.

The plants may be dicotyledonous plants or monocotyledonous plants. In addition, the dicotyledonous plants comprise *Arabidopsis thaliana* (At) and *Glycine max* (Gm). In addition, the monocotyledonous plants comprise *Oryza sativa* (Os), *Zea mays* (Zm), *Hordeum vulgare* (Hv), *Triticum aestivum* (Ta) and *Sorghum bicolor* (Sb).

The term "nucleic acid molecule" used herein broadly encompasses DNA and RNA molecules. Nucleotides which are basic components of the nucleic acid molecule comprise analogs having modified sugar moieties or base moieties as well as natural nucleotides (Scheit, Nucleotide Analogs, John Wiley, New York (1980); Uhlman and Peyman, Chemical Reviews, 90:543-584 (1990)). The "nucleic acid molecule" used herein is interchangeably used with "polynucleotide."

The term "nucleic acid sequence" used herein refers to the sequence of nucleotides which are the basic components of the nucleic acid molecule.

There are mutations in nucleotides, which do not result in changes in proteins. The nucleic acid molecule of the present invention comprises functionally equivalent codons, codons coding for the same amino acids (e.g., due to codon degeneracy, six codons for arginine or serine), or codons coding for biologically equivalent amino acids.

In consideration of the above-described mutations with biologically equivalent activities, the nucleic acid molecule used in the present invention is interpreted to comprise sequences with substantial identity to the sequences set forth in the sequence listing. The sequences with substantial identity refer to sequences that are aligned to correspond as much as possible to a random sequence different from the above-described sequence of the present invention, and have preferably at least 60%, more preferably 70%, further more preferably 80%, and most preferably 90% homology when being analyzed using an algorithm conventionally used in the art. Alignment methods for sequence comparison are well known in the art. Various methods and algorithms for alignment are disclosed in Smith and Waterman, Adv. Appl. Math. 2:482 (1981) Needleman and Wunsch, J. Mol. Bio. 48:443 (1970); Pearson and Lipman, Methods in Mol. Biol. 24: 307-31 (1988); Higgins and Sharp, Gene 73:237-44 (1988); Higgins and Sharp, CABIOS 5:151-3 (1989); Corpet et al., Nuc. Acids Res. 16:10881-90 (1988); Huang et al., Comp. Appl. BioSci. 8:155-65 (1992) and Pearson et al., Meth. Mol. Biol. 24:307-31 (1994). The National Center for Biological Information (NBCI) basic local alignment search tool (BLAST) (Altschul et al., J. Mol. Biol. 215:403-10 (1990)) is accessible from NBCI or the like, and can be used in combination with sequencing programs such as blastp, blasm, blastx, tblastn and tblastx on the Internet. BLSAT is accessible at www.ncbi.nlm.nih.gov/BLAST/. A method of comparing sequence homology using this program can be found at www.ncbi.nlm.nih.gov/BLAST/blast_help.html.

According to an exemplary embodiment of the present invention, a nucleic acid molecule of the present invention may encode a Gle1 protein variant comprising a phytic acid-binding pocket of General Formula 1 in which one or more residues selected from the group consisting of Xaa4 and Glu residues in is substituted with a basic amino acid. Preferably, the nucleic acid molecule of the present invention may encode a Gle1 protein variant comprising a phytic acid-binding pocket of General Formula 1 in which the Xaa4 residue is substituted with a basic amino acid, or the nucleic acid molecule may encode Gle1 protein variants comprising a phytic acid-binding pocket of General Formula 1 in which both of the Glu and Xaa4 residues are respectively substituted with basic amino acids.

According to another exemplary embodiment of the present invention, in the amino acid sequence of the InsP$_6$-binding pocket, represented by General Formula 1, comprised in the preferable Gle1 protein, Xaa1 may be Leu, Xaa2 may be His, Xaa3 may be Arg, Xaa4 may be Ala, and Xaa5 may be Ile. The Gle1 protein including the InsP$_6$-binding pocket of the sequence may be derived from legumes (soybeans, *Glycine max*, etc.). Accordingly, the nucleic acid molecule of the present invention comprises a nucleic acid sequence encoding a protein variant including an InsP$_6$-binding pocket in which the 4$^{th}$ residue (Glu) and/or the 8$^{th}$ residue (Ala) in an amino acid sequence of SEQ ID NO: 13 is/are substituted with basic amino acid(s). The nucleic acid molecule of the present invention may also comprise a nucleic acid sequence encoding a Gle1 protein variant in which Glu 447 and/or Ala 451 in the amino acid sequence (XP_006591482) of the Gle1 protein of *Glycine max* is/are substituted with basic amino acid(s).

According to an exemplary embodiment of the present invention, in the amino acid sequence of the InsP$_6$-binding pocket, represented by General Formula 1, comprised in the preferable Gle1 protein, Xaa1 may be Phe, Xaa2 may be His, Xaa3 may be Arg, Xaa4 may be Val, and Xaa5 may be Met. The Gle1 protein including the InsP$_6$-binding pocket of the sequence may be derived from rice (*Oryza sativa*). Accordingly, the nucleic acid molecule of the present invention comprises a nucleic acid sequence encoding a protein variant including an InsP$_6$-binding pocket in which the 4$^{th}$ residue (Glu) and/or the 8$^{th}$ residue (Val) in an amino acid sequence of SEQ ID NO: 14 is/are substituted with basic amino acid(s). The nucleic acid molecule of the present invention may comprise a nucleic acid sequence encoding a Gle1 protein variant in which Glu 542 and/or Val 546 in an amino acid sequence (Os; EEC73520.1) of the Gle1 protein of *Oryza sativa* is/are substituted with basic amino acid(s).

According to another exemplary embodiment of the present invention, in the amino acid sequence of the InsP$_6$-binding pocket, represented by General Formula 1, comprised in the preferable Gle1 protein, Xaa1 may be Phe, Xaa2 may be Asn, Xaa3 may be Arg, Xaa4 may be Val, and Xaa5 may be Ile. The Gle1 protein including the $InsP_6$-binding pocket of the sequence may be derived from maize (*Zea mays*). Accordingly, the nucleic acid molecule of the present invention comprises a nucleic acid sequence encoding a protein variant including an $InsP_6$-binding pocket in which the $4^{th}$ residue (Glu) and/or the $8^{th}$ residue (Val) in an amino acid sequence of SEQ ID NO: 15 is/are substituted with basic amino acid(s). The nucleic acid molecule of the present invention may comprise a nucleic acid sequence encoding a Gle1 protein variant in which Glu 455 and/or Val 459 in the amino acid sequence (Zm; AFW67255.1) of the Gle1 protein of *Zea mays* is/are substituted with basic amino acid(s).

According to still another exemplary embodiment of the present invention, in the amino acid sequence of the $InsP_6$-binding pocket, represented by General Formula 1, included in the preferable Gle1 protein, Xaa1 may be Phe, Xaa2 may be Asn, Xaa3 may be Lys, Xaa4 may be Val, and Xaa5 may be Met. The Gle1 protein including the $InsP_6$-binding pocket of the sequence may be derived from barley (*Hordeum vulgare*) or wheat (*Triticum aestivum*). Accordingly, the nucleic acid molecule of the present invention comprises a nucleic acid sequence encoding a protein variant including an $InsP_6$-binding pocket in which the $4^{th}$ residue (Glu) and/or the $8^{th}$ residue (Val) in any one of the amino acid sequences of SEQ ID NO: 16 and 17 is/are substituted with basic amino acid(s). In addition, the nucleic acid molecule of the present invention comprises a nucleic acid sequence encoding a protein variant including an $InsP_6$-binding pocket in which Glu 436 and/or Val 440 in the amino acid sequence (Hv; BAJ99175.1) of the Gle1 protein of *Hordeum vulgare* is/are substituted with basic amino acid(s). The nucleic acid molecule of the present invention may comprise a nucleic acid sequence encoding a Gle1 protein variant in which Glu 438 and/or Val 442 in the amino acid sequence (Ta; W5GX62) of the Gle1 protein of *Triticum aestivum* is/are substituted with basic amino acid(s).

According to yet another exemplary embodiment of the present invention, in the amino acid sequence of the $InsP_6$-binding pocket, represented by General Formula 1, included in the preferable Gle1 protein, Xaa1 may be Phe, Xaa2 may be His, Xaa3 may be Lys, Xaa4 may be Ala, and Xaa5 may be Ile. The Gle1 protein including the $InsP_6$-binding pocket of the sequence may be derived from *Arabidopsis*. The nucleic acid molecule of the present invention comprises a nucleic acid sequence encoding a protein variant in which Glu 433 and/or Ala 447 in a sequence set forth in SEQ ID NO: 2 is/are substituted with basic amino acid(s). The nucleic acid molecule of the present invention preferably comprises a nucleic acid sequence encoding a protein variant in which the Aka 437 residue, or the Glu 433 residue and the Ala 437 residue is/are substituted with basic amino acid(s).

In the present invention, an acidic or neutral amino acid residue of the $InsP_6$-binding pocket of the Gle1 protein is substituted with a basic amino acid to increase the sensitivity of the Gle1 protein in plants and thus improve the growth of low-phytate plants. The basic amino acid used in the present invention may achieve the same effect using Lys, Arg or His, and preferably Lys.

In another aspect, the present invention provides Gle1 protein variants coded by the above-described nucleic acid molecules of the present invention, respectively.

The Gle1 protein variant coded by the above-described nucleic acid molecules of the present invention also comprises Gle1 protein variants of different plant species as long as the variants elevate the sensitivity of the Gle1 protein in plants by substituting a specific amino acid (acidic or neutral) residue with a basic amino acid on the basis of the highly-conserved sequence of the $InsP_6$-binding pocket of the Gle1 protein.

In still another aspect, the present invention provides gene delivery systems including the above-described Gle1 protein variant-encoding nucleic acid molecule.

The gene delivery system may be a recombinant vector for plant expression.

According to another exemplary embodiment of the present invention, the gene delivery system is a recombinant vector for plant expression, which comprises (a) the Gle1 protein variant-encoding nucleic acid molecule of the present invention described above; (b) a promoter operatively linked to the nucleic acid molecule and forming an RNA molecule in plant cells; and (c) a poly A signal sequence acting in plant cells to cause polyadenylation at the 3' end of the RNA molecule.

The term “operatively linked” refers to functional binding between a nucleic acid expression regulatory sequence (e.g., an array of a promoter, a signal sequence, or an array of transcriptional regulatory factor-binding sites) and a different nucleic acid sequence, and therefore, the regulatory sequence regulates transcription and/or translation of the different nucleic acid sequence.

A vector system of the present invention may be constructed by various methods known in the art, and a specific method for constructing the vector system is disclosed in Sambrook et al. Molecular Cloning, A Laboratory Manual, Cold Spring Harbor Laboratory Press (2001).

The suitable promoter used in the present invention may be any one conventionally used in the art for the introduction of a gene to a plant, and comprises, for example, a seed or embryo-specific promoter (Ole or Glb promoter), a SP6 promoter, a T7 promoter, a T3 promoter, a PM promoter, a maize ubiquitin promoter, a cauliflower mosaic virus (CaMV) 35S promoter, a nopaline synthase (nos) promoter, a Figwort mosaic virus 35S promoter, a sugarcane bacilliform virus promoter, a commelina yellow mottle virus promoter, a photo-inducible promoter of a small subunit of ribulose-1,5-bis-phosphate carboxylase (ssRUBISCO), a cytosolic triosphosphate isomerase (TPI) promoter in rice, or an adenine phosphoribosyltransferase (APRT) or octopine synthase promoter in *Arabidopsis*.

According to still another exemplary embodiment of the present invention, the suitable poly A signal sequence causing 3'-end polyadenylation in the present invention comprises the nos 3'-end derived from the nopaline synthase gene of *Agrobacterium tumefaciens* (Bevan et al. Nucleic Acids Research, 11(2):369-385 (1983)), the ocs 3'-end derived from the octopine synthase gene of *Agrobacterium tumefaciens*, the 3' end region of the protease I or II gene of tomatoes or potatoes, or a CaMV 35S terminator or octopine synthase (OCS) terminator sequence.

Optionally, the vector additionally delivers genes encoding reporter molecules (e.g., luciferase and β-glucuronidase). In addition, the vector of the present invention comprises an antibiotic (e.g, neomycin, carbenicillin, kanamycin, spectinomycin, hygromycin, etc.)-resistant gene (e.g., neomycin phosphotransferase (npt II), hygromycin phosphotransferase (hpt), etc.) as a selectable marker.

According to another exemplary embodiment of the present invention, the recombinant vector for plant expression of the present invention is an *Agrobacterium* binary vector.

The term "binary vector" used herein refers to a vector divided into two plasmids consisting of a plasmid having a left border (LB) and a right border (RB), which are necessary for mobility in a tumor inducible (Ti) plasmid, and a plasmid containing genes necessary for transferring target nucleotides. The *Agrobacterium* for transformation of the present invention may be any one that is suitable for the expression of the nucleotide sequence of the present invention, and particularly, the *Agrobacterium* strain for plant transformation in the present invention is preferably *Agrobacterium tumefaciens* C58C1.

A method of introducing the recombinant vector of the present invention into *Agrobacterium* may be performed by various methods known in the art, including, for example, particle bombardment, electroporation, transfection, a lithium acetate method and heat shock.

In the present invention, abiotic stress comprises dry stress, low-temperature stress, or salt stress, and more preferably salt stress. According to the present invention, the inventors confirmed that Gle1 variant seeds retain normal sensitivity to the salt stress.

In yet aspect, the present invention provides a composition for increasing seed yield, germination, growth, or abiotic stress tolerance in plants, which includes the above-described gene delivery system containing the above-described nucleic acid molecule encoding the Gle1 protein variant of the present invention as an active ingredient.

The composition may be used to change the phenotype of a plant by introducing a gene or nucleic acid molecule into the plant.

According to an exemplary embodiment of the present invention, the plant is preferably an $InsP_6$-deficient plant. When $InsP_6$ is contained at a low concentration in the plant, a problem of unfavorable plant growth occurs. Therefore, when the nucleic acid molecule of the present invention that can encode the Gle1 protein variant of the present invention is introduced into such $InsP_6$-deficient plant, the seed yield of the $InsP_6$-deficient plant may be increased, the germination and growth may be promoted, or the tolerance to abiotic stress may be increased.

In yet another aspect, the present invention provides transgenic plant cells into which the nucleic acid molecule of the present invention is introduced. The plant cells may be transformed by the gene delivery system of the present invention.

In yet another aspect, the present invention provides a transgenic plant into which the nucleic acid molecule of the present invention is introduced. The plant may be transformed by the gene delivery system of the present invention. To prepare the transgenic plant cells and transgenic plant of the present invention, a method generally known in the art (Ray Wu, Lawrence Grossman, Methods of Enzymology, Vol. 153, pages 3-622 (1987)) may be used. A plant may be transformed by inserting an exogenous polynucleotide into a delivery system such as a plasmid or virus vector. To this end, *Agrobacterium* bacteria may be used as a mediator (Chilton et al. Cell 11:263:271 (1977)), or an exogenous polynucleotide may be directly introduced into plant cells (Lorz et al. Mol. Genet. 199:178-182; (1985)). For example, electroporation, microparticle bombardment, or polyethylene glycol-mediated uptake may be used when a vector without a T-DNA site is used.

Generally, for plant transformation, methods of infecting plant cells or seeds with *Agrobacterium tumefaciens* transformed with an exogenous polynucleotide are widely used (U.S. Pat. Nos. 5,004,863, 5,349,124 and 5,416,011). Transgenic plant cells or seeds may be cultured under suitable conditions known to those of ordinary skill in the art to grow plants.

It is construed that the term "plant(s)" used herein comprises all of mature plants, and plant cells, plant tissues and plant seeds that can be grown to mature plants.

When the nucleic acid molecule of the present invention is introduced or applied to plants, compared to a wild type, sensitivity and binding strength with respect to plant $InsP_6$ may be improved, and thus the transgenic plant is improved in growth efficiency, seed yield, germination frequency and stress tolerance. Particularly, even in an environment containing a low concentration of $InsP_6$, the sensitivity to $InsP_6$ is maintained at a high level, the growth, seed yield, germination frequency and/or abiotic stress tolerance of plants may be improved or increased.

The plant to which the method of the present invention may be applied is not particularly limited. Plants to which the method of the present invention is applied may comprise almost all of dicotyledonous plants including lettuce, napa cabbage, potatoes and white radishes and monocotyledonous plants including rice, barley, banana, etc. Particularly, when the method of the present invention is applied to edible vegetables or fruits exhibiting a rapid deterioration of quality by aging due to thin skins, like tomatoes; and plants having leaves as main products for commerce, it is effective in increasing storage efficiency. The present invention is preferably applied to plants selected from the group consisting of food crops including rice, wheat, barley, maize, beans, potatoes, red bean, oat, and sorghum; vegetable crops including *Arabidopsis*, napa cabbage, white radish, peppers, strawberry, tomatoes, watermelon, cucumber, cabbage, oriental melon, pumpkin, welsh onion, onion, and carrot; special crops including ginseng, tobacco, cotton, sesame, sugar cane, sugar beet, perilla, peanut and canola; fruit trees including apple, pear, jujube, peach, kiwi, grape, tangerine, persimmon, plum, apricot and banana trees; flowers including rose, gladiolus, gerbera, carnation, chrysanthemum, lily and tulip; and feed crops including ryegrass, red clover, orchard grass, alfalfa, tall fescue and perennial ryegrass. More preferably, the plants are rice, wheat, barley, maize, legume, potato, red bean, oat, sorghum or *Arabidopsis*, and further more preferably, the plants are rice, wheat, barley, maize, legume, sorghum or *Arabidopsis*.

According to an exemplary embodiment of the present invention, the plant may be an $InsP_6$-deficient plant. When the nucleic acid molecule of the present invention is introduced into an $InsP_6$-deficient plant, it was experimentally confirmed that the growth, seed yield, germination frequency and/or abiotic stress tolerance of the plant is improved.

The term "$InsP_6$-deficient plants" comprise identified or unidentified low-phytic acid (lpa) mutants, and for example, the $InsP_6$-deficient plants are plants containing an inactivated myo-inositol-3-phosphate synthase (MIPS) gene, myo-inositol kinase (MIK), inositol polyphosphate kinase (IPK) gene or multidrug resistance-associated (MRP) ATP-binding cassette transporter gene, but the present invention is not limited thereto. In the specification, this term is interchangeably used with "low-$InsP_6$ plants."

The term "inactivation" use herein refers to a state in which a gene is mutated to prevent the generation of a functional protein that will be produced when the gene is expressed.

For example, an inactivated MIK gene comprises an imperfect form of a protein coded by the MIK gene, a form with imperfect activity, a truncated form or non-formation of a protein. The inactivation comprises inhibition of the functional expression of one or more genes. Gene inactivation may comprise deletion, disruption of a protein-coding sequence, insertion, addition, substitution, mutation or seed-specific gene silencing (e.g., RNAi).

Additionally, the term "inactivity" used herein is induced by the above-described "inactivation." According to some exemplary embodiments, due to the inactivated gene, a measureable change in the activity of a gene or a gene product may not be shown. According to some exemplary embodiments, the functional expression of a gene may not be shown or slightly shown by the inactivated gene.

In yet another aspect, the present invention provides a method of increasing seed yield, promoting germination and growth or increasing abiotic stress tolerance in plants, which comprises increasing $InsP_6$ sensitivity of the Gle1 protein in plants.

That is, the present invention provides a method of increasing seed yield, promoting germination or growth, or increasing abiotic stress tolerance, which comprises introducing a gene delivery system containing a Gle1 protein variant-encoding nucleic acid molecule of the present invention into plants.

The method may further comprise selecting a transgenic plant exhibiting the phenotype with increased seed yield, germination performance, growth performance or abiotic stress tolerance compared to a wild type.

The plants comprise all of mature plants, and plant cells, plant tissue and plant seeds that can be grown to mature plants, and details on the plants other than the types of the plants are the same as described above.

The transgenic plant into which the nucleic acid molecule of the present invention is introduced has an ability to be grown in a stress environment where the content of $InsP_6$ is very low. That is, the transgenic plant may have higher growth activity, seed germination frequency and seed yield, or higher tolerance to abiotic stresses than the wild type due to increased sensitivity to $InsP_6$ even in an environment in which $InsP_6$ is present at a low content. Particularly, when the $InsP_6$-deficient plant is transformed using the nucleic acid molecule of the present invention, it has an excellent effect of increasing seed yield, promoting germination or growth, or increasing abiotic stress tolerance of the plant. The inventors examined plant growth at a low $InsP_6$ concentration after a plant was transformed by the Gle1 protein variant-encoding nucleic acid molecule of the present invention. As a result, it was experimentally confirmed that the transgenic plant of the present invention is more excellent in growth activity than comparative groups.

A method of introducing target nucleotides or a recombinant vector for plant expression containing the same into plant cells may be performed by various methods known in the art.

Selection of the transgenic plant cells may be performed by exposing the transgenic culture to a selection agent (e.g., a metabolic inhibitor, an antibiotic and an herbicide). Plant cells which stably contain a marker gene providing tolerance to a selection agent are grown in one culture and then divided. Exemplary markers comprise a hygromycin phosphotransferase gene, a glycophosphate-resistant gene and a neomycin phosphotransferase (nptII) system, but the present invention is not limited thereto. A method of developing or redifferentiating a plant from a plant protoplasts or various explants are well known in the art. The development or redifferentiation of the plant containing a foreign gene introduced by *Agrobacterium* may be achieved according to a method known in the art (U.S. Pat. Nos. 5,004,863, 5,349,124 and 5,416,011).

The nucleotide, plant expression vector and the transforming method thereof, which are used in the present invention, have been described above, and thus the descriptions will be omitted without avoiding excessive complexity of the specification due to repeated descriptions.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIGS. 1A, 1B, 1C, 1D and 1E show the result of analyzing the Gle1-silencing phenotype of *Arabidopsis* using DEX-inducible RNAi:

FIG. 1A shows plant phenotypes of two different *Arabidopsis* DEX-inducible Gle1 RNAi lines [Gle1 (N) and Gle1 (C) RNAi] with respect to DEX treatment. The plants were grown in soil for 14 days, and then sprayed with ethanol (−) or 30 μM DEX (+) for 7 days;

FIG. 1B shows in situ hybridization of leaves of the two Gle1 RNAi lines after sprayed with ethanol (−) or 30 μM DEX (+) for 7 days using a Cy3-oligo-dT probe for confocal microscopy;

FIG. 1C shows seedling phenotypes of the two Gle1 RNAi lines grown for 10 days on an MS medium containing ethanol (−) or 10 μM DEX (+);

FIG. 1D shows the result of real-time quantitative RT-PCR analysis for determining Gle1 transcript levels. The transcript levels in (+)DEX samples are expressed relative to the transcript levels in (−)DEX samples. UBC10 mRNA levels are used as a control. The values are expressed as mean±SD of an experiment repeated 3 times. Asterisks represent statistical significance of the differences between the (−)DEX and (+)DEX samples (*, $P \leq 0.05$; **, $P \leq 0.01$); and FIG. 1E shows the result of western blotting with anti-Gle1 antibodies for determining endogenous Gle1 protein levels. Coomassie blue-stained rbcL (Rubisco large subunit) is used as a control;

FIGS. 2A, 2B and 2C show the subcellular localization of Gle1. The GFP signal in the nuclear envelope is marked with an arrowhead (Δ):

FIG. 2A shows the result in which a DNA construct encoding GFP-Gle1 under the control of CaMV35S promoter is expressed in *N. benthamiana* leaves through agroinfiltration. Mesophyll protoplasts of the infiltrated leaves and GFP fluorescence in epidermal cells are observed by confocal microscopy;

FIG. 2B shows the result in which tobacco BY-2 cells are fixed, double-labeled with anti-Gle1 antibodies (red) and anti-α-tubulin antibodies (green), and stained with DAPI for confocal microscopy; and FIG. 2C shows the result in which GFP fluorescence in root cells of *Arabidopsis* transgenic plants designed with Gle1p::GFPGle1, which expressed GFP-Gle1 under an endogenous Gle1 promoter (1,944 bp upstream of the initiation codon), is observed by confocal microscopy. Two independent transgenic lines (lines #13 and #21) are analyzed;

FIGS. 3A, 3B, 3C, 3D and 3E show the interaction between LOS4 and Gle1:

FIG. 3A shows that phenotypes and leaves of los4-1 mutants grown for 3 weeks in soil, compared with a wild type;

FIG. 3B shows in situ hybridization of los4-1 mutant leaves with a Cy3-oligo-dT probe for confocal microscopy;

FIG. 3C shows the result of bimolecular fluorescence complementation (BiFC) to visualize the interaction between Gle1 and LOS4. YFP$^N$- and YFP$^C$-fusion proteins are expressed in N. benthamiana leaves by agroinfiltration. YFP fluorescence in mesophyll protoplasts prepared from the infiltrated leaves is examined by confocal microscopy. An arrowhead (Δ) indicates the nucleus;

FIG. 3D shows the result of co-immunoprecipitation of Gle1 and LOS4. After agroinfiltration was performed to co-express Flag-Gle1 and LOS4-Myc proteins, total leaf proteins are co-immunoprecipitated with anti-Flag antibodies, and co-immunoprecipitates are detected by anti-Myc antibodies; and FIG. 3E shows pull-down assays showing the direct interaction between Gle1 and LOS4. Purified recombinant proteins are stained with Coomassie blue (left). A mixture of the proteins is bound to a nickel resin or amylose resin, and the resin-bound proteins are eluted and then stained with Coomassie blue (right);

FIGS. 4A, 4B, 4C, 4D, 4E, 4F and 4G show the result of stimulation of LOS4 activity by Gle1:

FIG. 4A shows the sequence alignment of key residues of an InsP$_6$-binding pocket of Gle1 and its variants (IS1, IS2, and ID) (SEQ ID NO: 21). The key residues are boxed. Modified residues in the mutants are shown as red, and the residues shown as red are the residue 437 of Gle1 (IS1) (SEQ ID NO: 22), the residues 433 and 437 of Gle1 (IS2) (SEQ ID NO: 23), and the residue 436 of Gle1 (ID) (SEQ ID NO: 24);

FIG. 4B shows the result in which purified recombinant proteins are stained with Coomassie blue. Gle1C indicates the C-terminal region of Gle1 (amino acid residues 244 to 611);

FIG. 4C shows the result of a steady-state ATPase assay performed with 1 μM LOS4-His, 2 mM ATP and 50 μg/μl polyadenylic acid (RNA) in the presence of 0, 0.5, 1, 2 and 4 μM MBP-Gle1C;

FIG. 4D shows the result of stimulation of the activity of LOS4 ATPase by Gle1C. The steady-state ATPase assay is performed with 1 μM LOS4-His and 2 μM MBP-Gle1C in the presence of 0-2 mM ATP. Data points are expressed as mean±SD of an experiment repeated 3 times;

FIG. 4E shows k$_{cat}$ values of LOS4-His in the absence or presence of MBP-Gle1C;

FIG. 4F shows the dependence of LOS4 ATPase activity on RNA concentration. An ATPase assay is performed using 1 μM LOS4-His and 2 mM ATP in the absence (●) or presence (■) of 2 μM MBP-Gle1C with different RNA concentrations; and FIG. 4G shows the result of an in vitro nucleic acid-melting assay using 78 nucleotide-long, 9-bp-containing, hairpin-shaped molecular beacons with different ratios of LOS4-His and MBP-Gle1 (full-length) proteins (■-LOS4: Gle1 (1:4), ◆-LOS4:Gle1 (1:2), ▲-LOS4:Gle1 (1:1), ●-LOS4 only, X-control). Beacon fluorescence is measured by fluorescence spectrophotometry;

FIGS. 5A, 5B, 5C, 5D, 5E, 5F and 5G show Gle1 and Gle1 variants for the stimulation of LOS4 ATPase activity:

FIG. 5A shows InsP$_6$ and InsP$_6$-binding regions of human Gle1 and Arabidopsis Gle1 and its variants (IS1, IS2 and ID), which are predicted on the basis of the structure of the yeast Gle1 domain. The electrostatic surface potential is shown: acidic, basic and neutral residues are shown in red, blue (the darkest region) and white, respectively. FIG. 5A shows the dark gray region is basic (blue), the light gray region is acid (red), and the white region is neutral in the protein structure in a black-and-white diagram;

FIG. 5B shows relative ATPase activity of LOS4 with different combinations of cofactors. An ATPase assay is performed with 1 μM LOS4-His and 2 mM ATP in the absence or presence of cofactors: 2 μM MBP-Gle1 (full length), 50 μg/μl polyadenylic acid (RNA), 10 μM InsP$_6$, and 10 μM InsS$_6$. The values in FIGS. 5B to 5G are expressed as mean±SD of an experiment repeated 3 times;

FIG. 5C shows the stimulation of LOS4 ATPase activity by Gle1 and Gle1 variants in the absence of InsP$_6$. An ATPase assay is performed with 1 μM LOS4-His, 2 mM ATP and 50 μg/μl RNA in the presence of 2 μM concentration of MBP-Gle1C or MBP-Gle1C variant; and FIGS. 5D to 5G show InsP$_6$ sensitivity of Gle1 and Gle1 variants with respect to LOS4 stimulation. An ATPase assay is performed in the presence of different InsP$_6$ concentrations as described in FIG. 5C;

FIGS. 6A, 6B, 6C, 6D, 6E, 6F and 6G show phenotypes of transgenic Arabidopsis plants expressing Gle1 and Gle1 variants in an ipk1-1 background:

FIG. 6A shows the subcellular localization of GFP-Gle1, GFP-IS1 and GFP-IS2 in epidermal cells of N. benthamiana. A GFP signal in the nuclear membrane is marked with an arrowhead (Δ) (Scale bar=50 μm);

FIG. 6B shows the result of western blotting with anti-GFP antibodies for determining expression levels of GFP-Gle1, GFPIS1 and GFP-IS2 in independent transgenic lines. Coomassie blue-stained rbcL is used as a control;

FIG. 6C shows improved vegetative growth of the ipk1-1 mutant by expression of the Gle1 variant. Plants were grown for 3 weeks in soil;

FIG. 6D shows a fluorescence emission spectrum for chlorophyll measurement. Spectrofluorometry of the chlorophylls is performed using a fluorescence spectrophotometer;

FIG. 6E shows phenotypes of plants grown for 6 weeks in soil; and

FIG. 6F shows in situ hybridization performed with leaves of the plants using a Cy3-oligo-dT probe;

FIGS. 7A, 7B, 7C, 7D and 7E show seed phenotypes of transgenic plants expressing Gle1 and Gle1 variants:

FIG. 7A shows the morphology of mature dry seeds (Scale bar=1 mm);

FIG. 7B shows seed mass and seed yield. The values are expressed as mean±SD from 12 independent plants for each line;

FIG. 7C shows seed germination frequencies on an MS medium (n=200);

FIG. 7D shows seed germination frequencies on a MS medium containing 200 mM NaCl (n=200) (X (black): WT, ◆ (red): ipk1-1, ▲ (ocher): GFP-Gle1, ● (purple): GFP-IS1, ■ (green): GFP-IS2); and FIG. 7E shows the contents of seed InsP$_6$ and free phosphate (Pi) based on HPIC analyses. The values are expressed as mean±SD of an experiment repeated 3 times;

FIGS. 8A, 8B and 8C show the interaction between IPK1 and LOS4:

FIG. 8A shows the IPK1-GFP fusion protein expressed in N. benthamiana leaves by agroinfiltration for confocal microscopy. The GFP signal in the nuclear envelope is marked with an arrowhead (Δ) (Scale bar=50 μm);

FIG. 8B shows BiFC-mediated visualization of the IPK1-LOS4 interaction. An YFP signal in the nuclear envelope is shown with an arrowhead (Δ) (Scale bar=50 μm); and FIG. 8C shows protein expression in the BiFC analysis shown in FIG. 8B. The expression of YFP$^N$- and YFP$^C$-fusion proteins in the infiltrated *N. benthamiana* leaves is determined by western blotting with anti-GFP antibodies;

FIG. 9 shows the phylogenetic tree of Gle1. The phylogenetic tree of Gle1-related sequence from eukaryotes is based on the "MEGA" program (version 5.2.2; www.mega-software.net/). The tree branches are labeled with a bootstrap score based on 3,000 bootstrap replicates. The scale bar represents 0.2 amino acid substitutions per site in the primary structure;

FIGS. 10A and 10B show the protein structure and sequence alignment of Gle1:

FIG. 10A shows a schematic diagram of the predicted protein structure of *Arabidopsis* Gle1. The Gle1 domain is marked. The "aa" indicates an amino acid; and FIG. 10B shows multispecies sequence alignment of the Gle1 domains: *Saccharomyces cerevisiae* (Sc; CAA98785.1), *Candida albicans* SC5314 (Ca; XM_710903.1), *Homo sapiens* (Hs; NP_001003722.1), *Mus musculus* (Mm; NP_083199.1), *Danio rerio* (Dr; NP_001003885.1), *Bos taurus* (Bt; DAA24190.1), *Arabidopsis thaliana* (At; At1g13120), *Vitis vinifera* (Vv; XP_002282194.2), *Populus trichocarpa* (Pt1; XP_002311751.2), *Glycine max* (Gm; XP_006591482), *Nicotiana benthamiana* (Nb; NbS00025743g0004.1), *Ricinus communis* (Rc; EEF47610.1), *Oryza sativa* (Os; EEC73520.1), *Zea mays* (Zm; AFW67255.1), *Hordeum vulgare* (Hv; BAJ99175.1), *Triticum aestivum* (Ta; W5GX62), *Sorghum bicolor* (Sb; EER90667.1), *Brachypodium distachyon* (Bd; XP_003567589.1), and *Pinus teada* (Pt2; 2A_all_VO_L_8172_T_13/18) (SEQ ID NO: 25 to SEQ ID NO: 43, respectively). Residues conserved between the sequences are boxed in black, dark gray or light gray based on the degree of conservation. The red box indicates the region containing some key residues of the InsP$_6$-binding pocket shown in FIG. 16;

FIGS. 11A, 11B, 11C and 11D show the result of analysis of Gle1-silencing phenotypes using VIGS in *N. benthamiana*:

FIG. 11A is a schematic diagram showing the NbGle1 cDNA region used in a VIGS construct. The gray box indicates the protein-coding region of NbGle1. For VIGS, 615 bp N-terminal and 570 bp C-terminal NbGle1 cDNA fragments (marked with bars) are cloned into the TRV-based VIGS vector pTV00. *Agrobacterium* containing TRV or a TRV:NbGle1 construct is infiltrated into *N. benthamiana* plants. The "aa" indicates amino acid;

FIG. 11B shows plant phenotypes of NbGle1 (N) and bGle1 (C) VIGS lines compared with those of TRV control. The plants are photographed 14 days after infiltration;

FIG. 11C shows the result of western blotting with anti-Gle1 antibodies for determining endogenous NbGle1 protein levels of VIGS plants. Coomassie blue-stained rbcL is used as a control; and FIG. 11D shows the result of in situ hybridization of the VIGS plants using a 45-nucleotide oligo (dT) probe labeled with Cy3 (Cy3-oligo-dT) at its end for confocal laser scanning microscopy. A nucleus is visualized by DAPI staining;

FIG. 12 shows the result of protein expression in a BiFC analysis. Expression of YFP$^N$- and YFP$^C$-fusion proteins in infiltrated *N. benthamiana* leaves was determined by western blotting with anti-GFP antibodies;

FIGS. 13A and 13B show the results of control experiments for an ATPase assay:

FIG. 13A shows the ATPase assay performed with MBP-Gle1C (2 μM); and

FIG. 13B shows the ATPase assay performed with LOS4-His (1 μM) and MBP fusion proteins of full-length Gle1 or Gle1C (2 μM);

FIG. 14 shows computational modeling of the Gle1 domain. The tertiary structures of the Gle1 domain from human Gle1, and *Arabidopsis* Gle1 and its variants (IS1, IS2 and ID) were predicted using an automated homology modeling server "SWISS-MODEL (swissmodel.expasy.org/interactive)" with the Gle domain of yeast Gle1 as a template. Electrostatic surface potentials are shown: acidic, basic, and neutral residues are shown in red, blue and white, respectively. InsP$_6$ binding to the InsP$_6$-binding surface of Gle1 is shown. The predicted molecular model is edited using a PyMOL molecular graphic system (version 1.1) and checked with the ResProx program (www.resprox.ca/). The predicted resolutions of the human Gle1 domain and *Arabidopsis* Gle1 domain are 2.785 and 5.889, respectively, according to the ResProx program. The PDB file name for the yeast Gle1 domain is 3pev.1.B. In the state of the black-and-white drawing of FIG. 14, in the protein structure, the dark gray region is basic (blue), the light gray region is acidic (red), and the white region is neutral.

FIG. 15 shows the alignment of amino acid residues surrounding the key residues of the InsP$_6$-binding pocket of Gle1. Amino acid residues surrounding three key residues located at the InsP$_6$-binding interface of a Gle1 homolog were aligned: *Saccharomyces cerevisiae* (Sc), *Candida albicans* SC5314 (Ca), *Homo sapiens* (Hs), *Mus musculus* (Mm), *Danio rerio* (Dr), *Bos taurus* (Bt), *Arabidopsis thaliana* (At), *Vitis vinifera* (Vv), *Populus trichocarpa* (Pt1), *Glycine max* (Gm), *Nicotiana benthamiana* (Nb), *Ricinus communis* (Rc), *Oryza sativa* (Os), *Zea mays* (Zm), *Hordeum vulgare* (Hv), *Triticum aestivum* (Ta), *Sorghum bicolor* (Sb), *Brachypodium distachyon* (Bd), and *Pinus teada* (Pt2) (SEQ ID NO: 44 to SEQ ID NO: 52, SEQ ID NO: 13, SEQ ID NO: 53, SEQ ID NO: 54, SEQ ID NO: 14 TO SEQ ID NO: 17, and SEQ ID NO: 55 to SEQ ID NO: 57, respectively). Residues conserved between sequences are boxed in black, dark gray or light gray based on the degree of conservation. Green arrows indicate key residues such as R374, K377 and K378 of the InsP$_6$-binding pocket of yeast Gle1. Red arrowheads indicate two non-basic residues generally present in the plant Gle1 protein;

FIG. 16 shows the six largest leaves of leaves of plants. The plants were grown for three weeks in soil (Scale bar=3 cm);

FIG. 17 shows in situ hybridization for visualizing a poly(A) RNA export defect. For in situ hybridization, leaves of the plants were hybridized with a 45-nucleotide oligo (dT) probe labeled with Cy3 at its end as described in the experimental method. Cy3 fluorescence is observed by confocal laser scanning microscopy;

FIGS. 18A, 18B, 18C, 18D, 18E and 18F show seed germination frequencies in response to various abiotic stresses (WT (black): -, ipk1-1: ■ (red), GFP-Gle1 (yellow): -..-, GFP-IS1 (purple): - - -, GFP-IS2 (green): -.-). Seeds are sown on an MS medium containing various additives;

FIG. 19 shows the result of analyzing the content of seed InsP$_6$ using high-performance ion chromatography (HPIC). The HPIC analysis is performed using a soluble extract from mature dry seeds of the plants as described in the experimental method. Peaks corresponding to free phosphate (Pi), InsP$_6$ and InsP$_5$ are marked.

DETAILED DESCRIPTION OF EXEMPLARY EMBODIMENTS

Hereinafter, the present invention will be described in further detail with reference to examples. The examples are merely provided to more fully describe the present invention, and it will be obvious to those of ordinary skill in the art that the scope of the present invention is not limited to the following examples.

EXAMPLES

Experimental Methods

Experimental Method 1. Plant Materials and Growth Conditions

*Arabidopsis thaliana* (ecotype Columbia-0) plants were grown in a growth chamber at 22° C. and 150 µmol m$^{-2}$s$^{-1}$ under a 16-h-light/8-h-dark cycle. The ipk1-1 (SALK_065337) and los4-1 (CS24938) mutants were obtained from Salk (www.salk.edu/) and ABRC (abrc.osu.edu/), respectively. *N. benthamiana* plants, a tobacco species, were grown in a growth room at 22° C. and 80 µmol m$^{-2}$s$^{-1}$ under a 16-h-light/8-h-dark cycle.

Experimental Method 2. Seed Germination Assay

Seeds were sterilized and sown on a medium containing a Murashige and Skoog (MS) salt including vitamins and 0.8% phytoagar with or without addition of NaCl (100 and 200 mM), sucrose (150 and 250 mM) or mannitol (200 and 400 mM). Before sowing, seeds imbibed for 3 days at 4° C. The seeds were incubated on a medium at 4° C. for 1 day after sowing, and then transferred to a growth chamber (22° C., continuous light condition). Seed germination was recorded when cotyledon emergence was visible.

Experimental Method 3. In Situ Hybridization of Poly(A) RNA

In situ hybridization of poly(A) RNA was performed using a 45-nucleotide oligo (dT) probe labeled with Cy3 at its end as described by Lee et al. (Dual functions of *Nicotiana benthamiana* Rae1 in interphase and mitosis. Plant J. 59: 278-291, 2009). Cy3 fluorescence was detected with a confocal laser scanning microscope (CFLSM, Zeiss LSM 510).

Experimental Method 4. Western Blotting

Anti-Gle1 antibodies against two oligopeptides, EEARRKERAHQEEK SEQ ID NO: 19) and MRLYGALVQT (SEQ ID NO: 20), which correspond to amino acid residues 228 to 241 and 465 to 474 of *Arabidopsis* Gle1, respectively, were produced in rabbits using the antibody production service of Cosmogenetech (http://www.cosmogenetech.com). Western blotting was performed using mouse monoclonal antibodies against Myc tag (1:5,000, ABM) or Flag tag (1:10,000, Sigma-Aldrich), a rabbit polyclonal antibody against Gle1 (1:1,000, Cosmogenetech) or a goat polyclonal antibody against GFP (1:5,000, ABM). Subsequently, the membrane was treated with a horseradish peroxidase (HRP)-conjugated goat anti-mouse IgG antibody (1:5000, Invitrogen), a goat anti-rabbit IgG antibody (1:10,000, Invitrogen), or a donkey anti-goat antibody (1:10,000, Santa Cruz Biotechnology). Signals were detected by ImageQuant LAS 4000 (GE Healthcare Life Sciences).

Experimental Method 5. ATPase Assay

A steady-state ATPase assay was performed as described by Alcázar-Román et al. (Inositol hexakisphosphate and Gle1 activate the DEAD-box protein Dbp5 for nuclear mRNA export. Nat. Cell Biol. 8: 711-716, 2006) with slight modifications. The ATPase assay was performed with a LOS4-His protein in a 96-well plate using a buffer containing 20 mM HEPES (pH 7.5), 150 mM NaCl, 3 mM MgCl$_2$, 1 mM DTT, 2 mM ATP, 6 mM phosphoenolpyruvate, 1.2 mM NADH, 1 mg/ml BSA and 2% (v/v) pyruvate kinase/lactate dehydrogenase (Sigma-Aldrich) in a total volume of 100 µl. Polyadenylic acid was added at 50 µg/ml or different concentrations as described above. Absorbance at 340 nm was measured using a VersaMax absorbance microplate reader (Molecular Devices), and the data were analyzed using SoftMax Pro software (Molecular Devices).

Experimental Method 6. Nucleic Acid-Melting Assay

A nucleic acid-melting assay was performed as described by Kim et al. (Cold shock domain proteins and glycine-rich RNA-binding proteins from *Arabidopsis thaliana* can promote the cold adaptation process in *Escherichia coli*. Nucleic Acids Res. 35: 506-516, 2007) using 78-nucleotide-long, 9-bp-containing, hairpin-shaped molecular beacons conjugated with a fluorophore (tetramethylrhodamine) and a quencher (Dabcyl). Spectrofluorometry was performed using a fluorescence spectrophotometer (Hitachi F-2000) at an excitation wavelength of 555 nm and an emission wavelength of 575 nm.

Experimental Method 7. Generation of *Arabidopsis* Dexamethasone (DEX)-Inducible Gle1 RNAi Lines For Gle1 (N) RNAi lines, a 356-bp Gle1 cDNA fragment was amplified by PCR using 5'-atggggattgttttggaac-3' (3$^{rd}$ sequence) (SEQ ID NO: 3) and 5'-ggttcatgatcaaactcttcat-3' (4$^{th}$ sequence) (SEQ ID NO: 4) primers, which contained XhoI and HindIII sites for a sense construct and SpeI and EcoRI sites for an antisense construct. For Gle1 (C) RNAi lines, a 330-bp Gle1cDNA fragment was amplified by PCR using 5'-cacaaagcttgcatttacact-3' (5$^{th}$ sequence) (SEQ ID NO: 5) and 5'-atgctctctcacaacattcac-3' (6$^{th}$ sequence) (SEQ ID NO: 6) primers, which contained XhoI and ClaI sites for a sense construct and SpeI and BamHI sites for an antisense construct. Using these constructs, DEX-inducible Gle1RNAi *Arabidopsis* lines were generated as described by Ahn et al. (2011). For induction of RNAi, the transgenic seedling was grown on a medium containing 10 µM DEX in ethanol (0.033%). Alternatively, the RNAi seedling was sprayed with 30 µM DEX in ethanol (0.033%) and Tween 20 (0.01% w/v).

Experimental Method 8. Virus-Induced Gene Silencing (VIGS)

VIGS was performed in *N. benthamiana* as described by Lee et al. (Dual functions of *Nicotiana benthamiana* Rae1 in interphase and mitosis. Plant J. 59: 278-291, 2009); Ahn et al. (The PP2A regulatory subunit Tap46, a component of the TOR signaling pathway, modulates growth and metabolism in plants. Plant Cell 23: 185-209, 2011); and Cho et al.

(Pescadillo plays an essential role in plant cell growth and survival by modulating ribosome biogenesis. Plant J. 76: 393-405, 2013).

Experimental Method 9. *Agrobacterium*-Mediated Transient Expression

Agroinfiltration was performed as described by Ahn et al. (The PP2A regulatory subunit Tap46, a component of the TOR signaling pathway, modulates growth and metabolism in plants. Plant Cell 23: 185-209, 2011) and Cho et al. (Pescadillo plays an essential role in plant cell growth and survival by modulating ribosome biogenesis. Plant J. 76: 393-405, 2013).

Experimental Method 10. Real-Time Quantitative RT-PCR

Real-time quantitative RT-PCR was performed as described by Ahn et al. (2011) and Cho et al. (2013) using the following primers: 5'-catggatgggcttggttagc-3' ($7^{th}$ sequence) (SEQ ID NO: 7) and 5'-tgtcgcagtggctctgttg-3' ($8^{th}$ sequence) (SEQ ID NO: 8) for detecting Gle1 transcripts in RNAi-Gle1 (N) lines, 5'-tcagccaattactaacacaacctt-3' ($9^{th}$ sequence) (SEQ ID NO: 9) and 5'-gacatgcattacaaatcctcca-3' ($10^{th}$ sequence) (SEQ ID NO: 10) for detecting Gle1 transcripts in RNAi-Gle1 (C) lines, and 5'-atgggtccttcagagagtcct-3' ($11^{th}$ sequence) and 5'-tggaacaccttggtcctaaag-3' ($12^{th}$ sequence) for detecting UBC10 transcripts.

Experimental Method 11. Measurement of Chlorophyll Contents

Chlorophylls were extracted from *N. benthamiana* as described by Terry and Kendrick (Feedback inhibition of chlorophyll synthesis in the phytochrome chromophore-deficient aurea and yellow-green-2 mutants of tomato. Plant Physiol. 119: 143-152, 1999). Spectrofluorometry was performed using a fluorescence spectrophotometer (Hitachi F-2000) at an excitation wavelength of 440 nm and an emission wavelength of 600-700 nm as described by Terry and Kendrick (Feedback inhibition of chlorophyll synthesis in the phytochrome chromophore-deficient aurea and yellow-green-2 mutants of tomato. Plant Physiol. 119: 143-152, 1999).

Experimental Method 12. Immunolabeling of Tobacco BY-2 Cells

Immunocytochemical staining of BY-2 cells was performed as described by Lee et al. (Dual functions of *Nicotiana benthamiana* Rae1 in interphase and mitosis. Plant J. 59: 278-291, 2009). For double-labeling of Gle1 and α-tubulin, BY-2 cells were fixed, permeabilized, and immunolabeled with anti-Gle1 (rabbit polyclonal) antibodies (1:200; Cosmogenetech) and anti-α-tubulin (mouse monoclonal) antibodies (1:1,000; Sigma-Aldrich). Afterward, the cells were incubated with Alexa Fluor 563-conjugated anti-rabbit IgG antibodies (1:1,000; Invitrogen) and Alexa Fluor 488-conjugated anti-mouse IgG antibodies (1:1,000; Invitrogen). After brief staining with DAPI, the BY-2 cells were observed with a confocal laser scanning microscope (CFLSM, Zeiss LSM 510).

Experimental Method 13. Co-Immunoprecipitation

Flag-Gle1 and LOS4-Myc fusion proteins were coexpressed in *Nicotiana benthamiana* by agroinfiltration. Co-immunoprecipitation was performed following the manufacturer's instructions using the ANTI-FLAGM2 Affinity Gel (Sigma-Aldrich). After elution with a 3× FLAG peptide (F4799, Sigma-Aldrich), proteins were subjected to SDS-PAGE and western blotting.

Experimental Method 14. Purification of Recombinant Proteins

Gle1 and Gle1C (aa residues 244-611) were cloned into a pMAL C2X vector (New England Biolabs) for MBP fusion, LOS4 was cloned into a pET-29a vector for His fusion. MBP-Gle1 and MBP-Gle1C proteins were expressed in a BL21 (DE3) strain, and LOS4-His proteins were expressed in a Rosseta (DE3) strain of *Escherichia coli*. Cells were grown at 37° C. to an A600 of 0.4, shifted to 16° C., and induced by 0.25 mM IPTG for 16 hours. The MBP- and His-fusion proteins were purified following the manufacturer's introductions using MBP Excellose (Bioprogen) and His60 Ni Superflow™ resin (Clontech), respectively.

Experimental Method 15. In Vitro Pull-Down Assay

MBP and MBP-Gle1 proteins immobilized on MBP Excellose (Bioprogen) were incubated with LOS4-His proteins for 2 hours at room temperature. Similarly, LOS4-His proteins immobilized on a His60 Ni Superflow™ resin (Clontech) were incubated with MBP or MBP-Gle1 for 2 hours at room temperature. After extensive washing of the resins, the bound proteins were eluted with 2× SDS sample buffer, and the eluted proteins were visualized by Coomassie blue staining.

Experimental Method 16. HPIC

Seed extracts were prepared from mature dry seeds as described by Stevenson-Paulik et al. (Generation of phytate-free seeds in *Arabidopsis* through disruption of inositol polyphosphate kinases. Proc. Natl. Acad. Sci. USA 102: 12612-12617. 2005) with slight modifications. Approximately 15 mg of seeds and 15 mg of acid-washed glass beads (425 to 600 mm; Sigma-Aldrich) were mixed with 20 volumes of 0.4 M HCl. Samples were pulverized using a Mini-BeadBeater 16 (BioSpec Products) for 5 minutes and then boiled for 5 minutes. Samples were pulverized again for 5 minutes and seed extracts were collected by centrifugation for 10 minutes at 15,000 g. The extracts were passed through filters (PTFE, 0.2 μm; Whatman) and analyzed by HPIC (ICS-3000; Dionex) as described by Kim and Tai (Identification of genes necessary for wild-type levels of seed phytic acid in *Arabidopsis thaliana* using a reverse genetics approach. Mol. Genet. Genomics 286: 119-133, 2011) with slight modifications. An IonPac ASH anion exchange column (4×250 mm; Dionex) was eluted with a linear gradient of NaOH from 5 to 80 mM under a flow rate of 1 mL/min for 70 minutes at 35° C. A conductivity detector was used with an electrolytically regenerated suppressor (ERS 500; Dionex) operated with the external water mode at a current of 300 mA. Inositol phosphate was purchased from Sigma-Aldrich, and a standard curve was established for the quantification. All of the measurements were performed in triplicate and expressed as mean±SD.

Experimental Method 17. Statistical Analysis

Two-tailed Student's t-tests were performed using the Minitab 16 program (Minitab Inc.; www.minitab.com/en-KR/default.aspx) to determine the statistical differences between the samples.

Experimental Results

Experimental Result 1. Gle1 Silencing Resulted in Growth Retardation and mRNA Export Defects in *Arabidopsis* and *N. benthamiana*

Figure 10B:
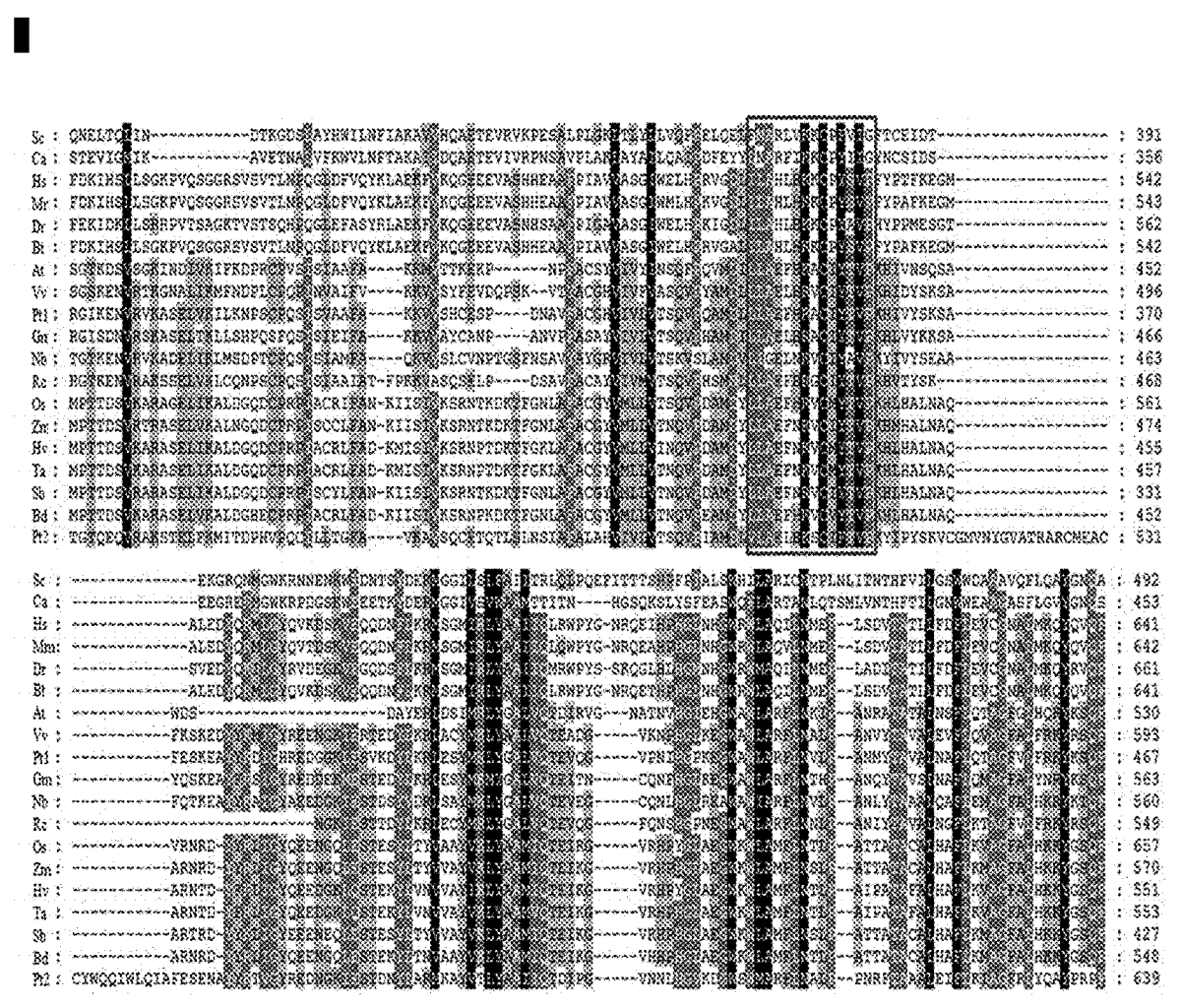

Multispecies sequence alignment revealed that Gle1 is generally found in eukaryotes, and conserved from yeast to humans and plants, particularly, in the Gle1 domain (FIGS. 9 and 10). To determine the in vivo effects of Gle1 defects in *Arabidopsis* and *N. benthamiana*, the inventors employed DEX-inducible RNA interference (RNAi) and VIGS. Transgenic *Arabidopsis* plants (Col-0 ecotype) carried RNAi constructs containing an inverted repeat of a 356-bp N-terminal or 330-bp C-terminal region of *Arabidopsis* Gle1 cDNA under the control of the DEX-inducible transcription system, and were designated as Gle1 (N) and Gle1 (C) RNAi. DEX-inducible Gle1 RNAi plants were grown in soil, and sprayed with ethanol (−DEX) or 30 µM DEX. Upon DEX spraying, Gle1 (N) and Gle1 (C) RNAi plants showed growth retardation (FIG. 1A). When grown on a MS (Murashige and Skoog) medium containing 10 µM DEX, Gle1 (N) and Gle1 (C) RNAi seedlings exhibited retarded shoot and root development (FIG. 1C). Real-time quantitative RT-PCR and western blotting with anti-Gle1 antibodies showed reduced Gle1 mRNA and protein levels in seedlings grown on the (+)DEX medium compared with the (−)DEX control, suggesting DEX-induced Gle1 silencing (FIGS. 1D and 1E). Since Gle1 is an NPC component, the inventors examined whether Gle1 defects cause poly(A) RNA export defects using in situ hybridization (FIG. 1B).

After hybridization with a 45-nucleotide oligo (dT) probe labeled with Cy3 (Cy3-oligo-dT) at its end, poly(A) RNA signals were broadly distributed in the cytosol and nuclei in (−)DEX leaf cells. Meanwhile, (+)DEX leaves accumulated much stronger poly(A) RNA signals in the nuclei, indicating that mRNA export from the nucleus to the cytosol was distributed by Gle1 defects (FIG. 1B).

VIGS was performed in *N. benthamiana* with two constructs NbGle1 (N) and NbGle1 (C) containing a 615-bp N-terminal and 570-bp C-terminal region of Gle1 cDNA, respectively (FIGS. 11A to 11D). VIGS of Gle1 using each construct showed a similar phenotype of growth retardation and abnormal leaf development compared with a TRV control plant. Western blotting using anti-Gle1 antibodies showed that endogenous Gle1 protein levels were reduced in both of NbGle1 (N) and NbGle1 (C) VIGS leaves compared with the TRV control. After in situ hybridization, NbGle1 (N) leaves showed mRNA export defects as observed in *Arabidopsis* Gle1 RNAi plants.

Experimental Result 2. Gle1 Localized in Nuclear Envelope and Cytosol

The inventors examined the subcellular localization of Gle1 by expressing a GFP fusion protein of *Arabidopsis* Gle1 (GFP-Gle1) in *N. benthamiana* using agroinfiltration. Confocal laser scanning microscopy of mesophyll protoplasts and the epidermal cells of a leaf showed that Gle1 is enriched around the nuclear envelope and in the cytosol (FIG. 2A). Subsequently, immunolabeling of tobacco BY-2 cells with anti-Gle1 antibodies indicated endogenous Gle1 localized in the nuclear periphery and the cytosol of BY-2 cells, whereas DAPI staining and anti-α-tubulin antibodies indicated the nuclei (n) and the cortical microtubules, respectively (FIG. 2B). Finally, root cells of transgenic *Arabidopsis* plants carrying the GFP-Gle1 construct fused to the endogenous Gle1 promoter (1,944 bp upstream of the start codon) were observed by confocal microscopy. Green fluorescent signals of GFP-Gle1 were mainly detected in the nuclear envelope and the cytosol of the root cells (FIG. 2C).

Experimental Result 3. Gle1 Interacts with DEAD-Box ATPase LOS4

It has been reported that Gle1 associates with the DEAD-box ATPase/RNA helicase Dbp5 and Nup159 to form an mRNA-exporting module in yeast (Montpetit et al., A conserved mechanism of DEAD-box ATPase activation by nucleoporins and InsP6 in mRNA export, Nature 472: 238-242, 2011). The *Arabidopsis* homolog of yeast Dbp5 is LOS4 (low expression of osmotically responsive genes 4), which plays a critical role in expression of a cold stress-responsive gene and tolerance to chilling and freezing stresses of plants (Gong et al., RNA helicase-like protein as an early regulator of transcription factors for plant chilling and freezing tolerance. Proc. Natl. Acad. Sci. USA 99: 11507-11512, 2002; Gong, et al., A DEAD box RNA helicase is essential for mRNA export and important for development and stress responses in *Arabidopsis*. Plant Cell 17: 256-267, 2005). The los4-1 mutant plants exhibited growth retardation under normal growth conditions (FIG. 3A). As reported by Gong et al. (A DEAD box RNA helicase is essential for mRNA export and important for development and stress responses in *Arabidopsis*. Plant Cell 17: 256-267, 2005), in situ hybridization showed that the los4-1 mutation severely disrupted mRNA export (FIG. 3B). To determine whether *Arabidopsis* Gle1 and LOS4 interact with each other, the inventors first used bimolecular fluorescence complementation (BiFC). Coexpression of YFP$^N$-Gle1 and LOS4-YFP$^C$ resulted in YFP fluorescence in the nuclear periphery and the cytosol (FIG. 3C). Despite the protein expression, the fluorescence between YFP$^N$-Gle1 and YFP$^C$ was not detected, which indicates a lack of protein interaction (FIGS. 3C and 12). Subsequently, the inventors performed a co-immunoprecipitation assay (FIG. 3D). Expression of Flag-fused Gle1 (Flag-Gle1) and Myc-fused LOS4 (LOS4-Myc) was detected by western blotting with anti-Flag and anti-Myc antibodies, respectively (input). When expressed in *N. benthamiana* leaves, two forms of LOS4-Myc proteins were consistently detected in western blots. Flag-Gle1 was immunoprecipitated from leaf extracts using anti-Flag antibodies (IP), and then LOS4-Myc was detected as a co-immunoprecipitant by western blotting with anti-Myc antibodies, suggesting an in vivo interaction between Gle1 and LOS4. A small amount of LOS4-Myc was detected in the control experiment group due to non-specific interactions. For in vitro binding assays, maltose-binding protein (MBP)-fused Gle1 (MBP-Gle1), 6×-histidine-fused LOS4 (LOS4-His), and MBP were purified (FIG. 3E, left). LOS4-His in combination with MBP-Gle1 or MBP were incubated and bound to a nickel resin (for His-tag) or an amylose resin (for MBP-tag). After extensive washing of the resins, resin-bound proteins were eluted and subjected to Coomassie blue staining (FIG. 3E, right). Nickel resin-bound LOS4-His could pull down MBP-Gle1, but not MBP. However, amylose resin-bound MBP-Gle1 could pull down LOS4-His, but not MBP. This suggests that there was no direct interaction between Gle1 and LOS4 in vitro. Collectively, these results suggest that Gle1 and LOS4 interact with each other at the nuclear rim and in the cytosol.

Experimental Result 4. Gle1 Stimulates ATPase Activity of LOS4

To explore the functional relationship between Gle1 and LOS4, the inventors measured LOS4 ATPase activity in the absence or presence of Gle1. First, the inventors purified LOS-His, MBP-Gle1, and the MBP fusion protein of the carboxyl-terminal domain of Gle1 (MBP-Gle1C; amino acid residues 244-611) (FIGS. 3E and 4B). The ATPase activity of LOS4-His was measured by a coupled steady-state spectrophotometric assay as described in the Experimental Methods. The addition of increasing amounts of MBP-Gle1C proteins (0-4 µM) activated LOS4-His ATPase activity in a concentration-dependent manner (FIG. 4C). MBP-Gle1C alone did not show intrinsic ATPase activity, but both MBP-Gle1 (full-length) and MBP-Gle1C exhibited similar abilities to stimulate the ATPase activity of LOS4-His (FIGS. 12A and 12B). The addition of MBP-Gle1C (2 µM) to LOS4-His (1 µM) led to a substantial increase in ATP turnover (FIG. 4D), and the apparent kcat values for LOS4-His alone and LOS4-His with MBP-Gle1C were calculated to be 0.267 and 0.565 $\sec^{-1}$, respectively, resulting in an approximately two-fold increase in the overall catalytic rate of LOS4 by Gle1 (FIG. 4E). When LOS4-His and MBP-Gle1C were used at a ratio of 1:2 for the ATPase assays, the addition of RNA (polyadenylic acid) causes a further increase in LOS4-stimulating activity of Gle1C within the wide range of RNA concentrations, resulting in, maximally, about a 3-fold increase in activity (FIG. 4F).

LOS4 belongs to the DEAD-box RNA helicase gene family in *Arabidopsis*, and its yeast homolog Dbp5 has ATP-dependent RNA helicase activity (Tseng et al., Dbp5p, a cytosolic RNA helicase, is required for poly(A)+ RNA export. EMBO J. 17: 2651-2662 1998; Gong et al., A DEAD box RNA helicase is essential for mRNA export and important for development and stress responses in *Arabidopsis*. Plant Cell 17: 256-267 2005). To test whether Gle1 activates the RNA helicase activity of LOS4, the inventors performed an in vitro nucleic acid-melting assay with LOS4-His and MBP-Gle1 (full length) recombinant proteins using 78 nucleotide-long, 9-bp-containing, hairpin-shaped molecular beacons (FIG. 4G). Melting of the hairpin in the beacons by a helicase caused elimination of a quencher from a fluorophore, resulting in an increase in fluorescence. The beacons have been used to evaluate the helicase activity of RNA chaperones which comprises *Escherichia coli* and *Arabidopsis* cold-shock proteins (Kim et al., Cold shock domain proteins and glycine-rich RNA-binding proteins from *Arabidopsis thaliana* can promote the cold adaptation process in *Escherichia coli*. Nucleic Acids Res. 35: 506-516, 2007; Kim et al., The *Arabidopsis* U12-type spliceosomal protein U11/U12-31K is involved in U12 intron splicing via RNA chaperone activity and affects plant development. Plant Cell 22: 3951-3962, 2010). In the presence of ATP, the beacon itself (control) or the addition of LOS4-His did not increase the fluorescence of the beacons. However, the addition of LOS4-His and MBP-Gle1 at 1:1, 1:2, and 1:4 ratios caused a significant increase in fluorescence in a concentration-dependent manner, implying a role for Gle1 as an activator of LOS4 RNA helicase activity (FIG. 4G). The inability of LOS4-His to induce fluorescence by itself shows that this technique may not be sensitive enough to detect the low basal activity of LOS4. Collectively, such experiment results show that Gle1 serves as an activator of LOS4.

Experimental Result 5. Plant Gle1 Proteins have Modifications in Several Key Residues in $InsP_6$-Binding Pocket Recently, the structure of a Dbp5-$InsP_6$-Gle1 complex of yeast was resolved by protein crystallography, which indicates that $InsP_6$ stabilizes the interaction between Gle1 and Dbp5 by acting as a small-molecule tether (Montpetit et al., A conserved mechanism of DEAD-box ATPase activation by nucleoporins and InsP6 in mRNA export, Nature 472: 238-242, 2011). $InsP_6$ binding to a positively-charged pocket at the interface between Gle1 and C-terminal domain of Dbp5; residues K264, K333, H337, R374, K377 and K378 of Gle1, and K477 and K481 of Dbp5 are involved in the interaction with the phosphate group of $InsP_6$ (Montpetit et al., A conserved mechanism of DEAD-box ATPase activation by nucleoporins and InsP6 in mRNA export, Nature 472: 238-242, 2011). Particularly, the two resides K377 and K378 of yeast Gle1 were identified as critical residues for $InsP_6$ binding according to site-directed mutagenesis (Alcázar-Román et al., Control of mRNA export and translation termination by inositol hexakisphosphate requires specific interaction with Gle1. J. Biol. Chem. 285: 16683-16692, 2010). Computational modeling predicted the surface potential of the *Arabidopsis* and human Gle1 domain based on that of the yeast Gle1 domain (FIG. 14). The $InsP_6$-binding pocket present on the surface of yeast Gle1 only comprises basic amino acid residues to accommodate the negatively charged phosphate groups of $InsP_6$ (FIG. 5A). Human Gle1 was also predicted to have similar characteristics in the $InsP_6$-binding pocket. However, the surface charge of the $InsP_6$-binding site in *Arabidopsis* Gle1 was predicted to be only partially basic, indicating a modification of the pocket (FIG. 5A).

*Arabidopsis* Gle1 residues corresponding to the R374, K377, and K378 residues of yeast Gle1 could be clearly identified due to high homology around the residues (FIG. 15). Interestingly, Gle1 proteins of higher plants (dicotyledons, monocotyledons, and gymnosperms) that were commonly examined had a Glu residue instead of R374, and a neutral residue instead of K378 of yeast Gle1, but a Lys/Arg residue corresponding to K377. Vertebrates (human, mouse, cow and zebra fish) had His, Lys and Lys residues corresponding to R374, K377 and K378 of yeast Gle1, maintaining a basic charge. Thus, the inventors investigated how mutations of these two residues affect the predicted surface charge of the $InsP_6$-binding pocket of *Arabidopsis* Gle1 (FIGS. 4A and 5A). A mutation from A437 to K was designated as $InsP_6$-Sensitive 1 (IS1); double mutations from E433 to K and from A437 to K were designated as $InsP_6$-Sensitive 2 (IS2); and a mutation from K436 to A was designated as $InsP_6$-Dead (ID). Computational modeling showed that IS1 and IS2 mutations progressively increased the basic charge of the $InsP_6$-binding surface, and increasingly mimicked the surface patterns of yeast and human Gle1, whereas in the ID mutation, the basic charge was eliminated (FIG. 5A). However, such mutations did not affect the entire structure of the Gle1 domain (FIG. 14).

Experimental Result 6. Gle1 (IS1) and Gle1 (IS2) Variants Show Increased Sensitivity to $InsP_6$ Concentration for Stimulation of LOS4 ATPase Activity First, the inventors determined whether the Gle1-dependent stimulation of LOS4 ATPase activity is influenced by the presence of $InsP_6$ (FIG. 5B). An ATPase assay was performed with LOS4-His (1 µM) and ATP (2 mM) in the presence or absence of cofactors, including RNA (polyadenylic acid, 50 µg/ml), MBP-Gle1 (full length) (2 µM) and $InsP_6$ (10 µM). The addition of RNA moderately stimulated LOS4 ATPase activity, but the addition of RNA and Gle1 resulted in about a threefold induction of the ATPase activity. The addition of $InsP_6$ to RNA and MBP-Gle1 further stimulated ATPase activity, causing more than about a 4-fold increase, but the addition of an $InsP_6$ analog did not do so. This suggests that $InsP_6$ stimulates LOS4 ATPase activity in combination with Gle1 and RNA (FIG. 5B).

Next, the inventors tested whether the Gle1 variants with a modified $InsP_6$-binding pocket have different sensitivity to $InsP_6$ in the stimulation of the LOS4 ATPase activity. The Gle1 variants, such as Gle1C (IS1), Gle1C (IS2) and Gle1C (ID), were generated by site-directed mutagenesis, and MBP fusion proteins of such mutants were expressed and purified in *E. coli* (FIG. 4B). First, in the absence of $InsP_6$, when incubated with LOS4-His and RNA, MBP-Gle1C and MBP-Gle1C (IS1) activated LOS4 ATPase activity to similar degrees, whereas MBP-Gle1C (IS2) and MBP-Gle1C (ID) showed reduced abilities to stimulate LOS4 (FIG. 5C). Particularly, the K436A mutation in the MBP-Gle1C (ID) variant resulted in more than a 2-fold decrease in stimulating activity. Next, the inventors tested the LOS4-stimulating activity of Gle1C and its variants in the presence of RNA and various concentrations of $InsP_6$ (0-100 µM). While MBP-Gle1C maintained basal stimulating activity with 1 to 100 nM $InsP_6$, it increased the activity with 1 µM $InsP_6$, and reached maximum activity with 10 µM $InsP_6$ (FIG. 5D). MBP-Gle1C (IS1) could increase basal activity in the presence of 100 nM $InsP_6$, and almost reached the maximum stimulation activity with 1 µM $InsP_6$ (FIG. 5E). MBP-Gle1C (IS2), which showed the highest similarity to yeast Gle1 in the $InsP_6$-binding pocket among the variants, was responsive to 1 nM $InsP_6$, and was able to fully stimulate LOS4 ATPase activity in the presence of 100 nM $InsP_6$ (FIG. 5F). Thus, IS1 and IS2 mutations provided increased $InsP_6$ sensitivity to in vitro LOS4 stimulation to *Arabidopsis* Gle1. Meanwhile, MBP-Gle1C (ID) was not influenced by $InsP_6$ regardless of its concentration, suggesting that the K436 residue is critical for $InsP_6$ binding to Gle1 (FIG. 5G).

Experimental Result 7. Expression of $InsP_6$-Sensitive Gle1 Variants Improves Vegetative Growth of ipk1 $InsP_6$ Biosynthetic Mutants Then, the inventors investigated whether the Gle1 (IS1) and Gle1 (IS2) variants functioned better in a low $InsP_6$ background in vivo than wild type Gle1 by testing their abilities to complement the ipk1-1 mutation in *Arabidopsis*. IPK1 encodes inositol 1,3,4,5,6-pentakisphosphate 2-kinase, which is an enzyme that catalyzes the final step of $InsP_6$ biosynthesis, the conversion of $InsP_5$ to $InsP_6$ (Stevenson-Paulik et al., Generation of phytate-free seeds in *Arabidopsis* through disruption of inositol polyphosphate kinases. Proc. Natl. Acad. Sci. USA 102: 12612-12617, 2005; Monserrate and York, Inositol phosphate synthesis and the nuclear processes they affect. Curr. Opin. Cell Biol. 22: 365-373, 2010; Munnik and Nielsen, 2011). The ipk1-1T-DNA inserted mutant of *Arabidopsis* showed considerably reduced $InsP_6$ levels, about 17% and 7.5% of wild type levels in seeds and seedlings, respectively, and had growth defects which became serious in a nutrient-rich condition (Stevenson-Paulik et al., Generation of phytate-free seeds in *Arabidopsis* through disruption of inositol polyphosphate kinases. Proc. Natl. Acad. Sci. USA 102: 12612-12617, 2005). To express Gle1 variants in the ipk1-1 background using *Agrobacterium tumefaciens*-mediated transformation, the inventors introduced GFP fusion constructs of wild type Gle1 (GFP-Gle1), Gle1 (IS1)[GFP-IS1], and Gle1 (IS2) [GFP-IS2] into the ipk1-1 mutant under the control of a CaMV35S promoter. Confocal microscopy showed that GFP-IS1 and GFP-IS2 were localized in the nuclear envelope and the cytosol like GFP-Gle1 (FIG. 6A). Expression of GFP-fused Gle1 and Gle1 variants were identified by western blotting performed with anti-GFP antibodies using leaf extracts from T3-generation independent transgenic lines (FIG. 6B). To evaluate growth, the plants were grown in soil inside a controlled growth chamber. The ipk1-1 mutant plants were significantly smaller and yellower than the wild type (Col-0) under the investigated growth conditions, and exhibited abaxial curling of the rosette leaves, which became more prominent over time (FIGS. 6C and 6D; FIG. 16). After 4 to 5 weeks, the ipk1-1 mutant frequently showed necrosis at the leaf margins.

Compared to the parental ipk1-1 mutant, the transgenic GFP-IS1 and GFP-IS2 lines showed significant improvement in vegetative growth with an increase in the size and greening of leaves and a decrease in the necrosis at the leaf margins, although the leaf curling phenotype still remained (FIGS. 6C and 6D; FIG. 16). Meanwhile, GFP-Gle1 lines showed only slight improvement in plant growth. Leaf chlorophyll contents of the GFP-IS1 and GFP-IS2 plants were much higher than those of the ipk1-1 mutant and GFP-Gle1 plants, suggesting increased photosynthetic capacity (FIG. 6D). When GFP-IS1 and GFP-IS2 plants were about to bolt, their sizes were comparable to those of wild-type plants despite leaf curling (FIG. 6C). However, the ipk1-1 mutant and all of the transgenic lines showed early flowering along with early inhibition of rosette leaf growth, and was increased in the number of inflorescence stems compared to the wild-type plants (FIG. 6E). It is noteworthy that the los4-2/cryophyte site-specific mutation strongly induced early flowering (Gong et al., A DEAD box RNA helicase is essential for mRNA export and important for development and stress responses in *Arabidopsis*. Plant Cell 17: 256-267, 2005).

Based on such a result, the inventors questioned whether the growth defect mainly occurs due to improperly functioning Gle1 because the growth defect of the ipk1-1 mutants is due to a $InsP_6$ defect. Therefore, the inventors tested whether the ipk1-1 mutant has mRNA export defects through in situ hybridization (FIG. 6F; FIG. 17). The ipk1-1 mutant leaf cells accumulated the poly (A) RNA signal in the nucleus, suggesting that the mRNA export defect contributed to abnormal growth of the mutant. However, GFP-IS1 and GFP-IS2 leaves showed normal distribution of the poly(A) RNA signal in the cytosol and nucleus as observed in wild-type leaves, suggesting that expression of the Gle1 variants can rescue the mRNA export defect of the ipk1 mutant. However, expression of GFP-Gle1 only slightly reduced nuclear accumulation of poly(A) RNA.

Experimental Result 8. $InsP_6$-Sensitive Gle1 Variants Improves Seed Yield and Seed Performance of ipk1 Mutant Compared to the wild type and the parental ipk1-1 mutant, the transgenic lines expressing the Gle1 variants were evaluated for a seed weight, a seed yield and a seed germination frequency. There were no apparent differences in seed morphology between these lines (FIG. 7A). A mean weight of 200 mature desiccated seeds was almost uniform between the wild type, ipk1-1 and all transgenic lines (FIG. 7B). However, the seed yield of the ipk1 mutant was only about 52% of that of the wild type. This is because many siliques of the mutant plant contained sterile seeds (FIG. 7B).

However, GFP-IS1 and GFP-IS2 plants had seed yields which were comparable to or even higher than the wild-type level. Meanwhile, the GFP-Gle1 plant showed only a slightly increased seed yield compared to the ipk1-1 mutant (FIG. 7B). The seed germination frequencies of the mutant, wild type and transgenic lines were very similar on MS media (FIG. 7C). However, in response to 200 mM NaCl, the ipk1-1 seeds germinated significantly earlier than wild-type seeds with green open cotyledons, and soon perished (FIG. 7D). The reduced sensitivity to salt stress suggests inhibited stress signaling in variant seeds. Interestingly, GFP-IS1 and GFP-IS2 seeds retained normal sensitivity to the salt stress, but GFP-Gle1 seeds behaved similar to the mutant seeds, suggesting that Gle1 has a critical function for plant responses to the salt stress. In response to other abiotic stresses such as sucrose and mannitol, no significant differences in germination frequencies were observed among these seeds (FIG. 18). These results demonstrate that expression of the mutants can greatly rescue the detects of $InsP_6$ in seeds as well as in vegetative tissues.

It has been reported that a seed phytate level was reduced to about 83% of the ipk1-1 mutant (Stevenson-Paulik et al., Generation of phytate-free seeds in Arabidopsis through disruption of inositol polyphosphate kinases. Proc. Natl. Acad. Sci. USA 102: 12612-12617, 2005). The inventors performed a high-performance ion chromatography (HPIC) analysis on water soluble extracts from mature dried seeds to measure seed phytate content in the transgenic plants (FIG. 7E; FIG. 19). In both the transgenic lines and the ipk1-1 mutants, the seed phytate levels decreased by about 15% of the wild-type level, but inorganic phosphate levels in the seeds only moderately increased (FIG. 7E). Instead, the transgenic lines and the mutants accumulated high levels of $InsP_5$ in seeds (FIG. 19). These results were consistent to the conventional report (Stevenson-Paulik et al., Generation of phytate-free seeds in Arabidopsis through disruption of inositol polyphosphate kinases. Proc. Natl. Acad. Sci. USA 102: 12612-12617, 2005), suggesting that expression of the Gle1 variants did not change cellular $InsP_6$ levels in the transgenic plants.

Experimental Result 9. IPK1 Interacts with LOS4, but not with Gle1, in Nuclear Envelope and Cytosol In mature seeds, phytic acid accumulates in protein storage vacuoles (PSV) as stable salts (phytins) by binding to mineral cations (Lott, 1995). It was suggested that phytic acid is synthesized in association with the endoplasmic reticulum (ER), transferred to ER lumen, and then transported to vesicles of PSV in developing seeds (Otegui et al., Developing seeds of Arabidopsis store different minerals in two types of vacuoles and in the endoplasmic reticulum. Plant Cell 14: 1311-1327, 2002). However, there was almost no experimental evidence relating to the synthesis and transport of phytic acid in plants. Thus, the inventors investigated the subcellular localization of IPK1 of Arabidopsis by GFP fusion. Confocal microscopy detected IPK1-GFP fluorescence mainly in the cytosol and around the nuclear envelope (FIG. 8A). Moreover, BiFC suggested that IPK1 interacts with LOS4 in the nuclear envelope and the cytosol, but not with Gle1 or the control $YFP^N$, despite normal expression of the proteins (FIGS. 8B and 8C). The close proximity of IPK1 to LOS4 and Gle1 may provide local enrichment of $InsP_6$ to support mRNA export and possibly other LOS4/Gle1-mediated processes, which take place in the nuclear envelope or the cytosol.

[Discussion]

In yeast, plants and mammals, Gle1 is a component for NPC, but is also present in the cytosol. In the present invention, the inventors investigated the nuclear function of Gle1 in plants, and developed a novel technique for reducing the adverse effect of the low-phytate characteristic using Gle1 variants. Plant Gle1 is involved in mRNA export in the nucleus by interacting with LOS4 to stimulate LOS4 ATPase activity. Functions of Gle1 are essential for embryogenesis (Braud et al., LONO1 encoding a nucleoporin is required for embryogenesis and seed viability in Arabidopsis. Plant Physiol. 160: 823-836, 2012), and critical for the postembryonic growth of plants (FIG. 1), which is reminiscent of essential Gle1 functions in both yeast and mammals (Murphy and Wente, An RNA-export mediator with an essential nuclear export signal. Nature 383: 357-360, 1996; Nousiainen et al., Mutations in mRNA export mediator GLE1 result in a fetal motoneuron disease. Nat. Genet. 40: 155-157, 2008). Recently, Montpetit et al. (A conserved mechanism of DEAD-box ATPase activation by nucleoporins and InsP6 in mRNA export, Nature 472: 238-242, 2011) suggested molecular mechanisms for functions of DEAD-box ATPase Dbp5 and its activator Gle1 for mRNA export in yeast using protein crystallography. In these models, Gle1 induced the structural change of Dbp5 to stimulate RNA release, which has been known as a rate-limiting step in the hydrolytic cycle of a DEAD-box RNA helicase. RNA release subsequently causes Nup159 binding to Dbp5 to prevent rebinding of the RNA and allow enzyme recycling. In addition, $InsP_6$ binds to a positively-charged pocket at the interface between Gle1 and Dbp5, thereby mediating and stabilizing the Gle1-Dbp5 interaction (Montpetit et al., A conserved mechanism of DEAD-box ATPase activation by nucleoporins and InsP6 in mRNA export, Nature 472: 238-242, 2011).

Although detailed mechanisms of Gle1 and LOS4 in an mRNA export pathway in plants remain to be determined, the results of the present invention suggest that the DEAD-box ATPase/RNA helicase LOS4 is activated by Gle1 in a similar manner as described for the Dbp5 activation in yeast. However, the requirement of Gle1 for a co-activator $InsP_6$ seems to be different between yeast and plants. In yeasts, the addition of $InsP_6$ (100 nM) to Gle1 and RNA causes an additional 3- to 4-fold increase in Dbp5 ATPase activity (Dossani et al., 2009; Montpetit et al., A conserved mechanism of DEAD-box ATPase activation by nucleoporins and InsP6 in mRNA export, Nature 472: 238-242, 2011), and 30% additional increase in LOS4 activity in plants even at higher $InsP_6$ (10 µM) concentrations (FIG. 5B). At the interface between the C-terminal domains of Gle1 and Dbp5, an $InsP_6$-binding pocket is aligned with basic amino acids (K264, K333, H337, R374, K377, and K378 of Gle1, and K477 and K481 of Dbp5), and thus interacts with a phosphorus group of $InsP_6$ (Montpetit et al., A conserved mechanism of DEAD-box ATPase activation by nucleoporins and InsP6 in mRNA export, Nature 472: 238-242, 2011). Since the K477 and K481 residues of Dbp5 are conserved in LOS4, relative inefficiency of $InsP_6$ as a Gle1 cofactor for LOS4 activation is likely caused by the modification of the key residues of plant Gle1 proteins that reduce the basicity of the $InsP_6$-binding pocket. Despite the seemingly imperfect structure of the pocket in plant Gle1, unless InsP$_6$ levels of the plant cells are substantially reduced, an LOS4/Gle1-mediated mRNA export pathway is functional in plants as in the ipk1 mutants (FIG. 6F). The finding that the expression of Gle1 variants comprising a basic InsP$_6$-binding pocket more fully restores mRNA export than that of ipk1 mutants means that InsP$_6$ is an important element in LOS4/Gle1-mediated mRNA export in plants.

However, Gle1 may directly interact with LOS4 in vitro, and Gle1 only may stimulate LOS4 activity in the absence of InsP$_6$ (FIGS. 3E and 4). InsP$_6$ may be required to fine-tune the interaction strength between Gle1 and LOS4 to stimulate LOS4 activity to be over a specific threshold level required for its normal functions. InsP$_6$ is the key species of inositol phosphate in plants, animals and yeast. In mammals, InsP$_6$ concentrations in cells range from 10 to 20 µM according to tissue type, are about 352 µM in vegetative cells, and are high as about 2 mM in spores of Dicteostelium. In plants, although the vegetative tissue contains much lower InsP$_6$, InsP$_6$ is estimated to account for one to several percent of the dry weight of seeds (Raboy, Seeds for a better future: 'low phytate' grains help to overcome malnutrition and reduce pollution. Trends Plant Sci. 6:458-462, 2001; Stevenson-Paulik et al., Generation of phytate-free seeds in *Arabidopsis* through disruption of inositol polyphosphate kinases. Proc. Natl. Acad. Sci. USA 102: 12612-12617, 2005). However, the IPK1 enzyme was abundant at the nuclear rim as well as in the cytosol of leaf cells, and interacted with LOS4 (FIG. 8). Therefore, concentrations of InsP$_6$ may be relatively high in the proximity of the LOS4 and Gle1 of the NPC in which mRNA export takes place. This can be the reason that plant Gle1 can activate LOS4 at sufficient levels despite apparently low affinity to the InsP$_6$-binding surface.

InsP$_6$ has been shown to possess a diverse set of cellular functions, including mRNA export, translation control, chromatin remodeling, RNA editing, and DNA repair, in yeast and mammals (Hanakahi and West, Specific interaction of IP6 with human Ku70/80, the DNA-binding subunit of DNA-PK. EMBO J. 21: 2038-2044, 2002; Macbeth et al., Inositol hexakisphosphate is bound in the ADAR2 core and required for RNA editing. Science 309: 1534-1539, 2005; Bolger et al., The mRNA export factor Gle1 and inositol hexakisphosphate regulate distinct stages of translation. Cell 134: 624-633, 2008; Montpetit et al., A conserved mechanism of DEAD-box ATPase activation by nucleoporins and InsP6 in mRNA export. Nature 472: 238-242, 2011). In plants, InsP$_6$ has been associated with auxin signaling, an ABA reaction in guard cells and plant defense reactions by binding to the auxin receptor TIR1 (Lemtiri-Chlieh et al., Inositol hexakisphosphate is a physiological signal regulating the K+-inward rectifying conductance in guard cells. Proc. Natl. Acad. Sci. USA 97: 8687-8692, 2000; Tan et al., Mechanism of auxin perception by the TIR1 ubiquitin ligase. Nature 446: 640-645, 2007; Murphy et al., A role for inositol hexakisphosphate in the maintenance of basal resistance to plant pathogens. Plant J. 56: 638-652, 2008). In yeast, the Δipk1 mutation abolished InsP$_6$ accumulation and caused synthetic lethality combined with alleles of Gle1, Dbp5 and Nup159 (Miller et al., Cytoplasmic inositol hexakisphosphate production is sufficient for mediating the Gle1-mRNA export pathway. J. Biol. Chem. 279: 51022-51032, 2004; Weirich et al., The N-terminal domain of Nup159 forms a beta-propeller that functions in mRNA export by tethering the helicase Dbp5 to the nuclear pore. Mol. Cell 16: 749-760 2004; Weirich et al., Activation of the DExD/H-box protein Dbp5 by the nuclear-pore protein Gle1 and its coactivator InsP6 is required for mRNA export. Nat. Cell Biol. 8: 668-676 2006). IPK1$^{-/-}$ variant mice died during early embryogenesis, showing the importance of InsP$_6$ for early embryogenesis of mammals. However, their heterozygous littermates developed normally with normal cellular InsP$_6$ levels and elevated InsP$_5$ levels (Verbsky et al., Disruption of the mouse inositol 1,3,4,5,6-pentakisphosphate 2-kinase gene, associated lethality, and tissue distribution of 2-kinase expression. Proc. Natl. Acad. Sci. USA 102: 8448-8453, 2005). The ipk1-1 mutation in *Arabidopsis*, which caused >70% decrease in IPK1 mRNA levels, caused stunted growth, and reduced seed yields and abnormal seed germination (FIGS. 6 and 7). The finding of the inventors that expression of Gle1 variants, IS1 and IS2, can rescue the mRNA export defect of the ipk1 mutant, and significantly restore the growth and yield of the ipk1 mutant shows that Gle1 plays a critical role in mediating InsP$_6$ functions in plant growth and reproduction (FIGS. 6 and 7). It would be interesting to examine whether plant Gle1 and InsP$_6$ are involved in translation control in the cytosol as reported in yeast, in addition to their NPC-related function (Bolger et al., The mRNA export factor Gle1 and inositol hexakisphosphate regulate distinct stages of translation. Cell 134: 624-633, 2008; Kutay and Panse, Gle1 does double duty. Cell 134: 564-566, 2008). The observed incomplete complementation of the ipk1 phenotypes by the Gle1 variants is likely caused by other functions of InsP$_6$ that are mediated by Gle1 (FIG. 6). Interestingly, expression of the Gle1 variants rescued the salt-insensitive germination of ipk1-1 seeds, and subsequent death (FIG. 7D). Thus, the restoration of mRNA export in the ipk1-1 seeds may cause restoration of normal stress signaling for salt adaptation. In yeast, intact NPC is essential for cell survival at high osmolarity, and HOG1 stress-activated kinase phosphorylates nucleoporins to facilitate mRNA export upon osmostress (Regot et al., The Hog1 stress-activated protein kinase targets nucleoporins to control mRNA export upon stress. J. Biol. Chem. 288: 17384-17398, 2013). *Arabidopsis* los4-1 and los4-2 mutations are linked to chilling and/or heat stresses by causing defective mRNA export under stress conditions (Gong et al., RNA helicase-like protein as an early regulator of transcription factors for plant chilling and freezing tolerance. Proc. Natl. Acad. Sci. USA 99: 11507-11512, 2002; Gong, et al., A DEAD box RNA helicase is essential for mRNA export and important for development and stress responses in *Arabidopsis*. Plant Cell 17: 256-267, 2005). These results suggest that LOS4-InsP$_6$-Gle1-mediated mRNA export is responsive to environmental stresses and thus plays a critical role in plants.

To solve the nutritional and environmental problems related to dietary seed phytic acid, various approaches have been used to cultivate low-phytate crops. However, since the synthetic pathway of phytic acid is associated with various cellular pathways of plants, low-phytic acid (lpa) mutant crops showed defects in seed yields, seed weights, germination and emergence, stress responses and disease susceptibility (Raboy et al., Origin and seed phenotype of maize low phytic acid 1-1 and low phytic acid 2-1. Plant Physiol. 124: 355-368, 2000; Raboy, Seeds for a better future: 'low phytate' grains help to overcome malnutrition and reduce pollution. Trends Plant Sci. 6:458-462, 2001; Raboy, Approaches and challenges to engineering seed phytate and total phosphorus. Plant Sci. 177: 281-296, 2009; Meis et al., Seed source effect on field emergence of soybean lines with reduced phytate and raffinose saccharides. Crop Sci. 43: 1336-1339, 2003; Bregitzer and Raboy, Effects of four independent lowphytate mutations on barley agronomic performance. Crop Sci. 46: 1318-1322, 2006; Murphy et al., A role for inositol hexakisphosphate in the maintenance of basal resistance to plant pathogens. Plant J. 56: 638-652, 2008). To avoid such adverse effects, seed-specific targeting of the low-phytate characteristic has been used more recently. Silencing of a gene for phytic acid metabolism using a seed-specific promoter or seed-specific expression of microbial phytases led to low-phytate levels of seeds in maize, rice, wheat, and soy bean (Shi et al., Embryospecific silencing of a transporter reduces phytic acid content of maize and soybean seeds. Nat. Biotechnol. 25: 930-937, 2007; Bilyeu et al., Quantitative conversion of phytate to inorganic phosphorus in soybean seeds expressing a bacterial phytase. Plant Physiol. 146: 468-477, 2008; Kuwano et al., Generation of stable 'low phytic acid' transgenic rice through antisense repression of the 1D-myo-inositol 3-phosphate synthase gene (RINO1) using the 18-kDa oleosin promoter. Plant Biotechnol. J. 7: 96-105, 2009; Ali et al., Development of low phytate rice by RNAi mediated seed-specific silencing of inositol 1,3,4,5,6-pentakisphosphate 2-kinase gene (IPK1). PLoS ONE 8: e68161, 2013; Li et al., Seed-specific silencing of OsMRP5 reduces seed phytic acid and weight in rice. Transgenic Res. 23: 585-599, 2014). However, undesirable effects such as defects in seed weight, germination frequency and seedling emergence were still observed in several trials (Bilyeu et al., Quantitative conversion of phytate to inorganic phosphorus in soybean seeds expressing a bacterial phytase. Plant Physiol. 146: 468-477, 2008; Kuwano et al., Generation of stable 'low phytic acid' transgenic rice through antisense repression of the 1D-myo-inositol 3-phosphate synthase gene (RINO1) using the 18-kDa oleosin promoter. Plant Biotechnol. J. 7: 96-105, 2009; Li et al., Seed-specific silencing of OsMRP5 reduces seed phytic acid and weight in rice. Transgenic Res. 23: 585-599, 2014). Such controversial results may be caused by differences in reduction of phytic acid in seeds used in the present invention, the identities, genes, and promoters of plant species, and disturbance of phosphorus homeostasis in such plants. Therefore, development of high yield low-phytate crops seems to be attempted due to unexpected downstream effects of the $InsP_6$ defect.

The inventors developed a new technique for reducing adverse effects of the low-phytate characteristic on plant growth, seed yield, and seed germination by rescuing the mRNA export defect of the $InsP_6$-deficient ipk1 mutants using $InsP_6$ sensitivity-increased Gle1 variants. Introduction of IS1 and IS2 variants into low-phytate crops may improve seed yields and seed performance by eliminating impediments such as the mRNA export defect and other Gle1/$InsP_6$-derived defects, and will become the basis for the development of high yield, low-phytate and continuously grown seed crops.

Features and advantages of the present invention are summarized as follows:

First, the inventors identified that Gle1, as well as $InsP_6$, serves as an activator of a LOS4 ATPase/RNA helicase for mRNA export in plants.

Meanwhile, Gle1 variants with mutations to increase a basic charge on an $InsP_6$-binding surface show increased sensitivity to $InsP_6$ concentrations for the stimulation of LOS4 ATPase activity in vitro.

In addition, expression of the Gle1 variants with the increased $InsP_6$ sensitivity rescues the mRNA export defect caused by ipk1 $InsP_6$-deficient mutation, thereby highly increasing vegetative growth, seed yield, seed performance and tolerance to abiotic stresses of the mutant.

This indicates that Gle1 is a major factor responsible for mediating an $InsP_6$ function in plant growth and reproduction, and the expression of the Gle1 variants can be a strategy that can cultivate high yield low-phytate crops by reducing the adverse effects of the low-phytate multination.

From above, specific parts of the present invention have been described in detail. However, it will be apparent to those of ordinary skill in the art that such detailed descriptions are just exemplary embodiments, and thus the scope of the present invention is not limited thereto. Therefore, the actual range of the present invention will be defined by the accompanying claims and equivalents thereof.

The invention claimed is:

1. A non-natural synthetic nucleic acid molecule comprising a nucleotide sequence having at least 90% identity to the nucleotide sequence of SEQ ID NO: 1 and which encodes plant Gle1 protein variant:
wherein said plant Gle1 protein variant comprises a phytic acid-binding pocket represented by SEQ ID NO: 18, wherein the eighth amino acid residue of SEQ ID NO: 18 is substituted with a basic amino acid residue and the fourth amino acid residue of SEQ ID NO: 18 is selected from Glu and a basic amino acid residue, and wherein transgenic expression of said nucleotide sequence encoding said plant Gle1 protein in a transgenic plant increases seed yield, seed germination, plant growth or abiotic stress tolerance as compared to a control plant of the same plant species grown under identical conditions and lacking said non-natural synthetic nucleic acid molecule.

2. The non-natural synthetic nucleic acid molecule of claim 1, wherein the basic amino acid residue is Arg or His.

3. The non-natural synthetic nucleic acid molecule of claim 1, wherein the basic amino acid residue is Lys.

4. The non-natural synthetic nucleic acid molecule of claim 1, wherein the plant Gle1 protein variant comprises the phytic acid-binding pocket of any one of the amino acid sequences of SEQ ID NOs: 13 to 17, and
wherein the eighth amino acid residue or the fourth and the eighth amino acid residues of any one of the amino acid sequences of SEQ ID NOs: 13 to 17 are substituted with a basic amino acid residue.

5. The non-natural synthetic nucleic acid molecule of claim 1, wherein the plant Gle1 protein variant is represented by SEQ ID NO: 2, wherein Ala residue 437 in the sequence of SEQ ID NO: 2 is substituted with a basic amino acid residue or Ala residue 437 and Glu residue 433 in the sequence of SEQ ID NO: 2 are substituted with a basic amino acid residue.

6. A plant Gle1 protein variant encoded by the non-natural synthetic nucleic acid molecule of claim 1.

7. A gene delivery system comprising the plant Gle1 protein variant-encoding non-natural synthetic nucleic acid molecule of claim 1, wherein the gene delivery system comprises a plant expression recombinant vector.

8. The gene delivery system of claim 7, wherein the recombinant vector for plant expression comprises:
(a) the plant Gle1 protein variant-encoding non-natural synthetic nucleic acid molecule; (b) a promoter operatively linked to said non-natural synthetic nucleic acid molecule for expression of RNA molecules in plant cells; and (c) a poly A signal sequence acting in plant cells to cause polyadenylation at the 3' end of said RNA molecules.

9. A composition for transforming plants, comprising the gene delivery system of claim 7.

10. A transgenic plant cell transformed with the non-natural synthetic nucleic acid molecule of claim 1.

11. A transgenic plant transformed with the non-natural synthetic nucleic acid molecule of claim 1.

12. A method of preparing a transgenic plant having increased seed yield, germination, growth or abiotic stress tolerance, comprising:
   - transforming a plant with a plant expression recombinant vector, wherein said plant expression recombinant vector comprises said plant Gle1 protein variant-encoding non-natural synthetic nucleic acid molecule of claim 1, wherein expression of said plant Gle1 protein variant in said transgenic plant increases seed yield, germination, growth or abiotic stress tolerance as compared to a control plant of the same species lacking said plant expression recombinant vector and grown under identical growth conditions.

13. The method of claim 12, wherein the transgenic plant is a phytic acid-deficient plant.

14. The transgenic plant of 10, wherein the transgenic plant is a dicotyledonous plant.

15. The transgenic plant of claim 10, wherein the transgenic plant is selected from *Arabidopsis thaliana* and *Glycine max.*

16. The transgenic plant of 10, wherein the transgenic plant is a monocotyledonous plant.

17. The transgenic plant of claim 10, wherein the transgenic plant is selected from *Oryza sativa, Zea mays, Hordeum vulgare, Triticum aestivum*, and *Sorghum bicolor.*

* * * * *

UNITED STATES PATENT AND TRADEMARK OFFICE
CERTIFICATE OF CORRECTION

PATENT NO. : 10,793,871 B2
APPLICATION NO. : 15/543882
DATED : October 6, 2020
INVENTOR(S) : Pai et al.

Page 1 of 1

It is certified that error appears in the above-identified patent and that said Letters Patent is hereby corrected as shown below:

In the Claims

Column 77, Line 20: Claim 1, Delete "which encodes plant" and insert -- which encodes a plant --

Signed and Sealed this
Seventeenth Day of November, 2020

Andrei Iancu
*Director of the United States Patent and Trademark Office*